United States Patent [19]
Cevc

[11] Patent Number: 6,165,500
[45] Date of Patent: *Dec. 26, 2000

[54] PREPARATION FOR THE APPLICATION OF AGENTS IN MINI-DROPLETS

[75] Inventor: Gregor Cevc, Heimstetten, Germany

[73] Assignee: Idea AG, Munich, Germany

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 07/844,664

[22] Filed: Apr. 8, 1992

[30] Foreign Application Priority Data

| Aug. 24, 1990 | [DE] | Germany | 40 26834 |
| Aug. 24, 1990 | [DE] | Germany | 40 26833 |
| Mar. 6, 1991 | [DE] | Germany | 41 07153 |
| Aug. 22, 1991 | [WO] | WIPO | PCTEP91/01596 |

[51] Int. Cl.⁷ .................................. A61K 9/127
[52] U.S. Cl. .................. 424/450; 428/402.2; 424/94.3
[58] Field of Search .................. 424/450, 1.21, 424/9.321, 9.51, 417, 96.3; 428/402.2; 436/829; 935/54

[56] References Cited

U.S. PATENT DOCUMENTS 4,911,928  3/1990  Wallach .................. 424/450

FOREIGN PATENT DOCUMENTS

| 0 102 324 | 3/1984 | European Pat. Off. . |
| 0 211 647 | 2/1987 | European Pat. Off. . |
| 0 220 797 | 5/1987 | European Pat. Off. . |
| 0220797 | 5/1987 | European Pat. Off. . |
| 0 280 492 | 8/1988 | European Pat. Off. . |
| 0 475 160 | 3/1992 | European Pat. Off. . |
| 30 16 976 | 11/1980 | Germany . |
| 37 13 494 | 10/1987 | Germany . |
| WO 87/01938 | 4/1987 | WIPO . |
| WO 88/07362 | 10/1988 | WIPO . |

OTHER PUBLICATIONS

V.M. Knepp et al., "Controlled Drug Release from a Novel Liposomal Delivery System. II. Transdermal Delivery Characteristics" on Journal of Controlled Release 12(1990) Mar., No. 1, Amsterdam, NL, pp. 25–30. (Exhibit A).

C.E. Price, "A Review of the Factors Influencing the Penetration of Pesticides Through Plant Leaves" on I.C.I. Ltd., Plant Protection Division, Jealott's Hill Research Station, Bracknell, Berkshire RG12 6EY, U.K., pp. 237–252. (Exhibit B).

K. Karzel and R.K. Liedtke, "Mechanismen Transkutaner Resorption" on Grandlagen/Basics, pp. 1487–1491. (Exhibit C).

Michael Mezei, "Liposomes as a Skin Drug Delivery System" 1985 Elsevier Science Publishers B.V. (Biomedical Division), pp 345–358. (Exhibit E).

Adrienn Gesztes and Michael Mazei, "Topical Anesthesia of the Skin by Liposome–Encapsulated Tetracaine" on Anesth Analg 1988; 67: pp 1079–81. (Exhibit F).

Harish M. Patel, "Liposomes as a Controlled–Release System" on Biomecial Society Transactions 609th Meeting, Leeds, pp 513–516. (Exhibit G).

(List continued on next page.)

Primary Examiner—Gollamudi S. Kishore
Attorney, Agent, or Firm—Davidson, Davidson & Kappel, LLC

[57] ABSTRACT

The invention relates to a preparation for the application of agents in the form of minuscule droplets of fluid, in particular provided with membrane-like structures consisting of one or several layers of amphiphilic molecules, or an amphiphilic carrier substance, in particular for transporting the agent into and through natural barriers such as skin and similar materials. The preparation contains a concentration of edge active substances which amounts to up to 99 mol-% of the agent concentration which is required for the induction of droplet solubilization. Such preparations are suitable, for example, for the non-invasive applications of antidiabetics, in particular of insulin. The invention, moreover, relates to the methods for the preparation of such formulations.

35 Claims, 21 Drawing Sheets

OTHER PUBLICATIONS

Philip G. Green, et al., "In Vitro and in Vivo Enhancement of Skin Permeation with Oleic and Lauric Acids" on International Journal of Pharmaceutics, 48 (1988), pp 103–111. (Exhibit H).

Guia M. Golden et al., "Role of *Stratum Corneum* Lipid Fluidity in Transdermal Drug Flux" on Journal of Pharmaceutical Sciences vol. 76, No. 1, Jan. 1987, American Pharmaceitucal Association, pp. 25–28. (Exhibit I).

Bruce J. Aungst et al., "Enhancement of Naloxone Penetration Through Human Skin in Vitro Using Fatty Acids, Fatty Alcohols, Surfactants, Sulfoxides and Amides" on International Journal of Pharmaceutics, 33(1986), pp 225–234. (Exhibit J).

Ronald R. Burnette et al., "Characterization of the Permselective Properties of Excised Human Skin During Lontophoresis" on Journal of Pharmaceutical Sciences vol. 76, No. 10, Oct. 1987, American Pharmaceutical Association, pp 765–773. (Exhibit K).

E.C. Katoulis et al., "Efficacy of a New Needleless Insulin Delivery System Monitoring of Blood Glucose Fluctuations and Free Insulin Levels" on International Journal of Artifical Organs vol. 12, No. 5, 1989, pp 333–338. (Exhibit L).

Ovais Siddiqui et al., "Nonparenteral Administration of Peptide and Protein Drugs" on CRC Critical Reviews in Therapeutic Drug Carrier Systems, vol. 3, Issue 3, pp 195–208. (Exhibit M).

Abstract searched from Derwent World Patents Index Latest. (Exhibit N).

Cevc, G. et al., "Ultraflexible vesicles, Transfersomes, have an extremely low pore penetration resistance and transport therapeutic amounts of insulin across the intact mammalian skin", *Biochimica et biophysica acta,* 1368 pp. 201–215 (1998).

Cevc, G., "Material Transport Across Permeability Barriers by Means of Lipid Vesicles", *Handbook of Biological Physics,* vol. 1, pp. 465–490 (1995).

Mayer, L.D. et al., "Vesicles of variable sizes produced by a rapid extrusion procedure", *Biochimica et Biophysica Acta,* 858 pp. 161–165 (1986).

Patel, H. M. et al., "Oral Administration of Insulin by Encapsulation Within Liposomes", *FEBS Letters,* 62(1):60–63 (Feb. 1976).

Mayer BBA 858 (1986) p 161–168.

Patel FEBS Letters 62 #1, Feb. 1976, p 60.

PREPARATION FOR THE APPLICATION OF AGENTS IN MINI-DROPLETS

BACKGROUND OF THE INVENTION

The present invention relates to a novel type of preparations suitable for the application of different agents in the form of a minuscule droplet or, in particular, a vesicle consisting of one or a few membrane-like amphiphile assemblies. These can mediate the transport of agents into and through a series of natural permeability barriers or through the constrictions in such barriers; for example, through intact skin or similar organs. The invention further relates to a procedure for the large-scale production of such carriers. As a special example, non-invasive application of antidiabetics is described for the case of insulin.

The application of various agents is often hampered by the presence of barriers with a low permeability to such agents. Owing to skin impermeability, for example, many common therapeutic agents must be applied per os or parenterally (i.v., i.m., i.p.). Intrapulmonary and intranasal applications of aerosols, the use of rectal formulations, gels for mucous applications, or use of occular formulations are only practicable in certain areas and not for all types of drugs. The transport of different agents into plant tissues is subject to even more severe constraints due to the high permeability barrier of the cuticular wax layers.

Noninvasive drug application through permeability barriers thus would be advantageous in many cases. In humans and animals one would expect such a percutaneous application of agents to protect the agents from degradation in the gastro-intestinal tract; modified drug distribution could possibly also be achieved. Such drug application, moreover, would influence the pharmacokinetics of the agent molecules and permit simple as well as multiple noninvasive therapy. (Karzel K., Liedtke, R. K. (1989) Arzneim. Forsch./Drug Res. 39, 1487–1491). In the case of plants, improved penetration into or through the cuticle could reduce the drug concentration required for a given application and thus significantly diminish pollution problems (Price, C. E. (1981) In: The plant cuticle (D. F. Cutler, K. L. Alvin, C. E. Price, Edits.), Academic, New York, pp. 237–252).

There are many reports on different attempts to increase the permeability of intact skin by suitable manipulations (cf. Karzel und Liedtke, op. cit.). Jet injection (Siddiqui & Chien (1987) Crit. Rev. Ther. Drug. Carrier. Syst. 3, 195–208.), the use of electric fields (Burnette & Ongpipattanakul (1987) J. Pharm. Sci. 76, 765–773) or chemical penetration enhancers, such as solvents and surfactants, are particularly worth mentioning. A long list of additives which have been used to enhance the penetration of one particular water soluble agent (Nolaxon) into skin, for example, is given in the work by Aungst et al. (1986, Int. J. Pharm. 33, 225–234). This list encompasses nonionic substances (including long-chain alcohols, surfactants, zwitterionic phospholipids, etc.), anionics (most notably fatty acids), cationic long-chain amines, sulfoxides as well as different amino-derivatives; amphotheric glycinates and betaines are also mentioned. Despite all this, the problem of agent penetration into skin has as yet not at all—or not satisfactorily—been solved.

A survey of procedures used for increasing the penetration of agents through a plant cuticle is given in the work by Price (1981, op.cit.). To date it has been common to simply add chemical penetration enhancers to the mixture of agent and other molecules; applications to human skin were the only case in which additives were sometimes applied in advance, in the form of an organic solution. The reason for this application form was the current concept for the action of penetration enhancers: to date one has studied, discussed, and believed that, in general, any facilitated agent penetration is a consequence of skin fluidization, on the one hand (Golden et al., (1987) J. Pharm. Sci. 76, 25–28). (This phenomenon is normally associated with a destruction of the skin surface and of its protective shield and thus is undesired.) On the other hand, it has been shown that some agents can permeate through skin in the form of low-molecular weight complexes with added molecules (Green et al., (1988) Int. J. Pharm. 48, 103–111).

Methods deviating from the ones already described have brought little improvement to date. The use of lipoidal carriers, the liposomes, on intact skin, which has been theoretically discussed by several authors, was mainly aimed at modifying the agent's pharmacokinetics (Patel, Bioch. Soc. Trans., 609th Meeting, 13, 513–517, 1985, Mezei, M. Top. Pharm. Sci. (Proc. 45th Int. Congr. Pharm. Sci.F.I.P.) 345–58 Elsevier, Amsterdam, 1985). Thus far, all proposal of this kind, moreover, involved the use of standard lipid vesicles (liposomes) which cannot penetrate the skin at all or permeate through the skin very inefficiently, as is shown in this patent application. Patent applications nos. JP 61/271204 A2 [86/271204] refer to a related use of liposomes in which hydrochinonglucosidal is employed to improve the stability of the agent.

Hitherto available preparations for percutaneous use have mostly been applied under occlusion; in the case of liposomal preparations, this was even a general rule. The corresponding preparations only contained small or lipophilic substances, as well as a limited number of skin-fluidizing additives. Correspondingly, they afforded only partial control over the pharmacokinetic properties of final preparations. In an attempt to improve this situation a proposal was made (WO 87/1938 A1) to use drug-carrying lipid vesicles in combination with a gelatinizing agent as a transdermal patch. This has prolonged drug action but has not increased the skin-penetration capability of the drug itself. Through massive use of penetration enhancers (polyethylene glycol and fatty acids) and of lipid vesicles, Gesztes und Mezei (1988, Anesth. Analg. 67, 1079–1081) have succeeded in inducing local analgesia with lidocaine-containing carriers; however, the overall effectiveness of the drug in this preparation was relatively low and its effects were only observed several hours after the beginning of an occlusive application.

By a specially designed formulation we have succeeded in obtaining results which were dramatically better than those of Gesztes and Mezei. Our carrier formulations consisted of filtered lipid vesicles (liposomes) which also contained some detergents, with a declared optimum lipid/surfactant content of 1–40/1, in practice mainly around 4/1.

These results provided a basis for German patent application P 40 26 834.9-41 which also refers to German patent application P 40 26 833.0-43; the latter deals with the problem of liposome fabrication.

Since then, we have unexpectedly discovered that certain criteria, described in this application, may be formulated for the qualification of drug carriers as suitable for the penetration into and through a permeability barrier. The main requirement of such a drug carrier—which in the following is called a transfersome—is that it is sufficiently elastic to penetrate through the constrictions in a barrier, such as skin. In the case of transfersomes consisting of phosphatidylcholine and sodium cholate this condition is fulfilled when the edge tension of a carrier is below 10 Piconewton; similar values are also likely to pertain to other, related systems.

Carriers which are capable of creating a gradient after an application are particularly useful; this is due to the fact that they have a spontaneous tendency for penetration through permeability barriers.

SUMMARY OF THE INVENTION

It is, therefore, an object of the present invention to specify the properties of novel preparations which are suitable for the mediation of rapid transport of diverse agents and other substances through permeability barriers and constrictions.

A further object of this invention is to introduce a new class of carrier preparations for the transport of drugs through human, animal or plant skin, which result in a characteristic improved availability of the agent molecules at the target site.

It is yet another object of this invention to prepare formulations for non-invasive application of antidiabetics, most notably of insulin; these should ensure an improved, therapeutically sufficient, and reproducible form of drug application.

A further object of this invention is to provide procedures for the production of such preparations.

These objects have been accomplished through the features of the independent claims.

Advantageous embodiments are mentioned in the subclaims.

DETAILED DESCRIPTION OF THE INVENTION

Figure 1:
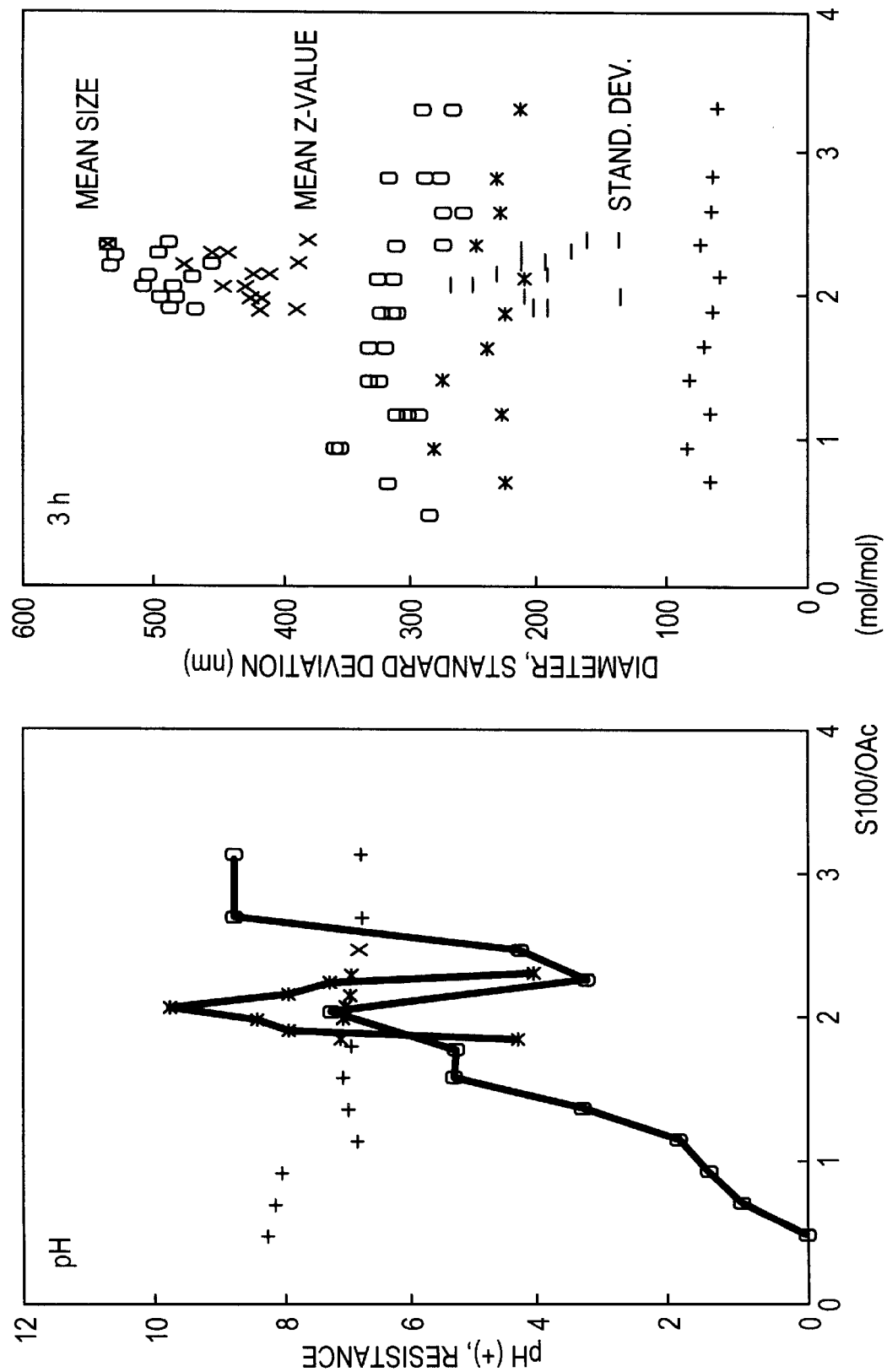
FIG. 1 is a graphical representation of the permeation resistance data and the vesicle size data described in Examples 1–13 and 14–20.

The transfersomes according to this invention differ from the liposomes hitherto described for topical application and from other related carriers in at least three basic features. Firstly, they can consist of an arbitrary amphiphile, including oils. Secondly, they can be made in arbitrary fashion: their penetration capacity does not depend on the manufacturing procedure. Thirdly, the penetration capability of the previously described liposomes optimized for applications on skin (cf. patent application P 40 26 834.9-41) was based on the use of a carrier composition with an optimal lipid/surfactant ratio in the range of L/S=1–40/1. However, a transfersome must mainly have an optimal elasticity, which ensures a sufficiently high permeation capability of such a carrier. If this basic requirement is fulfilled by the addition of edge-active substances to a basic transfersome component, the necessary total amount of the edge-active substance can correspond to L/S values below 1/500 (in the case of classical surfactants below 1/50 to 1/100). The range of concentrations suitable for making transfersomes is thus by several thousand per cent higher than previously believed.

Transfersomes also differ from micellar carrier formulations in at least two basic features. Firstly, a transfersome is, as a rule, far bigger than a micelle; consequently, it also obeys different diffusion laws. Secondly, and more importantly, a transfersome typically contains a water-filled central core (the inner lumen of a vesicle). Nearly all water soluble substances can be incorporated in the core of a transfersome and thus transported across a permeability barrier. Transfersomes are suitable for transporting amphiphilic and lipophilic substances.

If simple carriers are not sufficiently deformable and their permeation capacity must be achieved by using certain edge-active additives, the concentration of the latter is then preferably in the range between 0.1 and 99% of the quantity which would be required for carrier solubilization. Frequently, the optimum—depending on the purpose and the drug used—is located in the range between 1 and 80%, most frequently between 10 and 60% of the solubilization dose; the concentration range between 20 and 50 mol-% is the most preferred dose.

Our novel transfersomes can mediate transport of agents through essentially all permeability barriers and are suitable, for example, for percutaneous (dermal) applications of medical agents. Transfersomes can carry water- or fat-soluble agents to various depths at the application site, depending on the transfersomal composition, application dose, and form. Special properties which cause a carrier to behave as a transfersome can be realized for phospholipid vesicles as well as for other types of amphiphile aggregates.

In this application it is shown for the first time that by means of suitably formulated transfersomes, a major proportion of the drugs applied can be introduced not only into a permeability barrier, such as skin, but, moreover, can be transported into the deeper tissues where they become systemically active. Transfersomes can carry polypeptides, for example, through intact skin at an effectiveness which is a 1,000 times higher than was previously possible when using structureless penetration enhancers. Transfersomally formulated substances can reach nearly 100% of the corresponding biological or therapeutical maximum efficacy after applications on human skin. Similar effects, to date, have only been achievable by using an injection needle.

In the course of this study, it has surprisingly been found that through use of such novel drug carriers, antidiabetics can be brought into the blood through intact skin without the necessity of auxiliary measures such as an injection. After a dermal application of insulin applied in the form of transfersomes, more than 50% and often more than 90% of the applied drug dose are routinely found in the destined organs of the body. Insulin-containing, dermally applied transfersomes can thus successfully replace injections of insulin solutions.

The present invention, consequently, opens up a way for simple, noninvasive and completely painless therapy of type II diabetes: transfersomes can be used alone or in combination with an arbitrary dosing means for non-problematic therapy of acute and/or chronical diabetes.

Carriers according to this invention can consist of one or several components. Most commonly, a mixture of basic substances, one or several edge-active substances and agents is used. Lipids and other amphiphiles are best suited basic substances; surfactants or suitable solvents are the best choice from the point of view of edge-active substances. All these can be mixed with agents in certain proportions depending both on the choice of the starting substances and on their absolute concentrations. It is possible that one or several preparation components are only made edge-active by subsequent chemical or biochemical modification of a preparation (ex tempore and/or in situ).

Transfersomes thus offer an elegant, uniform and generally useful means of transport across permeability barriers for diverse agents. These newly developed carriers are perfectly suited for use in human and animal medicine, dermatology, cosmetics, biology, biotechnology, agrotechnology and other fields.

A transfersome according to this invention comprises any carrier with a special capability to get or diffuse into or through a permeability barrier under the effect of a gradient and by so doing to transport material between the application and destination sites.

A (drug) carrier of this type preferably corresponds to a molecular homo- or hetero-aggregate or to a polymer. The carrier aggregate, according to this invention, consists of a few or many, identical or different molecules; these form a physico-chemical, physical, thermodynamical and, quite frequently, functional unity. Some examples of corresponding aggregates are micelles, disk-micelles, oil-droplets (nanoemulsions), nanoparticles, vesicles or 'particulate emulsions'; parts of an aggregate can also be held together by (a) non-covalent force(s). The optimal carrier size is also a function of the barrier properties. Furthermore, it is influenced by the polarity (hydrophilicity), mobility (dynamics), and charge density as well as the elasticity of an carrier (surface). Advantageous sizes of transfersomes are in the range of 10 nm to 10,000 nm.

For dermal applications, for example, preferably particles or vesicles with a diameter of the order of 100–10,000 nm, frequently in the range of 100 to 400 nm, and most frequently with sizes between 100 and 200 nm are used as carriers.

For the use in plants, relatively small carriers, depending on the details of each individual application, should be used, most frequently with diameters below 500 nm.

DEFINITIONS

Lipids

A lipid in the sense of this invention is any substance with characteristics similar to those of fats or fatty materials. As a rule, molecules of this type possess an extended apolar region (chain, X) and, in the majority of cases, also a water-soluble, polar, hydrophilic group, the so-called headgroup (Y). The basic structural formula 1 for such substances reads $$X—Y_n \qquad (1)$$

where n is greater or equal zero. Lipids with n=0 are called apolar lipids; those with n>=1 are polar lipids. In this context, all amphiphiles, such as glycerides, glycerophospholipids, glycerophosphinolipids, glycerophosphonolipids, sulfolipids, sphingolipids, isoprenoidlipids, steroids, sterines or sterols and lipids containing carbohydrate residues, can simply be referred to as lipids.

A phospholipid, for example, is any compound of formula 2

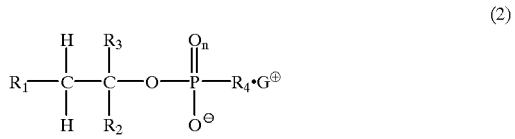

(2)

In this formula, n and $R_4$ have the same significance as in formula 8 except that $R_1$ and $R_2$ cannot be hydrogen, an OH-group or a short chain alkyl residue; R3 is a hydrogen atom or an OH-group, in the majority of cases. In addition, $R_4$ can be a short chain alkyl group substituted by three short chain alkylammonium residues, e.g. trimethylammonium, or an amino-substituted short chain alkyl, e.g. 2-trimethylammonioethyl (cholinyl).

A lipid is preferably any substance according to formula 2, in which n=1, $R_1$ and $R_2$ is hydroxyacyl, $R_3$ is a hydrogen atom and $R_4$ is a 2-trimethylammonioethyl (the last compound corresponding to the phosphatidylcholine headgroup), 2-dimethylammonioethyl, 2-methylammonioethyl or 2-aminoethyl (corresponding to a phosphatidylethanolamine headgroup).

A lipid of this kind is, for example, phosphatidylcholine from natural sources, in the old nomenclature also called lecithin. This can be obtained, for example, from eggs (then being rich in arachidic acid), soy-bean (rich in C-18 chains), coconuts (rich in saturated chains), olives (rich in monounsaturated chains), saffron, safflower and sunflowers (rich in n-6 linolenic acid), linseed (rich in n-3 linolenic acid), from whale-oil (rich in monounsaturated n-3 chains), from Nachtkerze or primrose (rich in n-3 chains), etc. Preferred natural phospsphatidylethanolamines (in the old nomenclature also called cephalins), frequently stem from egg or soy-beans.

Further preferred lipids are synthetic phosphatidylcholines ($R_4$ in formula 2 corresponding to 2-trimethylammonioethyl), synthetic phosphatidylethanolamines ($R_4$ being identical to 2-aminoethyl), synthetic phosphatidic acids ($R_4$ being a proton) or their esters ($R_4$ corresponding e.g. to a short chain alkyl, such as methyl or ethyl), synthetic phosphatidylserines ($R_4$ corresponding to an L- or D-serine), or synthetic phosphatidyl(poly)alcohols, such as phosphatidylglycerol ($R_4$ being identical to L-or D-glycerol). In this case, $R_1$ and $R_2$ are identical acyloxy residues such as lauroyl, oleoyl, linoyl, linoleoyl or arachinoyl, e.g. dilauroyl-, dimyristoyl-, dipalmitoyl-, distearoyl-, diarachinoyl-, dioleoyl-, dilinoyl-, dilinoleoyl-, or diarachinoylphosphatidylcholine or -ethanolamine, or different acyl residues, e.g. $R_1$=palmitoyl and $R_4$=oleoyl, e.g. 1-palmitoyl-2-oleoyl-3-glycerophosphocholine; or different hydroxyacyl residues, e.g. $R_1$=hydroxypalmitoyl and $R_4$=hydroxyoleoyl; or mixtures thereof, e.g. $R_1$=hydroxypalmitoyl and $R_4$=oleoyl etc. $R_1$ can also signify an alkenyl and $R_2$ identical hydroxyalkyl residues, such as tetradecylhydroxy or hexadecylhydroxy, e.g. in ditetradecyl- or dihexadecylphosphatidylcholine or -ethanolamine, $R_1$ can be an alkenyl and $R_2$ a hydroxyacyl, e.g. a plasmalogen ($R_4$=trimethylammonioethyl), or $R_1$ can be an acyl, e.g. myristoyl, or palmitoyl, and $R_2$ a hydroxy, e.g. in natural or synthetic lysophosphatidylcholines or lysophosphatidylglyceroles or lysophosphatidylethanolamines, e.g. 1-myristoyl- or 1-palmitoyllysophosphatidylcholine or -phosphatidylethanolamine; $R_3$ is frequently hydrogen.

A convenient lipid according to this invention is also a lipid of the basic formula 2, in which n=1, $R_1$ is an alkenyl residue, $R_2$ is an acylamido residue, $R_3$ is a hydrogen atom and $R_4$ is 2-trimethylammonioethyl (choline residue). A lipid of this kind is known under the term sphingomyeline.

Furthermore, suitable lipids are analogs of lysophosphatidylcholine, such as 1-lauroyl-1,3-propandiol-3-phosphorylcholine, monoglycerides, such as monoolein or monomyristin, a cerebroside, a ganglioside or a glyceride which contain no free or esterified phosphoryl- or phosphono group or a phosphino group in the position 3. One example of such glyceride is diacylglyceride or 1-alkenyl-1-hydroxy-2-acylglyceride with arbitrary acyl or alkenyl groups, the 3-hydroxy group in these then being ether-bonded to one of the mentioned carbohydrate residues, such as a galactosyl residue, for example in monogalactosylglycerol.

Lipids with desired head or chain group properties can also be prepared biochemically, using e.g. phospholipases (such as phospholipase A1, A2, B, C, and especially D), desaturases, elongases, acyl-transferases, etc., starting with any natural or synthetic precursor.

Suitable lipids, furthermore, are all lipids found in biological membranes and extractable with suitable apolar organic solvents, such as chloroform. In addition to the lipids already mentioned, this group of lipids also encompasses steroids, such as oestradiols, or sterines, such as cholesterin, beta-sitosterine, desmosterine, 7-ketocholesterin or beta-cholestanol, fat-soluble vitamins, such as retinoids, vitamins, such as vitamin A1 or A2, vitamin E, vitamin K, such as vitamin K1 or K2, or vitamin D1 or D3, etc.

Edge Active Substances

An edge active substance according to this application is any substance which is capable of inducing or increasing the carrier system's capacity to form edges, protrusions or relatively strongly curved surfaces; this property also manifests itself in the capability to induce pores in lipid structures, such as membranes, or even provoke a solubilization (lysis) in the higher concentrations ranges. More strictly speaking, all such substances are considered edge-active which exhibit a tendency to accumulate at or near the edges between the polar and apolar parts of molecules and/or near or at the edges between the polar and apolar parts of the supramolecular aggregates, thereby lowering the free energy for the formation of edges and/or strongly curved surfaces. All surfactants and many solvents as well as asymmetric, and thus amphiphatic, molecules or polymers, such as many oligo- and polycarbohydrates, oligo- and polypeptides, oligo- and polynucleotides or their derivatives also belong to this category.

The edge activity of the used 'solvents', surfactants, lipids, or agents depends on the effective relative hydrophilicity or hydrophobicity of each molecule, and can also be modified by the choice of further system components and boundary conditions in the system (temperature, salt content, pH value, etc.). Functional groups, such as double bonds in the hydrophobic part of molecules, which lower the hydrophobicity of this molecular region, increase edge activity; elongation or space-demanding substituents in the hydrophobic molecular parts, e.g. in the aromatic part, lower the edge activity of a substance. Charged or strongly polar groups in the headgroup normally increase the edge activity provided that the hydrophobic molecular part has remained the same. Direct connections between the lipophilic and/or amphiphilic system components have the reverse effect.

Solvents which are to some extent edge active only in certain concentration ranges encompass simple, especially short chain, alcohols, such as methanol, ethanol, n-propanol, 2-propen-1-ol(allylalcohol), n-butanol, 2-buten-1-ol, n-pentanol (amylalcohol), n-hexanol, n-heptanol, n-octanol and n-decanol; furthermore, iso-propanol, iso-butanol or iso-pentanol. Higher alcohols are even more potent, for example, ethandiol (ethylene glycol), 1,2-propane diol (propylene glycol), 1,3-propane diol, 1,3-butane diol, 2,3-butane diol, propane triol (glycerol), 2-butene-1,4-diol, 1,2, 4-butane triol, 1,3,4-butane triol, 1,2,3-butane triol, butane tetraol(erythritol), 2,2-bis(hydroxymethyl)1,3-propane diol (pentaerythritol), 2,4-pentadiol and other pentadiols or pentendiols, 1,2,5-pentantriol and other pentantriols or pententriols, pentantetraol, 1,2,6-hexane triol and other hexane triols, hexane tetraol and -pentaol, heptane diol, -triol, -tetraol, -pentaol and -hexaol, 1,4-butane diol-diglycidylether, etc. Short-chain, di-, tri-, tetra-, penta- and hexaoxyethylene glycols and -ethylene glycols are also suitable for the present purpose as well as cyclic alcohols, such as benzylalcohol, cyclopentanol, cyclohexanol, 3-, 4-, 5-cyclohexanol, cyclohexylalcohol, aryl-alcohols, such as phenyl-ethanol, etc.

Edge active solvents which can be used according to this invention include, furthermore, short-chain acyl-, alkyl-, alkenyl, hydroxyacyl-, alkenyloxy- as well as aryl derivatives of different acids and bases, such as acetic acid, formic acid, propionic acid, butenoic acid, pentenoic acid, etc. of many amino acids, benzoic acid, phosphoric- and sulphuric acid, of ammonia, purine, pyrimidine, etc., provided that they do not impair the chemical integrity of the carriers and the agent molecules to an inacceptable extent.

A nonionic edge active substance is any material which contains at least one, and in the majority of cases several, strongly hydrophilic groups and at least one, sometimes also several relatively hydrophobic, water insoluble residues. 'Nonionic' edge active substances can be zwitterionic or truly non-ionic.

Free of any charge and edge active are e.g. the lipoidal substances of the basic formula 3

$$R_1-((X_i-Y_j)_k-Z_l)_m-R_2 \quad (3)$$

in which X, Y and Z are different polar (hydrophilic) or apolar (hydrophobic) groups, which confer an amphiphatic character to the whole molecule. Z ist mainly a water soluble residue and i, j, k, l and m are greater or equal zero. $R_1$ and $R_2$ are two arbitrary residues; the first is mostly polar or very short; the second apolar.

The residues $R_2$ or X in such lipids often represent an acyl-, alkyl-, alkenyl-, hydroxyalkyl-, hydroxyalkenyl- or hydroxyacyl-chain with 8–24 carbon atoms. Very frequently, n-hexyl, n-heptyl, n-octyl, n-nonyl, n-decyl, n-undecyl, n-dodecyl, n-tetradecyl or n-tetradecenoyl, n-hexadecyl, n-hexadecenoyl, n-octadecyl, n-octadecenoyl and n-octadecendienyl, n-octadecentrienyl, etc. are used.

Sorbitol is one possible example of residue Z. $(X_i-Y_j)$ can be a polyene, polyoxyalkene, such as polyoxyethylene, polyalcohol, such as polyglycol, or polyether. $(X_i-Y_j)$ mainly contain 1–20 and very frequently 2–10 units, e.g. in ethylene glycol, di- and triglycol (oligoglycol) or polyethylene glycol.

In simple substances according to formula 3, the residue $R_1$ or $R_2$ is frequently an alkyl-, alkenyl-, hydroxyalkyl-, alkenylhydroxy- or hydroxyacyl-chain with 1–24 carbon atoms. Very suitable are substances such as n-dodecyl (lauryl-ether), n-tetradecyl(myristoyl-ether), n-pentadecyl (cetyl-ether), n-hexadecyl(palmitoyl-ether), n-octadecyl (stearoyl-ether), n-tetradecenoyl(myristoleoyl-ether), n-hexadecenoyl(palmito-leoyl-ether) or n-octadecenoyl (oleoyl-ether). Owing to their good availability, the following substances are, amongst others, frequently used: 4-lauryl-ether (Brij 30), 9-lauryl-ether, 10-lauryl-ether, 23-lauryl-ether (Brij 35), 2-cetyl-ether (Brij 52), 10-cetyl-ether (Brij 56), 20-cetyl-ether (Brij 58), 2-stearyl-ether (Brij 72), 10-stearyl-ether (Brij 76), 20-stearyl-ether (Brij 78), 21-stearyl-ether (Brij 721), 2-oleoyl-ether (Brij 92), 10-oleoyl-ether (Brij 96) and 20-oleoyl-ether (Brij 78), the increasing number in their names indicating an increasing headgroup length. Suitable substances of this class are marketed under the names GENAPOL, THESIT and LUBROL.

Amongst the most common nonionic surfactants of the ether-type which are suitable for the present purpose are the substances of the Myrj trademark, such as polyoxyethylene (8)-stearate (Myrj45), polyoxyethylene(20)-stearate (Myrj49), polyoxyethylene( 30)-stearate (Myrj51), polyoxyethylene(40)-stearate (Myrj52), polyoxyethylene (50)-stearate (Myrj53), polyoxyethylene(100)-stearate (Myrj59), etc. Further products of these classes are sold under the trademark Cirrasol ALN; common polyoxyethylene-alkylamides are e.g. surfactants of the trademark Atplus.

Another important special form of the nonionic edge active substance according to basic formula 3 most frequently contains a hydroxyl group in the position of residue $R_1$ and a hydrogen atom in the position of residue $R_2$, by and large. Residues X and Z are frequently an alkoxy- or alkenoxy-, in principle also a hydroxyalkyl-, hydroxyalkenyl- or hydroxy-acyl-chain with 4–100 carbon atoms. Residue Y, too, is frequently an alkoxy-, alkenoxy-, hydroxyalkyl-, hydroxyalkenyl- or hydroxyacyl-chain but one which is often branched and carries one methyl-or ethyl-side chain. Perhaps the most widely used edge active substances of this class are the surfactants which are marketed unter the trademark "Pluronic".

Further, very commonly used special forms of non-ionic edge active substances are sold under the trademark "TWEEN". The cyclic part of this substance class is frequently a sorbitol ring. Residues $R_1$, $R_2$, $R_3$ and $R_4$ are frequently of the alkoxy- or alkenoxy-, and even more commonly of the polyene-, polyoxyalkene-, such as polyoxyethylene-, polyalcohol-, such as polyglycol-, or polyether type. Some of these chains can be apolar, corresponding to e.g. an acyl-, alkyl-, alkenyl-, hydroxyalkyl-, hydroxyalkenyl- or hydroxyacyl-chain with 8–24 carbon atoms. If none of residues $R_1$, $R_2$, $R_3$ or $R_4$ is apolar, one of the side-chains of a branched chain or one of the termini must be hydrophobic.

Chains in the substances of TWEEN type are very frequently of the polyoxyethylene class. They mainly contain one terminal hydrogen atom and more rarely a methoxy group. One of the polyoxyethylene chains, however, contains a hydrophobic residue which preferably corresponds to an acyl-, alkyl-, alkenyl-, hydroxyalkyl-, hydroxyalkenyl- or hydroxyacyl-chain with 4–24, and in particular 12–18 carbon atoms.

Edge active substances which are sold under the trademark "TRITON" are also useful according to this invention.

Polyalcohol residues $R_2$ are most frequently esterified or etherified; however, in some cases they can also be bound to the hydrophobic chain through a nitrogen atom. They are very often adducts of ethyleneglycol, glycerol, erythritol, or pentaerythritol, for example 1-alkyl-, 1-alkenoyl-, 1-hydroxyalkene-glycerol, or corresponding 1,2-, or 1,3-diglycerides (for example, 1-alkyl, 2-alkyl-, 1-alkyl, 2-alkenyl-, 1-alkenyl, 2-alkyl-, 1-alkenyl, 2-alkenyl-, 1-alkenyl, 2-hydroxyalkyl-, 1-hydroxyalkyl, 2-alkenyl-, 1-alkyl, 2-hydroxyalkyl-, 1-hydroxyalkyl, 2-alkyl-, 1-alkenyl, 2-hydroxyalkene-, 1-hydroxyalkene, 3-alkenyl-, 1-alkyl, 3-alkyl-, 1-alkyl, 3-alkenyl-, 1-alkenyl, 3-alkyl-, 1-alkenyl, 3-alkenyl-, 1-alkenyl, 3-hydroxyalkyl-, 1-hydroxyalkyl, 3-alkenyl-, 1-alkyl, 3-hydroxyalkyl-, 1-hydroxyalkyl, 3-alkyl-, 1-alkenyl, 3-hydroxyalkene- or 1-hydroxyalkene, 3-alkenyl-). Glycerol can be replaced by another oligo- or polyalcohol, such as erythritol, pentantriol, hexantriol, -tetraol or -pentaol, etc., resulting in a wide variety of linkage possibilities.

Z or $R_2$, moreover, can contain one or more 1–10, preferably 1–6, most frequently 1–3 carbohydrate residues or their derivatives. 'Carbohydrate residue' in this context has the meaning as already described and is an alpha or beta and L- or D-alloside, -altroside, -fucoside, -furanoside, -galactoside, -galactopyranoside, -glucoside, -glucopyranoside, -lactopyranoside, -mannoside, -mannopyranoside, -psicoside, sorboside, -tagatoside, -taloside; frequently used derivatives of disaccharides are L- or D-maltopyranoside, -maltoside, -lactoside, malto- or -lactobionamide; the corresponding derivatives of maltotriose or -tetraose are also useful.

The carbohydrate residue can also contain a sulfur atom, e.g. in beta-L- or D-thioglucopyranoside or -thioglycoside.

Zwitterionic surfactants are substances, for example, which contain a sulphonate group, such as (3-((3-cholamidopropyl)dimethylammonio)-1-propanesulfonate (CHAPS) and (3-((3-cholamidopropyl)-dimethylammonio)-2-hydroxy-1-propanesulfonate (CHAPSO) or N-octyl-N,N-dimethyl-3-ammonio-1-propanesulfonate, N-dodecyl-N,N-dimethyl-3-ammonio-1-propanesulfonate(lauryl-sulfobetaine), N-tetradecyl-N,N-dimethyl-3-ammonio-1-propanesulfonate(myristyl-sulfobetaine), N-hexadecyl-N,N-dimethyl-3-ammonio-1-propanesulfonate(palmitylsulfobetaine), N-octadecyl-N,N-dimethyl-3-ammonio-1-propanesulfonate(stearyl-sulfobetaine), 'N-octadecenoyl-N,N,-dimethyl-3-ammonio-1-propanesulfonate(oleoyl-sulfobetaine) etc.

Zwitterionic surfactants are also substances with the basic formula 4

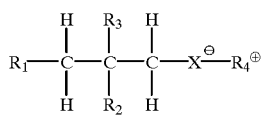
(4)

in which n is one or zero. One of both side chains $R_1$ and $R_2$ contains one acyl-, alkyl-, alkenyl-, alkenoyl-, hydroxyalkyl-, hydroxyalkenyl- or hydroxyacyl-, or alkoxy chain with 8–24 carbon atoms each; the other residue corresponds to a hydrogen, to a hydroxy group or to a short chain alkyl residue. $R_3$ normally represents a hydrogen atom or a short alkyl chain. X is most frequently anionic, e.g. in a phosphate- or sulfate-residue. The residue $R_4$ in this case is cationic, in order to ensure that the whole molecule is zwitterionic. Most frequently, ammonio-alkyl derivatives, such as ethanol-, propanol-, butanol-, pentanolamine, hexanolamine, heptanolamine or octanolamine, N-methyl-, N,N-dimethyl, or N,N,N-trimethyl-ammonio-alkyl, N-ethyl-, N,N-diethyl, or N,N,N-triethyl-amino-alkyl, unequal N-alkyles, such as N,N-methyl-ethyl-ammonio-alkyl, or corresponding hydroxyalkyl substances are used, sometimes in a substituted form. (Single chain (lyso) derivatives of all biological zwitterionic phospholipids as well as their modified forms (such as Platelet-Activating-Factor and its analogs) also belong to this category.) $R_4$ can also be a positively charged carbohydrate residue, such as an aminosugar or one of its derivatives. $R_4$ and X, moreover, can exchange positions.

An ionic edge active substance is any material which contains at least one positive or negative charge and at least one segment which is poorly water soluble. An anionic substance of this kind can also contain several charges but must have a negative total charge. The total charge of any cationic substance must be positive.

Anionic edge active substances are for example the substances described by the basic formula 5:

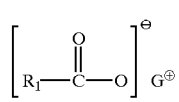
(5)

in which $R_1$ is an organic hydrocarbon residue, which can also be substituted, and $G^+$ is a monovalent counterion, chiefly an alkali metal cation (such as lithium, sodium, potassium, rubidium, or cesium), an ammonium ion or a low weight tetraalkylammonium-ion, such as tetramethylammonium or tetraethylammonium.

The hydrocarbon residue $R_1$ in an anionic surfactant of the basic formula 5 is frequently a straight chain or branched acyl, alkyl or alkenoyl, or oxidized or hydroxygenated derivative thereof; the residue $R_1$ can also contain one or several cyclic segments.

$R_1$ chain frequently contains 6–24, more frequently 10–20, and most frequently 12–18 carbon atoms; if unsaturated, it contains 1–6, and even more frequently 1–3, double bonds in n-3- or n-6-position.

The following hydroxyalkyl chains are preferred for the present purpose: n-dodecylhydroxy(hydroxylauryl), n-tetradecylhydroxy(hydroxymyristyl), n-hexadecylhydroxy(hydroxycetyl), n-octadecylhydroxy (hydroxystearyl), n-eicosylhydroxy or n-docosyloxy. Amongst the hydroxyacyl chains, the hydroxylauroyl, hydroxymyristoyl, hydroxypalmitoyl, hydroxystearoyl, eicosoylhydroxy or docosoyloxy chains are especially worth mentioning; particularly interesting amongst the hydroxyalkene-residues are the hydroxydodecen, hydroxytetradecen, hydroxyhexadecen, hydroxyoctadecen, hydroxyeicosen, hydroxydocosen, most notably 9-cis, 12-hydroxyoctadecenyl(ricinolenyl) or 9-trans, 12-hydroxy-octadecenyl(ricinelaidyl), 5-cis, 8-cis, 11-cis, 14-cis, 15-hydroxyeicosatetraenyl(15-hydroxy-arachidonyl), 5-cis, 8-cis, 11-cis, 14-cis, 15-hydroxy, 17-cis-eicosapentaenyl, 4-cis, 7-cis, 10-cis, 13-cis, 15-hydroxy, 16-cis-docosapentaenyl and 4-cis, 7-cis, 10-cis, 13-cis, 15-hydroxy, 16-cis, 19-cis-docosahexaenyl.

Another class of anionic, edge active substances corresponds to basic formula 6

(6)

here, $R_1$ is a hydrocarbon residue which can also be substituted; X is a short-chain alkyl residue and Y denotes a sulfonate-, sulfate-, phosphate-, phosphonate or phosphinate group. $G^+$ is a mostly monovalent counterion (cation).

Alkali metal alkyl- or -alkenylethersulfonates or -phosphates belong to this class of ether-bonded molecules. Special examples are sodium-or potassium-n-dodecyloxyethylsulfate, -n-tetradecyloxyethylsulfate, -n-hexadecyl-oxyethylsulfate or -n-octadecyloxyethylsulfate or an alkali metal alkane sulfonate, such as sodium- or potassium-n-hexanesulfonate, n-octansulfonate, n-decansulfonate, n-dodecansulfonate, -n-tetradecansulfonate, -n-hexadecansulfonate or -n-octadecansulfonate.

The substances of general formula 7

(7)

are related to the compounds of basic type 6. These are analogous to the substances of formula 6 but contain a directly (covalently) coupled charged headgroup.

Particularly useful anionic, edge active substances of above formula 6 are alkali metal-alkylsulfates. To mention just a few examples: sodium or potassium-n-dodecyl (lauryl)-sulfate, -n-tetradecyl(myristyl)-sulfate, -n-hexadecyl (palmityl)-sulfate, -n-octadecyl(stearyl)-sulfate, n-hexadecylen(palmitolein)-sulfate and n-octadecylen(olein)-sulfate. Instead of a sulfate group, sulfonate, n-methyl- or n-ethylglycine for example can also be used.

Various salts of bis-(2-alkyl-alkyl)-sulfosuccinate are also suitable for the applications as described in this work. Preferably, these are used as lithium-, sodium-, potassium-, or tetramethylammonium-bis-(2-ethyl-hexyl)-sulfosuccinate.

Furthermore, sarcosides, as well as alkyl- or alkenoylsulfochloride derivatives of the protein condensates, sulfonamide soaps, sulfatated or phosphorylated alcohol-esters, sulfatated or phosphorylated amides or monoglycerides, moreover, fatty acid alkylamides, sulfo- or phospho-succinic acid esters, taurides, alkylphenol-, alkylbenzol-, alkylnapthaline-ethersulfonates etc., are also all useful.

Another important group of anionic edge active substances are the derivatives of cholic acid. Their basic formula reads

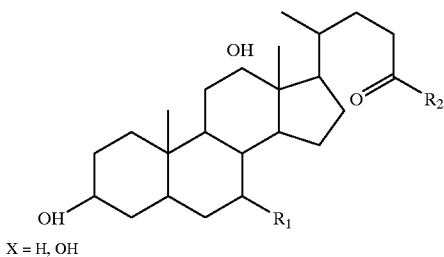

X = H, OH here, $R_1$ corresponds to a proton, an OH— or a carbonyl group and $R_2$ can be a derivative of taurine or glycocoll, for example. Particularly suitable are various salts of cholic acid (bile acid, 3alpha, 7alpha, 12alpha-trihydroxy-5beta-cholane-24-oin-acid), deoxycholic acid (3alpha, 12alpha-dihydroxy-5beta-cholane-24-oin-acid), chenodeoxycholic acid, glycocholic acid (N-(3alpha, 7alpha, 12alpha-trihydroxy-24-oxycholane-24-yl-)glycine), deoxycholic acid, glycodeoxycholic acid (N-(3alpha, 12alpha-dihydroxy-24-oxycholane-24-yl-)glycine), glycochenodeoxycholic acid, glycolitocholic acid, glycoursodeoxycholic acid, litocholic acid, taurodeoxycholic acid, taurocholic acid (3alpha, 7alpha, 12alphatrihydroxy-5beta-cholan-24-oin-acid-N-(sulfoethyl)amide), taurochenodeoxycholic acid, tauroglycocholic acid, taurolitocholic acid, taurolitocholic acid-3-sulfate, tauroursodeoxycholic acid, ursocholanic acid, ursodeoxycholic acid (3alpha, 7beta-dihydroxy-5beta-cholanic acid), the most common counterions being sodium or potassium.

Diverse cholic acid esters, such as cholesteryl-alkyl-, -alkenyl-, -hydroxyalkyl-, -hydroxyalkene-esters or cholesterylsulfates and -sulfonates are also edge active according to this invention.

Related synthetic adducts of the CHAPS class can also be used; in this case, $R_2$ is frequently an NH—$(CH_2)_3$—N', N'—$(CH_2)_2(CH_2)_2$—$R_3$—$CH_2$—$SO_3$ segment, whilst $R_3$ can be a proton or a carbonyl group. Again, sodium or potassium are the most commonly used counterions.

Digitonines as well as saponines, such as Quillaja acid, have similar basic structures in their cores as the cholic acid derivatives; consequently, they can also be used as edge active substances according to this invention.

The basic formula of the phosphorus-containing anionic edge active substances is

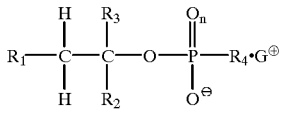 (8)

in which n is zero or one. One of the two side chains $R_1$ and $R_2$ contains hydrogen, a hydroxy group or a short chain alkyl residue; the other contains an alkyl-, alkenyl-, hydroxyalkyl-, hydroxyalkenyl- or hydroxyacyl-chain (or an alkenyl-, alkoxy-, alkenyloxy- or acyloxy-residue) with 8–24 carbon atoms. The $R_3$ residue, as a rule, corresponds to hydrogen or an alkyl chain with less than 5 carbon atoms. $R_4$ can be an anionic oxygen or a hydroxy group; an alkyl chain with up to 8 C-atoms can also appear as well as another carbohydrate residue with up to 12 carbon atoms; if $R_1$ as well as $R_2$ are hydrogen and/or hydroxy groups, a steroid residue, a sugar derivative, a chain containing an amino group, etc., can also appear. Alkyl residues can also be substituted.

Amongst the most suitable surfactants of this substance class are: n-tetradecyl(=myristoyl)-glycero-phosphatidic acid, n-hexadecyl-(=plamityl)-glycero-phosphatidic acid, n-octadecyl(=stearyl)-glycero-phosphatidic acid, n-hexadecylene(=palmitoleil)-glycero-phosphatidic acid, n-octadecylene(=oleil)-glycero-phosphatidic acid, n-tetradecyl-glycero, phosphoglycerol, n-hexadecyl-glycero-phosphoglycerol, n-octadecylene-glycero-phosphoglycerol, n-tetradecyl-glycero-phosphoserine, n-hexadecyl-glycerophosphoserine, -n-octadecyl-glycero-phosphoserine, n-hexadecylene-glycero-phosphoserine and n-octadecylene-glycero-phosphoserine.

The corresponding lyso-sulfolipids, phosphono- or phosphino-lipids are also suitable edge active compounds according to this invention.

Counterion in these compounds is most frequently an alkali metal cation (such as lithium, sodium, potassium, cesium) or a water soluble tetraalkylammonium-ion (such as tetramethylammonium, tetrathylammonium, etc.).

All corresponding statements made above for surfactants of basic formula 3 also pertain to the carbohydrate residue $R_1$.

This residue in the majority of cases is a straight chain or branched alkyl or alkenoyl chain with 6–24, very frequently 10–20, in particular 12–18, carbon atoms and 1–6, especially frequently 1–3, double bonds in n-3- or n-6- positions.

Very convenient alkyl-residues $R_1$ or $R_2$ are, for example, n-dodecyl, n-tetradecyl, n-hexadecyl, n-octadecyl, n-eicosyl or n-docosyl chains. N-nonyl, n-undecyl, n-tridecyl, n-pentadecyl, n-heptadecyl and n-nonadecyl, however, are equally useful.

An alkenyl in position $R_1$ or $R_2$ is preferably a 9-cis-dodecenyl(lauroleyl), 9-cis-tetradecenyl(myristoleyl), 9-cis-hexadecenyl(palmitoleoyl), 6-cis-octadecenyl(petroselinyl), 6-trans-octadecenyl(petroselaidinyl), 9-cis-octadecenyl (oleyl), 9-trans-octadecenyl(elaidinyl), 11-cis-octadecenyl (vaccenyl), 9-cis-eicosenyl(gadoleinyl), 13-cis-docosenyl, 13-trans-docosenyl or 15-cis-tetracosenyl, etc.

Higher unsaturated alkenyls which also can be used for the present purpose are, amongst others: 9-cis, 12-cis-octadecendienyl, 9-trans, 12-trans-octadecendienyl, 9-cis, 12-cis, 15-cis-octadecentrienyl, 6-cis, 9-cis, 12-cis-octadecentrienyl, 11-cis, 14-cis, 17-cis-eicosatrienyl, 6-cis, 9-cis, 12-cis, 15-cis-octadecentetraenyl, 5-cis, 8-cis, 11-cis, 14-cis-eicosatetraenyl, 5-cis, 8-cis, 11-cis, 14-cis, 17-cis-eicosapentaenyl, 4-cis, 7-cis, 10-cis, 13-cis, 16-cis-docosapentaenyl and 4-cis, 7-cis, 10-cis, 13-cis, 16-cis, 19-cis-docosahexaenyl.

$R_1$ and $R_2$ are preferably chosen from the substances of the hydroxyalkyl-class, in which case they correspond, for example, to n-decylhydroxy, n-dodecylhydroxy (hydroxylauryl), n-tetradecylhydroxy(hydroxymyristyl), n-hexadecylhydroxy(hydroxycetyl), n-octadecylhydroxy (hydroxystearyl) and n-eicosylhydroxy(hydroxyarachinyl) chains.

An alkenylhydroxy in $R_1$ or $R_2$ is preferably a 9-cis-dodecenylhydroxy(hydroxylauroleyl), 9-cis-tetradecenylhydroxy(hydroxymyristoleyl), 9-cis-hexadecenylhydroxy(hydroxypalmitoleinyl), 6-cis-octadecenylhydroxy(petroselinylhydroxy), 6-trans-octadecenylhydroxy(hydroxypetroselaidinyl), 9-cis-octadecenylhydroxy(hydroxyoleyl), 9-trans-octadecenylhydroxy(hydroxyelaidinyl) and 9-cis-eicosenyl (hydroxygadoleinyl) chain.

An alkanoylhydroxy in $R_1$ or $R_2$ is preferably an n-decanoylhydroxy, n-dodecanoylhydroxy (lauroylhydroxy), n-tetradecanoylhydroxy (myristoylhydroxy), n-hexadecanoylhydroxy, n-hexadecanoylhydroxy(palmitoylhydroxy), n-octadecanoylhydroxy(stearoylhydroxy) and n-eicosoylhydroxy(arachinoylhydroxy) chain.

An alkenoylhydroxy in $R_1$ or $R_2$ is preferably a 9-cis-dodecenylhydroxy(lauroleoylhydroxy), 9-cis-tetradecenoylhydroxy(myristoleoylhydroxy), 9-cis-hexadecenoylhydroxy(palmitoleinoylhydroxy), 6-cis-octadecenoylhydroxy(peteroselinoylhydroxy), 6-trans-octadecenoylhydroxy(petroselaidinoylhydroxy), 9-cis-octadecenoylhydroxy(oleoylhydroxy), 9-trans-octadecenoylhydroxy(elaidinoylhydroxy) and 9-cis-eicosenoyl(gadoleinoylhydroxy) chain.

Some examples for the short chain alkyl residue, which often appear in the $R_4$ residue, are methylene-, ethylene-, n-propylene-, iso-propylene-, n-butylene- or iso-butylene- as well as n-pentylene- or n-hexylene-groups. $R_4$ can also be a carboxy- or a sulfo-group, an acid or alkaline group, such as carboxy- and amino-group; the amino group in such case is always in the alpha-position relative to the carboxy group.

Another example for the $R_4$ residue are free or etherified hydroxy groups (two ether-bonded hydroxy groups, in such case, can be connected by one divalent hydrocarbon residue, such as methylene, ethylene, ethylidene, 1,2-propylene or 2,2-propylene). $R_4$, furthermore, can be substituted by a halogen atom, such as chlorine or bromine, a low weight alkoxycarbonyl, such as methoxy- or ethoxycarbonyl, or by a low weight alkansulfonyl-, such as methansulfonyl.

A substituted short chain alkyl residue $R_4$ with 1–7 C-atoms is preferably carboxy-short-chain alkyl, such as carboxy-methyl, carboxyethyl- or 3-carboxy-n-propyl, omega-amino-n-carboxy- a short-chain alkyl, such as 2-amino-2-carboxyethyl or 3-amino-3-carboxy-n-propyl, hydroxy-short-chain alkyl, such as 2-hydroxyethyl or 2,3-dihydroxypropyl, a short-chain alkoxy-3-methoxy-n-propyl, a short-chain alkylendioxy-short-chain alkyl, such as 2,3-ethylenedioxypropyl or 2,3-(2,2-propylene)dioxypropyl, or halogen-short-chain alkyl, such as chloro- or bromo-methyl, 2-chloro- or 2-bromo-ethyl, 2- or 3-chloro- or 2- or 3-bromo-n-propyl.

A carbohydrate residue $R_4$ with 5–12 C-atoms is, for example, a natural monosaccharide residue stemming from a pentose or a hexose in the aldose or ketose form.

A carbohydrate residue $R_4$, moreover, can be a natural disaccharide residue, such as a disaccharide residue formed from two hexoses, in the described sense. A carbohydrate residue $R_4$ can also be a derivatised mono-, di- or oligosaccharide residue, in which an aldehyde group and/or one or two terminal hydroxy groups are oxidized to a carboxy group, e.g. a D-glucon-, D-glucar- or D-glucoron acid residue; this preferably appears in the form of a cyclic lactone residue. The aldehyde- or keto-groups in a derivatised mono- or disaccharide residue can also be reduced to a hydroxy group, e.g. in inositol, sorbitol or D-mannitol; also, one or several hydroxy groups can be replaced by a hydrogen atom, e.g. in desoxysugars, such as 2-desoxy-D-ribose, L-rhamnose or L-fucose, or by an amino group, e.g. in aminosugars, such as D-glucosamine or D-galactosamine.

$R_4$ can also be a steroid residue or a sterine residue. If $R_4$ is a steroid residue, $R_3$ is a hydrogen atom, whilst $R_1$ and $R_2$ in such case preferably correspond to a hydroxy group.

The counterion in such cases is preferably an ammonium, sodium or potassium ion.

In an anionic surfactant of formula 8, the following values of parameters are preferred: n=1, $R_1$ is an alkyl, such as n-dodecyl(lauryl), n-tridecyl, n-tetradecyl(myristyl), n-pentadecyl, n-hexadecyl(cetyl), n-heptadecyl or n-octadecyl(stearyl), hydroxyalkyl, such as n-dodecylhydroxy(hydroxylauryl), n-tetradecylhydroxy (hydroxymyristyl), n-hexadecylhydroxy(hydroxycetyl), or n-octadecylhydroxy(hydroxystearyl), hydroxyacyl, such as hydroxylauroyl, hydroxymyristoyl, hydroxypalmitoyl or hydroxystearoyl, $R_2$ is a hydrogen atom or a hydroxy group, $R_3$ is a hydrogen atom or a short-chain alkyl, such as methyl, $R_4$ is a short-chain alkyl, e.g. methyl or ethyl, short-chain alkyl substituted by an acid or an alkaline group, such as a carboxy and amino group, e.g. omega-amino-omega-carboxy-short-chain alkyl, such as 2-amino-2-carboxyethyl or 3-amino-3-carboxy-n-propyl, hydroxy- short-chain alkyl, such as 2-hydroxyethyl or 2,3-hydroxypropyl, short-chain alkylenedioxy-short-chain alkyl, e.g. 2,3-ethylenedioxypropyl or 2,3-(2,2-propylene)dioxypropyl, halogen-short-chain alkyl, such as 2-chloro- or 2-bromo-ethyl group, a carbohydrate residue with 5–12 C-atoms, e.g. in inositol, or a steroid residue, such as a sterol, e.g. cholesterin, and $G^+$ is a sodium-, potassium- or ammonium-ion.

An anionic surfactant of formula 8, in many cases, is a sodium- or potassium salt of lysophosphatidylserine, such as the sodium- or potassium salt of lysophosphatidylserine from bovine brain or the sodium- or potassium salt of a synthetic lysophosphatidylserine, such as sodium- or potassium-1-myristoyl- or -1-palmitoyl-lysophosphatidylserine, or a sodium- or potassium salt of lysophosphatidylglycerols. The hydrogen atom on the phosphate group can be replaced by a second cation, $G^+$ or calcium-, magnesium-, manganese-ion, etc.

An anionic surfactant of formula 8 preferably contains an alkyl chain, such as n-dodecyl(lauryl), n-tridecyl, n-tetradecyl(myristoyl), n-pentacedyl, n-hexadecyl(cetyl), n-heptadecyl or n-octadecyl(stearyl), a hydroxyalkyl chain, such as n-dodecylhydroxy(hydroxylauryl), n-tetradecylhydroxy(hydroxymyristyl), n-hexadecylhydroxy(hydroxycetyl), or n-octadecylhydroxy (hydroxystearyl), a hydroxyacyl chain, such as hydroxylauroyl, hydroxymyristoyl, hydroxypalmitoyl or hydroxystearoyl in position $R_1$, a hydrogen atom or a hydroxy group in position $R_2$, and a hydrogen atom or a short-chain alkyl, such as methyl group, in position $R_3$. $G^+$ is preferably an ammonium, sodium, potassium or tetramethylammonium ion.

An anionic surfactant of formula 8 can, furthermore, be a sodium- or potassium salt of a natural phosphatidic acid, such as egg-phosphatidic acid, a sodium- or potassium salt of a natural lysophosphatidic acid, such as egg-lysophosphatidic acid, a sodium- or potassium salt of a synthetic lysophosphatidic acid, such as 1-lauroyl-, 1-myristoyl-, 1-palmitoyl- or 1-oleoyl-lysophosphatidic acid, etc.

The most important classes of cationic surfactants encompass: ammonium salts, quarternary ammonium salts, salts of heterocyclic bases, such as alkylpyridium-, imidazole-, or imidazolinium salts, salts of alkylamides and polyamines, salts of acylated diamines and polyamines, salts of acylated alkanolamines, salts of alkanolamine esters and ethers, etc.

A cationic surfactant is, for example, any substance corresponding to the formula:

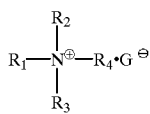

(9)

in which $R_1$ is a hydrocarbon residue which can also be substituted. $R_2$ denotes a short-chain alkyl, phenyl-short-chain-alkyl or hydrogen atom. $R_3$ and $R_4$ correspond to a short-chain alkyl residue. $R_2$ and $R_3$, together with the nitrogen atom, represent an aliphatic heterocycle, which can also be substituted on a carbon atom; $R_4$ is a short-chain alkyl; $R_2$, $R_3$ and $R_4$, together with the nitrogen atom, can also form an aromatic heterocycle, which, moreover, can be substituted on one of the carbon atoms. $G^-$ corresponds to an anion.

In a cationic surfactant of basic formula 9, $R_1$ represents an aliphatic hydrocarbon residue, which can also be substituted, for example, by an aryloxy- short-chain-alkoxy-, a substituted short-chain alkyl, a straight chain or branched chain alkyl with 7–22, and in particular 12–20, carbon atoms, or an alkenyl with 8–20, or in particular 12–20, carbon atoms and 1–4 double bonds.

Particularly preferred for use are straight chain alkyles with an even number of 12–22 carbon atoms, such as n-dodecyl, n-tetradecyl, n-hexadecyl, n-octadecyl, n-eicosyl or n-docosyl.

An alkenyl with 8–24, in particular 12–22, carbon atoms and 0–5, in particular 1–3, double bonds is e.g. 1-octenyl, 1-nonenyl, 1-decenyl, 1-undecenyl, 1-dodecenyl, 9-cis-dodecenyl(lauroleyl), 1-tridecenyl, 1-tetradecenyl, 9-cis-tetradecenyl(myristoleyl), 1-pentadecenyl, 1-hexadecenyl, 9-cis-hexadecenyl(palmitoleinyl), 1-heptadecenyl, 1-octadecenyl, 6-cis-octadecenyl(petroselinyl), 6-trans-octadecenyl(petroselaidinyl), 9-cis-octadecenyl(oleyl), 9-trans-octadecenyl(elaidinyl), 9-cis-12-cis-octadecadienyl (linoleyl), 9-cis-11-trans-13-trans-octadecatrienyl(alpha-elaostearinyl), 9-trans-11-trans-13-trans-octadecatrienyl (beta-elaostearinyl), 9-cis-12-15-cis-octadecatrienyl (linolenyl), 9-, 11-, 13-, 15-octadecatetraenyl(parinaryl), 1-nonadecenyl, 1-eicosenyl, 9-cis-eicosenyl(gadoleinyl), 5-, 11-, 14-eicosatrienyl or 5-, 8-, 11-, 14-eicosatetraenyl (arachidonyl).

Preferred alkenyls contain 12–20 carbon atoms and one double bond, e.g. 9-cis-dodecenyl(lauroleyl), 9-cis-tetradecenyl(myristoleyl), 9-cis-hexadecenyl (palmitoleinyl), 6-cis-octadecenyl(petroselinyl), 6-trans-octadecenyl(petroselaidinyl), 9-cis-octadecenyl(oleyl), 9-trans-octadecenyl(elaidinyl) or 9-cis-eicosenyl (gadoleinyl).

Methyl or ethyl are two examples of short-chain alkyl residues $R_2$, $R_3$ or $R_4$ which appear in substances of formula 9.

Two examples of phenyl-short-chain-alkyl groups in $R_2$ are benzyl or 2-phenylethyl.

An aliphatic heterocycle, which can form from $R_2$ and $R_3$ together with the nitrogen atom is, for example, a monocyclic, five- or six-member aza-, oxaaza- or thiazacyclyl residue, as in piperidino, morpholino or thiamorpholino groups.

Substituents of this heterocycle are the substituents $R_1$ and $R_4$ on the nitrogen as well as, in some cases, on the carbon atom; they are, most frequently, of the short-chain alkyl, such as methyl, ethyl, n-propyl or n-butyl type.

A heterocycle, which is formed from $R_2$ and $R_3$ together with nitrogen and is substituted on a carbon atom through a short-chain alkyl, is e.g. of the 2-, 3- or 4-methylpiperidinio, 2-, 3- or 4-ethylpiperidinio or 2- or 3-methylmorpholinio type.

An aromatic heterocycle, formed from $R_2$, $R_3$ and $R_4$ together with the nitrogen atom, is, for example, a monocyclic five- or six-member aza-, diaza-, oxaaza- or thiazacyclyl residue, such as pyridinio, imidazolinio, oxazolinio or thiazolinio or, for example, a benzocondensed monoazabicyclyl residue, such as chinolinio or iso-chinolinio group.

Substituents of such heterocycles are the residue $R_1$ on the nitrogen atom as well as a short-chain alkyl, such as methyl or ethyl, hydroxy-short-chain alkyl, such as hydroxymethyl or 2-hydroxyethyl, oxo-, hydroxy- or halogen, such as chloro- or bromo-compounds, which can also be substituted on a carbon atom.

A heterocycle, formed from $R_2$, $R_3$ and $R_4$ and substituted on a carbon atom through the mentioned residues is, for example, a 2- or 4-short-chain-alkylpyridinio, e.g. 2- or 4-methyl or 2- or 4-ethylpyridinio, di-short-chain-alkylpyridinio, e.g. 2,6 -dimethyl-, 2-methyl-3-ethyl-, 2-methyl-4-ethyl-, 2-methyl-5-ethyl-, or 2-methyl-6-ethylpyridinio, 2-, 3-or 4-halogenpyridinio, e.g. 2-, 3- or 4-chloropyridinio or 2-, 3- or 4-bromo-pyridinio, 2-short-chain alkylimidazolinio, -oxazolinio or -thiazolinio, such as 2-methyl- or 2-ethylimidazolinio, -oxazolinio or -thiazolinio or 2-short-chain alkyl-8-halogenchinolinio, such as 2-methyl-8-chlorochinolinio group.

A cationic surfactant of formula 9 is preferably an N-benzyl-N,N-dimethyl-N-2-(2-(4-(1,1,3,3-tetramethylbutyl)-phenhydroxy)-ethhydroxy)-ethylammoniochloride, N-benzyl-N,N-dimethyl-N-2-(2-(3(methyl-4-(1,1,3,3-tetramethylbutyl)-phenhydroxy)-ethhydroxy)-ethylammoniochloride (methylbenzethoniumchloride), n-dodecyltrimethylammoniochloride or -bromide, trimethyl-n-tetradecylammoniochloride or -bromide, n-hexadecyltrimethylammoniochloride or -bromide (cetyltrimethyl-ammoniumchloride or -bromide), trimethyl-n-octadecylammoniochloride or -bromide, ethyl-n-dodecyl-dimethylammoniochloride or -bromide, ethyldimethyl-n-tetradecylammoniochloride or -bromide, ethyl-n-hexadecyldimethylammoniochloride or -bromide, ethyldimethyl-n-octadecylammoniochloride or -bromide, n-alkyl-benzyl-dimethyl-ammoniochloride or -bromid (benzalkoniumchloride or -bromide), such as benzyl-n-dodecyldimethylammoniochloride or bromide, benzyldimethyl-n-tetradecylammoniochloride or -bromide, benzyl-n-hexadecyldimethyl-ammoniochloride or -bromide or benzyldimethyl-n-octadecylammonio-chloride or -bromide, N-(n-decyl)-pyridiniochloride or -bromide, N-(n-dodecyl)-pyridiniochloride or -bromide, N-(n-tetradeyl)-pyridiniochloride or -bromide, N-(n-hexadecyl)-pyridiniochloride or -bromide(cetylpyridiniumchloride) or N-(n-octadecyl)-pyridinio-chloride or -bromide. Mixtures of these or other edge active substances are also suitable.

The following surfactants are especially useful for biological purposes: N,N-bis(3-D-glucon-amidopropyl) cholamide (BigCHAP), Bis(2-ethylhexyl)sodium-sulfosuccinate, cetyl-trimethyl-ammonium-bromide, 3-((cholamidopropyl)-dimethylammonio)-2-hydroxy-1-propane sulfonate (CHAPSO), 3-((cholamidopropyl)-dimethylammonio)-1-propane sulfonate (CHAPS), cholate-sodium salt, decaoxyethylene-dodecyl-ether (Genapol C-100), decaethylene-isotridecyl-ether (Genapol X-100), decanoyl-N-methyl-glucamide (MEGA-10), decyl-glucoside, decyl-maltoside, 3-(decyldimethylammonio)-propane-sulfonate (Zwittergent 3–10), deoxy-bigCHAP, deoxycholate, sodium salt, digitonin, 3-(dodecyldimethylammonio)-propane-sulfonate (Zwittergent 3–12), dodecyl-dimethyl-amine-oxide (EMPIGEN), dodecylmaltoside, dodecylsulfate, glycocholate, sodium salt, glycodeoxycholate, sodium salt, heptaethylene-glycol-octyl-phenylether (triton X-114), heptyl-glucoside, heptyl-thioglucoside, 3-(hexadecyldimethylammonio)-propane-sulfonate (Zwittergent 3–14), hexyl-glucoside, dodecyl-dimethyl-amine-oxide (Genaminox KC), N-dodecyl-N,N-dimethylglycine (Empigen BB), N-decyl-sulfobetaine (Zwittergent 3–10), N-dodecyl-sulfobetaine (Zwittergent 3–12), N-hexadecyl-sulfobetaine (Zwittergent 3–16), N-tetradecyl-sulfobetaine (Zwittergent 3–14), N-octylsulfobetaine (Zwittergent 3-08), nonaethylene-glycol-monododecyl-ether (THESIT), nonaethylene-glycol-octyl-phenol-ether (triton X-100), nonaethylene-glycol-octyl-phenyl-ether (NP-40, Nonidet P-40), nonaethylene-dodecyl-ether, nonanoyl-N-methylglucamide (MEGA-9), nonaoxyethylene-dodecyl-ether (Lubrol PX, Thesit), nonyl-glucoside, octaethylene-glycol-isotridecylether (Genapol X-080), octaethylene-dodecyl-ether, octanoyl-N-methyl-glucamide (MEGA-8), 3-(octyldimethylammonio)-propanesulfonate (Zwittergent 3-08), octyl-glucoside, octylthioglucoside, entadecaethylene-isotridecyl-ether (Genapol X-150), polyethylene-polypropylene-glycol (Pluronic F-127), polyoxyethylene-sorbitane-monolaurate (Tween 20), polyoxyethylene-sorbitane-monooleate (Tween 80), taurodeoxycholate-sodium salt, taurocholate-sodium salt, 3-(tetradecyldimethylammonio)-propane-sulfonate (Zwittergent 3–14), etc.

Particularly suitable for pharmacological purposes are: cetyl-trimethyl-ammonium-salts (such as hexadecyltrimethylammoniumbromide, trimethylhexadecylaminebromo-salt), cetylsulfate salts (such as Na-salt, Lanette E), cholate salts (such as Na- and ammonium-form) decaoxyethylenedodecyl-ether (Genapol C-100), deoxycholate salts, dodecyldimethyl-amine-oxide (Genaminox KC, EMPIGEN), N-dodecyl-N,N-dimethylglycine (Empigen BB), 3-(hexadecyldimethylammonio)propane-sulfonate (Zwittergent 3–14), fatty acid salts and fatty alcohols, glycodeoxycholate salts, laurylsulfate salts (sodium dodecylsulfate, Duponol C, SDS, Texapon K12), N-hexadecyl-sulfobetaine (Zwittergent 3–16), nonaethylene-glycol-octyl-phenyl-ether (NP-40, Nonidet P-40), nonaethylene-dodecyl-ether, octaethylene-glycol-isotridecyl-ether (Genapol X-080), octaethylene-dodecyl-ether, polyethylene glycol-20-sorbitane-monolaurate (Tween 20), polyethylene glycol-20-sorbitane-monostearate (Tween 60), polyethylene glycol-20-sorbitane-monooleate (Tween 80), polyhydroxyethylenecetylstearylether (Cetomacrogo, Cremophor 0, Eumulgin, C 1000) polyhydroxyethylene-4-laurylether (Brij 30), polyhydroxyethylene-23-laurylether (Brij 35), polyhydroxyethylene-8-stearate (Myrj 45, Cremophor AP), polyhydroxyethylene-40-stearate (Myrj 52), polyhydroxyethylene-100-stearate (Myrj 59), polyethoxylated castor oil 40 (Cremophor EL), polyethoxylated hydrogenated castor oil (Cremophor RH 40, Cremophor RH 60) polyethoxylated plant oils (Lebrafils), sorbitane-monolaurate (Arlacel 20, Span 20), taurodeoxycholate salts, taurocholate salts, polyethylene glycol-20-sorbitane-palmitate (Tween 40), Myrj 49 and polyethylene glycol derivatives of ricinols, etc.

Agents:

Transfersomes as described in this invention are suitable for the application of many different agents and, in particular, for therapeutic purposes, for example. The preparations according to this invention can contain the following:

at least one adrenocorticostatic agent, in particular metyrapon;

at least one carrier substance, additive or agent, belonging to the class of beta-adrenolytics (beta blocking agents), very frequently acetobol, alprenolol, bisoprololfumarate, bupranolol, carazolol, celiprolol, mepindolsulfate, metipranolol, metoprolotartat, nadolol, oxyprenolol, pindolol, sotalol, tertatolol, timolohydrogen maleate and toliprolol, especially preferred, atenolol or propranolol;

at least one carrier substance, additive or agent, belonging to the androgenes or antiandrogenes, in particular drostanolonpropionate, mesterolon, testosteronundecanoate, testolacton, yohimbine, or chloroamidinonacetate, cyproteronacetate, ethinylestradiol or flutamide;

at least one carrier substance, additive or agent with an antiparasitic action, frequently phanquinone, benzyobenzoate, bephenium-hydroxy-naphthoate, crotamitone, diethylcarbamazine, levamisol, lindane, malathione, mesulfene (2,7-dimethylantren), metronidazol or tetramisol;

at least one anabolic agent, in particular clostebolacetate, cyanocobolamine, folic acid, mestanolone, metandienone, metenolone, nandrolone, nandrolondecanoate, nandrolone-hexyloxyphenylpropionate, nandrolon-phenylpropionate, norethandrolone, oxaboloncipionate, piridoxine or stanozolole;

at least one agent which can induce systemic anesthesia or analgesia, e.g. chlorobutanol, ketamine, oxetacaine, propanidide and thiamylal, aminophenol-derivatives, aminophenazol-derivatives, antranilic acid- and aryl-propione acid derivatives, azapropazone, bumadizone, chloroquin- and codeine-derivatives, diclophenac, fentanil, ibuprofen, indometacine, ketoprofen, methadone-substances, morazone, morphine and its derivatives, nifenazone, niflumin acid, pentazozine, pethidine, phenazopyridine, phenylbutazone-derivatives (such as 3,5 pyrazolidine dion), pherazone, piroxicam, propoxyphene, propyphenazon, pyrazol- and phenazone-derivatives (aminophenazone, metamizole, monophenylbutazone, oxyphenebutazone, phenylbutazone or phenazonesalyzilate), salicylic acid-derivatives, sulfasalazine, tilidine; acetylsalicylic acid, ethylmorphine, alclofenac, alphaprodine, aminophenazone, anileridine, azapropazone, benfotiamine, benorilate, benzydamine, cetobemidone, chlorophenesincarbamate, chlorothenoxazine, codeine, dextromoramide, dextro-propoxyphene, ethoheptazine, fentanyl, fenyramidol, fursultiamine, flupirtinmaleate, glafenine, hydromorphone, lactylphenetidine, levorphanol, mefenamic acid, meptazonol, methadone, mofebutazone, nalbufine, Na-salt of noramidopyrinium-methanesulfonate, nefopam, normethadone, oxycodone, paracetamol, pentazocine, pethidine, phenacetine, phenazocine, phenoperidine, pholcodine, piperylone, piritramide, procaine, propyphenazone, salicylamide, thebacone, tiemonium-odide, tramadone;

at least one substance from the class of analeptics, such as aminophenazole, bemegride, caffeine, doxapram, ephedrine, prolintane, or nialamide and tranylcypromine; but also vitamins, plant extracts from semen colae, camphor, menthol;

at least one substance from the class of antiallergics: e.g. agents from the globuline family, corticoids or antihistaminics (such as beclometasone-, betametasonecortisone-, dexametasone-derivatives, etc.) as well as bamipinacetate, buclizine, clemastine, clemizole, cromoglicinic acid, cyproheptadine, diflucorolonvalerate, dimetotiazine, diphenhydramine, diphenylpyraline, ephedrine, fluocinolane, histapyrrodine, isothipendyle, methadilazine, oxomemazine, paramethasone, prednilidene, theophilline, tolpropamine tritoqualine, etc. are used; amongst the preferred agents in this class are the substances characterized by their capacity to interfere (stimulate or suppress) the production of immunologically active substances, such as interleukines, interferones, leucotrienes, prostaglandines, etc. Amongst others, certain lipids and lipoids, such as phosphatidylcholines and diacylglycerols, or fatty acids and their esters, with chains containing several, preferably 3–6, most very frequently 3 or 4, double bonds, preferably of the n-3 type, are used for this purpose; the latter may also be hydroxygenated, branched or (partially) derivatized into ring structures.

at least one substance with antiarrhythmic action, such as most of the cardiacs and beta-blockers, ajmaline, bupranolol, chinidine, digoxine derivatives, diltiazem, disopyramidedihydrogensulfate, erythromycine, disopyramide, gallopamil, ipratropiumbromide, lanatoside, lidocaine, lorcainide, orciprenalinesulfate, procaine amide, propafenone, sparteinesulfate, verapamil, toliprolol.

an antiarteriosclerotic, such as clofibrate.

at least one substance belonging to the antiasthmatics and/or bronchospasmolytics, such as amiodarone, carbuterol, fenoterol, orciprenalin, sotalol, or theophilline-derivatives, as well as corticoids (such as beclomethasone, dexamethasone, hydrocortisone, prednisolone), frequently in combination with purines;

at least one substance from the class of antibiotics, such as actinomycine, alamethicine, alexidine, 6-aminopenicillanic acid, moxicilline, amphotericine, ampicilline, anisomycine, antiamoebine, antimycine, aphidicoline, azidamfenicol, azidocilline, bacitracine, beclomethasone, benzathine, benzylpenicilline, bleomycine, bleomycine sulfate, calcium ionophor A23187, capreomycine, carbenicilline, cefacetril, cefaclor, cefamandole nafate, cefazoline, cefalexine, cefaloglycine, cefaloridine, cefalotine, cefapirine, cefazoline, cefoperazone, ceftriaxone, cefuroxim, cephalexine, cephaloglycine, cephalothine, cephapirine, cerulenine, chloroamphenicol, chlorotetracycline, chloroamphenicol diacetate, ciclaciline, clindamycine, chloromadinone acetate, chlorpheniramine, chromomycine A3, cinnarizine, ciprofloxacine, clotrimazole, cloxacilline, colistine methanesulfonate, cycloserine, deacetylanisomycine, demeclocycline, 4,4'-diaminodiphenyl sulfone, diaveridine, dicloxacilline, dihydrostreptomycine, dipyridamol, doxorubicine, doxycycline, epicilline, erythromycine, erythromycinestolate, erythromycinethylsuccinate, erythromycine stearate, ethambutol, flucloxacilline, fluocinolone acetonide, 5-fluorocytosine, filipine, formycine, fumaramidomycine, furaltadone, fusidic acid, geneticine, gentamycine, gentamycine sulfate, gliotoxine, gfamicidine, griseofulvine, helvolic acid, hemolysine, hetacillin, kasugamycine, kanamycine (A), lasalocide, lincomycine, magnesidine, melphalane, metacycline, meticilline, mevinoline, micamycine, mithramycine, mithramycine A, mithramycine complex, mitomycine, minocycline, mycophenolic acid, myxothiazol, natamycine, nafcilline, neomycine, neomycine sulfate, 5-nitro-2-furaldehydesemicarbazone, novobiocine, nystatine, oleandomycine, oleandomycine phosphate, oxacihine, oxytetracycline, paromomycine, penicilline, pecilocine, pheneticilline, phenoxymethylpenicilline, phenyl aminosalicylate, phleomycine, pivampicilline, polymyxine B, propicilline, puromycine, puromycine aminonucleoside, puromycine aminonucleoside 5'-monophosphate, pyridinol carbamate, rolitetracycline, rifampicine, rifamycine B, rifamycine SV, spectinomycine, spiramycine, streptomycine, streptomycine sulfate, sulfabenzamide, sulfadimethoxine, sulfamethizol, sulfamethoxazol, tetracycline, thiamphenicol, tobramycine, troleandomycine, tunicamycine, tunicamycine A1-homologs, tunicamycine A2-homolog, valinomycine, vancomycine, vineomycine A1, virginiamycine M1, viomycine, xylostasine;

at least one substance with an antidepressive or antipsychotic action, such as diverse monoaminoxidase-suppressors, tri- and tetracyclic antidepressives, etc. Very frequently used agents of this class are alprazolame, amitriptyline, chloropromazine, clomipramine, desipramine, dibenzepine, dimetacrine, dosulepine, doxepine, fluvoxaminhydrogenmaleate, imipramine, isocarboxazide, lofepramine, maprotiline, melitracene, mianserine, nialamide, noxiptiline, nomifensine, nortriptyline, opipramol, oxypertine, oxytriptane, phenelzine, protriptyline, sulpiride, tranylcypromine, trosadone, tryptophane, vitoxazine, etc.

at least one antidiabetic agent, such as acetohexamide, buformine, carbutamide, chloropropamide, glibenclamide, glibornuride, glymidine, metformine, phenformine, tolazamide, tolbutamide;

at least one substance acting as an antidote, for example, against the heavy metal poisoning, poisoning with insecticides, against drugs, blood poisons, etc. A few examples are different chelators, amiphenazol obidoxim-chloride, D-penicillamine, tiopromine, etc.;

at least one substance from the class of antiemetics: some of such suitable agents are alizapride, benzquinamide, betahistidine-derivatives, cyclizine, difenidol, dimenhydrinate, haloperidol, meclozine, metoclopramide, metopimazine, oxypendyl, perphenazine, pipamazine, piprinhydrinate, prochloroperazine, promazine, scopolamine, sulpiride, thiethylperazine, thioproperazine, triflupromazine, trimethobenzamide, etc., which are frequently used in combination with vitamins and/or antiallergics;

at least one substance with an antiepileptic action, such as barbexaclone, barbiturate, beclamide, carbamazepine, chloroalhydrate, clonazepam, diazepam, ethosuximide, ethylphenacemide, lorazepam, mephenytoine, mesuximide, oxazolidine, phenaglycodol, phensuximide, phenytoine, primidone, succinimide-derivatives, sultiam, trimethadione, yalproinic acid, etc.; additives are commonly chosen from the classes of hypnotics and sedatives; an especially commonly used agent of this kind is carbamazepine.

at least one substance with antifibrinolytic activity, such as aminocapronic acid or tranexamic acid.

at least one anticonvulsive agent, such as beclamide, carbamazepine, clomethiazole, clonazepam, methylphenobarbital, phenobarbital or sultiam;

at least one substance which modifies choline concentration, by having an anticholinergic activity, for example. The following substances can be used, amongst others, as cholinergics: aubenoniumchloride, carbachol, cerulezide, dexpanthenol and stigmine-derivatives (such as distigminebromide, neostigminemethylsulfate, pyridostigmine-bromide); frequently used as anticholinergics are especially atropine, atropinmethonitrate, benactyzine, benzilonium-bromide, bevonium-methylsulfate, chlorobenzoxamine, ciclonium-bromide, clidinium-bromide, dicycloverine, diphemanil-methylsulfate, fenpiverinium-bromide, glycopyrroniumbromide, isopropamide-iodide, mepenzolate-bromide, octatropine-methylbromide, oxyphencyclimine, oxyphenonium-bromide, pentapiperide, pipenzolate-bromide, piperidolate, pridinol, propanidide, tridihexethyl-iodide and trospiumchloride; cholinesterase inhibitors, such as ambenonium-chloride, demecarium-bromide, echothiopate-iodide, etc., are also useful for this purpose;

at least one substance which can change, in the majority of cases diminish, the effect or concentration of histamine (antihistaminics). Preferred are hypoallergic carriers or hypoallergic edge active substances with n-3 (omega-3), less frequently with n-6 (omega-6), and mainly several, often 3–6 double bonds; such substances are occasionally employed with hydroxy, more rarely methyl-, or oxo-side groups, or in an epoxy configuration; further suitable agents of this class are, among other substances, aethylenediamine, alimemazine, antazoline, bamipine, bromo-azine, bromo-pheniramine, buclizine, carbinoxamine, chlorocyclizine, chloropyramine, chlorophenanine, chlorophenoxamine, cimetidine, cinnarizine, clemastine, clemizol, colamine (such as diphenhydramine), cyclizine, dexbrompheniramine, dexchlorpheniramine, difenidol, dimetindene, dimetotiazine, diphenhydramine, diphenylpyraline, dixyrazine, doxylamine, histapyrrodine, isothipendyl, mebhydroline, meclozine, medrylamine, mepyramine, methdilazine, pheniramine, piperacetazine, piprinhydrinate, pyrilamine (mepyramine), promethazine, propylamine, pyrrobutanine, thenalidine, tolpropamine, tripelennamine, triprolidine, etc.;

at least one substance belonging to the class of antihypertonics, such as many alpha-receptor agonists, aldosterone-antagonists, angiotensine-converting-enzyme-blockers, antisymphaticotonics, beta-blockers, calcium-antagonists, diuretics, vasodilators, etc.; suitable agents for this purpose are for example alpenolol, atenolol, bendroflumethiazide, betanidine, butizide, chlorotalidone, clonidine, cycletanine, cyclopenthiazide, debrisoquine, diazoxide, dihydralazine, dihydroergotaminmethanesulfonate, doxazinmesilate, guanethidine, guanoclor, guanoxane, hexamethonium-chloride, hydralazine, labetalol, mecanylanine, methyldopa, pargyline, phenoxybenzamine, prazosine, quinethazone, spironolactone, bescinnamine, reserpine, trichlorome-thiazide or vincamine;

at least one substance which is an inhibitor of biological activity, such as actinomycine C1, alpha-amanitine, ampicilline, aphidicoline, aprotinine, calmidazolium (R24571), calpaine-inhibitor I, calpaine-inhibitor II, castanospermine, chloroamphenicol, colcemide, cordycepine, cystatine, 2,3-dehydro-2-desoxy-n-acetyl-neuraminic acid, 1-desoxymannojirimycinehydrochloride, 1-desoxynojirimycine, diacylglycerolkinase-inhibitor, P1, P5-di(adenosine-5'-)-pentaphosphate, ebelactone A, ebelactone B, erythromycine, ethidiumbromide, N-hydroxyurea, hygromycine B, kanamycine sulfate, alpha2-macroglobuline, N-methyl-1-desoxynojirimycine, mitomycine C, myxothiazol, novobiocine, phalloidine, phenylmethylsulfonylfluoride, puromycine-dihydrochloride, rifampicine, staurosporine, streptomycine sulfate, streptozotocine, G-strophanthine, swainsonine, tetracycline-hydrochloride, trifluoperazine-dihydrochloride, tunicamycine, etc.; useful proteinase inhibitors are, for example, (4-amidinophenyl)methanesulfonylfluoride (APMSF), antipaine-dihydrochloride, antithrombine III, alpha-1-antitrypsine, aprotinine, bestatine, calpaine-inhibitor I, calpaine-inhibitor II, L-1-chloro-3-(4-tosylamido)-7-amino-2-heptanone-hydrochloride (TLCK), L-1-chloro-3-(4-tosylamido)-4-phenyl-2-butanone (TPCK), chymostatine, cystatine, 3,4-dichlorisocoumarin, E 64, selastatinal, hirudin, kallikrein-inhibitor (aprotinine) L-leucinthiol, leupeptine, pepstatine, phenylinethylsulfonylfluoride (PMSF), phosphoramidone, TLCK (tosyl-lysine-chloromethyl-ketone), TPCK (tosyl-phenylalanine-chloromethyl-ketone), trypsine-inhibitors, etc.;

at least one substance acting as an antihypotonic agent; quite frequently the corresponding drugs are from the classes of analeptics, cardiacs or corticoids. Suitable agents for this purpose are, for example, angiotensine-amide, cardaminol, dobutamine, dopamine, etifelmine, etilefrine, gepefrine, heptaminol, midodrine, oxedrine, etc., especially norfenefrine;

at least one substance from the group of anticoagulants. Among other substances, some coumarin-derivatives are suitable for this purpose, as well as heparine and heparinoids, hirudine and related substances, derma-tansulfate etc.; most frequently used agents of this class are acenocumarin, anisindione, diphenadione, ethylbiscoumacetate, heparine, hirudine, phenprocoumon, as well as warfarine;

at least one substance from the class of amtimycotics; well-suited examples of such agents include: amphotericine, bifanozol, buclosamide, chinoline-sulfate chloromidazol, chlorophenesine, chloroquinaldol, clodantoine, cloxiquine, cyclopiroloxamine, dequaliniumchloride, dimazol, fenticlor, flucytosine, griseofulvine, ketoconazol, miconazol, natamycine, sulbentine, tioconazol, tolnaftate, etc.; particularly frequently, amphotericine, clotrimazol or nystatine are likely to be used for this purpose;

at least one substance from the class of antimyasthenics, such as pyridostigmine-bromide;

at least one substance which is active against morbus parkinson, such as amantadine, benserazide, benzatropine, biperidene, cycrimine, levodopa, metixene, orphenadrine, phenglutarimide, pridinol, procyclidine, profenamine or trihexyphenidyl;

at least one substance with an antiphlogistic activity, such as aescine, acetylsalicylic acid, alclofenac, aminophenazone, azapropazone, benzydamine, bumadizone, chlorothenoxazine, diclofenac, flufenaminic acid, glafenine, ibuprofene, indometacine, kebuzone, mefenam acid, metiazic acid, mesalazine, mofebutazone, naproxene, niflumine acid, salts, such as Na-salt, noramidopyrinium-methane-sulfonate, orgoteine, oxyphenbutazone, phenylbutazone, propyphenazone, pyridoxine, tolmetine, etc.; very suitable is, for example, ibuprofen; some of the agents commonly used as antiphlogistics also exhibit an antihistaminic or analgetic activity and belong to the classes of corticoids, vasoactiva, opthalmics or otologics;

at least one substance which is an antipyretic, such as acetylsalicylic acid, alclofenac, aminophenazone, benzydamine, bumadizone, chinine, chlorinethenoxazine, lactylphenetidine, meprob, paracetamol, phenacetine, propyphenazone or salicylamide;

at least one substance with an antirheumatic activity, such as acetylsalicylic acid, benorilate, chloroquine, diclofenac, fenoprofene, flufenaminic acid, ibuprofene, kebuzone, lactylphenetidine, mefenamic acid, mofebutazone, naproxene, sodiumaurothiomalate, nifenazone, nifluminic acid, D-penicillamine and salicylamide. Edge active substances, carriers and/or agents, with a hypoallergic action, for example from the groups of analgetics, corticoids and glucocorticoids, enzymes or vitamins, etc., are preferred for this purpose, as well as antiphlogistics, such as quinine, nicotinic acid-, nonylic acid-, or salicylic acid-derivatives, meprobamate, etc.;

at least one antiseptic such as acriflaviniumchloride, cetalkonium-chloride, cetylpyridinium-chloride, chlorohexidine, chloroquinaldol, dequaliniumchloride, domiphene-bromide, ethacridine, hexetidine, merbromine, nitrofural, oxyquinol, phanquinone, phenazopyridine or phenylmercuriborate, as well as fatty acids with an uneven number of carbon atoms;

at least one respiratory analeptic or respiration stimulant, such as amiphenazol, ascorbic acid, caffeine, cropropamide, crotethamide, etamivane, ephedrine, fominobene, nicethamide; or aminophenazol and doxaprame, for example;

at least one broncholytic, such as bamifylline, beclometasone, dexometasone (e.g. in dexometasone-21-isonicotinate), diprophylline, ephinedrine (e.g. in ephinedrinehydrogentartrate), fenoterol, hexoprenaline, ipratropium-bromide, iso-etarine, isoprenaline, orciprenaline, protocylol, proxyphylline, reproterol, salbutamol, terbutaline, tetroquinol, theophyilline, etc.; and biological extracts, for example from anis, eucalyptus, thyme, etc.;

one cardiotonic, especially aminophylline, benfurodilhemisuccinate, etofylline, heptaminol, protheobromine or proxyphylline;

at least one substance from the class of chemotherapeutic agents, for example, acediasulfone, acriflaviniumchloride, ambazone, dapsone, dibrompropamidine, furazolidone, hydroxymethyinitrofurantoine, idoxuridine, mafenide and sulfateolamide, mepacrine, metronidazol, nalidixinic acid, nifuratel, nifuroxazide, nifuarazine, nifurtimox, ninorazol, nitrofurantoine, oxolinic acid, pentamidine, phenazopyridine, phthalylsulfatehiazole, pyrimethamine, salazosulfapyridine, sulfacarbamide, sulfacetamide, sulfachloropyridazine, sulfadiazine, sulfadicramide, sulfadimethoxine, sulfaethidol, sulfafurazol, sulfaguanidine, sulfaguanol, sulfamethizol, sulfamethoxazol and cotrimoxazol, sulfamethoxydiazine, sulfamethoxypyridazine, sulfamoxol, sulfanilamide, sulfaperine, sulfaphenazol, sulfatehiazol, sulfisomidine, tinidazol, trimethoprim, etc.;

at least one substance from the class of coronary dilatators, such as bamifylline, benziodarone, carbochromes, dilazep, dipyridamol, etafenone, fendiline, hexobendine, imolamine, lidoflazine, nifedipine, oxyfedrine, pentaerythrityltetranitrate, perhexiline, prenylamine, propatylnitrate, racefemine, trolnitrate, verapamil, visnadine, etc.;

at least one cytostatic, for example, from the group of alkylating agents, antibiotics, platinum compounds, hormones and their inhibitors, interferones, etc.; very frequently used substances of this kind are: aclarubicine, azathioprine, bleomycine, busulfane, calciumfolinate, carboplatinum, carmustine, chloroambucil, cis-platinum, cyclophosphamide, cytarabine, daunorubicine, epirubicine, fluorouracil, fosfestrol, hydroxycarbamide, ifosfamide, lomustine, melphalane, mercaptopurine, methotrexate, mitomycine C, mitopodozide, mitramicyne, nimustine, pipobromane, prednimustine, procarbazine, testolactone, theosulfane, thiotepa, tioguanine, triaziquone, trofosfamide, vincristine, vindesine, vinblastine, zorubicine, etc.;

an intestinal antiseptic, such as broxyquinoline, clioquinol, diodohydroxyquinoline, halquinol, etc.;

at least one diuretic, such as acetazolamide, aminophylline, bendroflumethiazide, bumetanide, butizide, chloroazanile, chloromerodrine, chlorothiazide, chlorotalidone, clopamide, clorexolone, cyclopenthiazide, cyclothiazide, etacrynic acid, furosemide, hydrochlorothiazide, hydroflumethiazide, mefruside, methazolamide, paraflutizide, polythiazide, quinethazone, spironolactone, triamterene, trichloromethiazide, xipamide, etc.;

at least one ganglion blocker, such as gallamintriethiodide, hexamethonium-chloride, mecamylamine, etc.;

at least one substance for the therapy of arthritis, preferably analgetics or for example allopurinol, benzbromarone, colchicine, benziodarone, probenecide, sulfinpyrazone, tenoxicam, etc.; in very many cases allopurinol;

at least one glucocorticoid, such as beclomethason, betamethason, clocortolone, cloprednol, cortison, dexamethason (e.g. as a dexamethasonephosphate), fludrocortison, fludroxycortide, flumetason, fluocinolonacetonide, fluocinonide, fluocortolon (e.g. as a fluocortoloncapronate or fluocortolontrimethylacetate), fluorometholon, fluprednidenacetate, hydrocortison (also as a hydrocortison-21-acetate, hydrocortison-21-phosphate, etc.), paramethason, prednisolon (e.g. in the form of methylprednisolon, prednisolon-21-phosphate, prednisolon-21-sulfobenzoate, etc.), prednison, prednyliden, pregnenolon, triamcinolon, triamcinolonacetonide, etc.;

at least one agent with a putative anti-flew action, such as moroxydine;

at least one haemostatic, such as adrenalon, ascorbic acid, butanol, carbazochrome, etamsylate, protamine, samatostatine etc.; thyroidal hormones and vitamins can be employed for this purpose as well;

at least one hypnotic, from the class of barbiturates, benzodiazepines, bromo-compounds, ureids, etc., for example; quite commonly applied for this purpose are, e.g. acecarbromal, alimemazintartrate allobarbital, amobarbital, aprobarbital, barbital, bromo-isoval, brotizolam, carbromal, chloroalhydrate, chloroalodol, chlorobutanol, clomethiazol, cyclobarbital, diazepam, diphenhydramine, doxylamine, estazolam, ethchlorvynol, ethinamate, etomidate, flurazepam, glutethimide, heptabarb, hexobarbital, lormetazepam, malperol, meclozine, medozine, methaqualon, methyprylon, midazolam, nitrazepam, oxazepam, pentobarbital, phenobarbital, promethazine, propallylonal, pyrithyldion, secbutabarbital, secobarbital, scopolamine, temazepam, triazolam, vinylbital, etc.; various extracts from balm-mint, valerian, and passiflora are also used;

at least one immunoglobuline, from the IgA, IgE, IgD, IgG, IgM classes or an immunoglobuline fragment, such as a Fab- or Fab2-fragment, or the corresponding variable or hypervariable region, if required in combination with other agents and/or chemically, biochemically or genetically manipulated;

An immunoglobuline can be of the IgA, IgD and IgE, IgG (e.g. Ig G1, Ig G2, Ig G3, Ig G4) or IgM type. In the context of this application, any chemical or biochemical derivative of any immunoglobuline (Ig) is considered useful, for example, an Ig G-gamma chain, an Ig G-F(ab')2 fragment, an Ig G-F(ab) fragment, an Ig G-Fc fragment, an Ig-kappa chain, a light chain of Ig-s (e.g. a kappa and lambda chain), but also even smaller immunoglobuline fragments, such as the variable or hypervariable regions, or artificial modifications of any of these substances.

at least one substance with an immunostimulating activity, with an immunosuppressive potency, with a capability to give rise to the production of immunoglobulines or other immunologically active substances (endotoxines, cytokines, lymphokines, prostaglandines, leucotrienes, other immuno modulators or biological messengers), including vaccines. Antibodies against any of these substances can also be used; preferred are immunotransfersomes with or without endotoxines, cytokines, prostaglandines, leucotrienes, with other immunomodulators, immunologically active cellular or molecular fragments, as well as corresponding antagonists, derivatives or precursors; particularly preferred compounds are lipid A and other glycolipids, muraminic acid derivatives, trehalose derivatives, phythaemaglutinines, lectins, polyinosine, polycytidylic acid (poli I:C), dimepranol-4-acetamidobenzoate, erythropoietin, 'granulocyte-macrophage colony stimulating factor' (GM-CSF), interleukine I and II, III and VI, interferon alpha, beta and/or gamma, leucotriene A, B, C, D, E and F, propandiamine, prostaglandine A, B, C, D, E, F, and I (prostacycline), tumor necrosis factor-alpha (TNF-alpha), thromboxan B, as well as immunoglobulines of types IgA, IgE, IgD, IgG, IgM; furthermore, suitable tissue and plant extracts, their chemical, biochemical or biological derivatives or replacements, their parts, such as characteristic peptide chains, etc.; as immunosuppressives, ganciclovir, azathiiprin, cyclosporin, FK 506 etc. are frequently used;

at least one contraceptive agent, such as medroxyprogesteronacetate, lynesterol, lvonorgestrel, norethisteron, etc.;

at least one circulation analeptic, such as cafedrin, etamivan, etilefrin, norfenefrin, pholedrin, theodrenalin, etc.;

at least one drug for the therapy of liver diseases, such as orazamide, silymarin, or tiopromin;

at least one substance with a light-protective function, such as mexenone;

at least one antimalaria agent, such as amodiaquin, hydroxychloroquin or mepacrin;

at least one substance for migraine or schizophrenia treatment, such as certain analeptics, beta-blockers, clonidin, dimetotiazine, ergotamine, lisurid (hydrogen maleate), methysergide, pizotifen, propranolol, proxibarbal, etc. Even more suitble are the serotonine antagonists or the blockers of serotonin receptors, such as 5-HT1, 5-HT2 or 5-HT3; well suited for use according to this invention are also the receptor blockers AH21467 (Glaxo), AH25086 (Glaxo), GR43175 (Glaxo), GR38032 (Glaxo, =ondansetron), 5-hydroxytryptamine, ketanserine, methiothepin, alpha-methyl-5HT, 2-methyl-5HT, etc.;

at least one mineral corticoid, such as aldosterone, fludrocortison, desoxycortonacetate, corresponding derivatives, etc.;

at least one morphine antagonist (such as amiphenazol, lealvallorphane, nalorphine) or some substance with morphine-like properties such as casomorphine, cyclo (leu-gly), dermorphine, met-encephaline, methorphamide (tyr-gly-gly-phe-met-arg-arg-val), morphiceptine, morphine modulating neuropeptide (ala-gly-glu-gly-leu-ser-ser-pro-phe-trp-ser-leu-ala-ala-pro-gln-arg-phe-NH$_2$) etc.;

at least one muscle relaxant, which frequently belongs to the groups of competitively or depolarising curare-agents, myotonolytics or analgetics; suitable substances with the desired effect are, among other materials, acetylsalicilic acid, alcuronium-chloride, azapropazon, atracuriumbesilate, baclofen, carisoprodol, quinine derivatives, chloromezanon, chlorophenesincarbamate, chlorozoxazon, dantrolen, decamethoniumbromide, dimethyltubocurariniumchloride, fenyramidol, gallamintriethiodide, guaiphensine, hexafluoreniumbromide, hexacarbacholinbromide, memantin, mephenesin, meprobamate, metamisol, metaxalon, methocarbamol, orphenadrin, paracetamol, phenazon, phenprobamate, suxamethoniumchloride, tetrazepam, tizanidin, tubocurarinchloride, tybamate, etc.;

at least one narcotic, such as alfentanil, codeine, droperidol, etomidate, fentanil, flunitrazepam, hydroxybutiric acid, ketamine, methohexital, midazolam, thebacon, thiamylal, thiopental, etc., as well as corresponding derivatives;

at least one substance with a neurotherapeutic activity, such as anaesthetics and vitamins, atropine-derivatives, benfotiamine, choline-derivatives, caffeine, cyanocobolamine, alpha-liponic acid, mepivacaine, phenobarbital, scopolamine, thiaminchloride hydrochloride, etc., and, most notably, procaine;

at least one neuroleptic, e.g. butyrophenon-derivatives, phenotiazin-derivatives, tricyclic neuroleptics, as well as acetophenazine, benperidol, butaperazine, carfenazine, chloropromazine, chloroprothixen, clopenthixol, clozapine, dixyrazine, droperidol, fluanison, flupentixol, fluphenazine, fluspirilen, haloperidol, homofenazine, levomepromazine, melperon, moperon, oxipertin, pecazine, penfluridol, periciazine, perphenazine, pimozide, pipamperon, piperacetazine, profenamine, promazine, prothipendyl, sulforidazine, thiopropazate, thioproperazine, thioridazine, tiotixen, trifluoperazine, trifluperidol, triflupromazine, etc.; in particular, haloperidol and sulperide are often used for this purpose;

at least one neurotransmitter or one of its antagonists; preferably, acetylcholine, adrenaline, curare (and, e.g. its antagonist edrophonium-chloride), dopamine, ephedrine, noradrenaline, serotonine, strychnine, vasotonine, tubocurarine, yohimbine, etc. are used;

at least one opthalmic, in many cases from the groups of anaesthetics, antibiotics, corticoids, eye-tonics, chemotherapeutics, glaucome agents, virustatics, antiallergics, vasodilatators, or vitamins;

at least one parasympathicomimetic (e.g. bethanecholchloride, carbachol, demecarium-bromide, distigmin-bromide, pyridostigmin-bromide, scopolamine) or at least one parasympathicolytic (such as benzatropine, methscopolamine-bromide, pilocarpine or tropicamide);

at least one agent for the therapy of psoriasis and/or neurodermitis; particularly well suited for this purpose are carrier substances with a hypoallergic action or the corresponding edge active compounds, with n-3 (omega 3), less frequently with n-6 (omega 6), mainly with multiple, often 3–6, double bonds and/or hydroxy, more seldom methyl-, or oxo-side groups; these can also appear as side chains on further agent molecules; side groups on the 15th carbon atom are particularly efficient; as additives, amongst other substances, antimycotics, cytostatics, immunosuppressants or antibiotics can be used;

at least one agent for the dilatation of the iris (mydriatic), such as atropine, atropinemethonitrate, cyclopentolate, pholedrine, scopolamine or tropicamide;

at least one substance with a psychostimulating action; well suited for this purpose are, for example, amphetaminil, fencamfamine, fenetylline, meclofenoxate, methamphetamine, methylphenidate, pemoline, phendimetrazine, phenmetrazine, prolintane or viloxazine;

at least one rhinologic, such as buphenine, cafaminol, carbinoxamide, chlorophenamim, chlorotenoxazine, clemastine, dextromethorpane, etilefrine, naphazoline, norephedrine, oxymetazoline, phenylaprhine, piprinydrinate, pseudoephedrine, salicylamide, tramazoline, triprolidine, xylometazoline, etc.; from biological sources especially the radix gentiane extract;

at least one somnifacient (such as sleep-inducing peptide (trp-ala-gly-gly-asp-ala-ser-gly-glu)), or a corresponding antagonist (such as bemegride);

at least one sedative or tranquilizer, as the former, for example, acecarbromal, alimemazine, allobarbital, aprobarbital, benzoctamine, benzodiazepine-derivatives, bromo-isoval, carbromal, chloropromazine, clomethiazol, diphenyl-methane-derivatives, estazolam, fenetylline, homofenazine, mebutamate, mesoridazine, methylpentynol, methylphenobarbital, molindone, oxomemazine, perazine, phenobarbital, promethazine, prothipendyl, scopolamine, secbutabarbital, trimetozine, etc.; as a tranquilizer, for example, azacyclonol, benactyzin, benzoctamine, benzquinamide, bromo-azepam, chlorodiazepoxide, chlorophenesincarbanate, cloxazolam, diazepam, dipotassium-chloroazepate, doxepine, estazolam, hydroxyzine, lorazepam, medazepam, meprobamate, molindone, oxazepam, phenaglycodol, phenprobamate, prazepam, prochloroperazine, rescinnamine, reserpine or tybamate; drugs, such as distraneurine, hydantoine-derivatives, malonyl uric acid-derivatives (barbiturates), oxazolidine-derivatives, scopolamine, valepotriate, succinimide-derivatives, or hypnotics (e.g. diureides (such as barbiturates)), methaqualon, meprobromate, monoureides (such as carbromal), nitrazepam, or piperidin-dione, can be used for this purpose; amongst other substances, certain thymoleptics, such as librium or tofranil, can be used as antidepressants;

at least one substance from the class of spasmolytics, e.g. adiphenine, alverine, ambicetamide, aminopromazine, atropine, atropine methonitrate, azintamide, bencyclane, benzarone, bevonium-methylsulfate, bietamiverine, butetamate, butylscopolammoniumbromide, camylofine, carzenide, chlorodiazepoxide, cionium-bromide, cyclandelate, cyclopentolate, dicycloverine, diisopromine, dimoxyline, diphemanil-methylsulfate, ethaverine, ethenzamide, fencarbamide, fenpipramide, fenpivennum-bromide, gefarnate, glycopyrroniumbromide, hexahydroadiphenin, hexocycliummethylsulfate, hymecromon, isometheptene, isopropamidiodide, levomethadone, mebeverine, metamizon, methscopolamine-bromide, metixen, octatropine-methylbromide, oxazepam, oxybutin, oxyphenonium-bromide, papaverine, paracetamol, pentapiperide, penthienate-methobromide, pethidine, pipenzolate-bromide, piperidolate, pipoxolane, propanthelin-bromide, propylphenazon, propyromazine-bromide, racefemine, scopolamine, sulpiride, tiemoniumiodide, tridihexethyliodide, tropenzilinbromide, tropinbenzilate, trospiumchloride, valethamatbromide, etc.; furthermore, belladonna alkaloids, papaverine and its derivatives, etc.;

at least one sympathicolytic, e.g. azapetine or phentolamine;

at least one sympathicomimetic, e.g. bamethane, buphenine, cyclopentamine, dopamine, L-(−)-ephedrine, epinephrine, etilefrine, heptaminol, isoetarine, metaraminol, methamphetamine, methoxamine, norfenefrine, phenylpropanolamine, pholedrine, propylhexedrine, protokylol or synephrine;

at least one tuberculostatic, such as an antibiotic, p-aminosalicylic acid, capreomycine, cycloserine, dapson, ethambutol, glyconiazide, iproniazide, isoniazide, nicotinamide, protionamide, pyrarinamide, pyrodoxine, terizidone, etc., and, particularly preferred thereof, ethambitol and isoniazide;

at least one urologic, e.g. a bladder tension modifying agent (such as cholinecitrate, distigminebromide, yohimbine), a corresponding antiinfection agents (antibiotics, chemotherapeutics, or nitrofurantoid-, chinolone-, or sulfonamide-derivative); furthermore, adipinic acid, methionine, methenamine-derivatives, etc.;

at least one substance with a vasoconstricting action; often, adrenalone, epinephrine, felypressine, methoxamine, naphazoline, oxymetazoline, tetryzoline, tramazoline or xylometazoline are used for this purpose;

at least one substance which is a vasodilatator, such as e.g. azapetine, banethane, bencyclane, benfurodilhemisuccinate, buphenine, butalamine, cinnarizine, diprophylline, hexyltheobromine, ifenprodil, isoxsuprine, moxisylyte, naftidrofuryl, nicotinylalcohol, papaverine, phenoxybenzamine, piribedil, primaperone, tolazoline, trimetazidine, vincamine or xantinol-nicotinate;

at least one veins agent, e.g. aescine, benzarone, calciumdobesilate, dihydroergotaminemesilate, diosmine, hyydroxyethylrutoside, pignogenol, rutoside-aesinate, tribenoside, troxerutine, etc.;

at least one virustatic, e.g. one immunostimulating agent, and/or an additional drug, such as as moroxydine or tromantadine, which may stimulate action of the immunostimulator;

one agent for the treatment of wounds; for example, dexpanthenol, growth stimulating factors, enzymes or hormones, especially in combination with carriers which contain essential substances; povidon-iodide, fatty acids which are not straight, cetylpyridiniumchloride, chinoline-derivatives of known antibiotics and analgetics are useful;

at least one substance with a toxic action or a toxin; common toxins from plant or microbial sources in particular 15-acetoxyscirpenol, 3-acetyldeoxynivalenol, 3-alpha-acetyldiacetoxyscirpenol, acetyl T-2 toxin, aflatoxicol I, aflatoxicol II, aflatoxin B1, aflatoxin B2, aflatoxin B2-alpha, aflatoxin G1, aflatoxin G2, aflatoxin G2-alpha, aflatoxin M1, aflatoxin M2, aflatoxin P1, aflatoxin Q1, alternariol-monomethyl ether, aurovertin B, botulinum toxin D, cholera toxin, citreoviridin, citrinin, cyclopiazonic acid, cytochalasin A, cytochalasin B, cytochalasin C, cyrochalasin D, cytochalasin, cytochalasin H, cytochalasin J, deoxynivalenol, diacetoxyscirpenol, 4,15-diacetylverrucarol, dihydrocytochalasin B, enterotoxin STA, fusarenon X, iso T-2 toxin, O-methylsterigmatocystin, moniliformin, monoacetoxyscirpenol, neosolaniol, ochratoxin A, patulin, penicilinic acid, pertussis toxin, picrotoxin, PR-toxin, prymnesin, radicinin, roridin A, rubratoxin B, scirpentriol, secalonic acid D, staphylococcalenterotoxin B, sterigmatocystin, streptolysin O, streptolysin S, tentoxin, tetrahydrodeoxyaflatoxin B1, toxin A, toxin II, HT-2 toxin, T-2-tetraol, T-2 toxin, trichothecin, trichothecolon, T-2 triol, verrucarin A, verrucarol, vomitoxin, zearalenol and zearalenon.

at least one substance which affects growth in humans or animals, such as basic fibroblast growth factor (BFGF), endothelial cell growth factor (ECGF), epidermal growth factor (EGF), fibroblast growth factor (FGF), insulin, insulin-like growth factor I (LGF I), insulin-like growth factor II (LGF II), nerves-growth factor-beta (NGF-beta), nerves growth-factor 2,5s (NGF 2,5s), nerves growth-factor 7s (NGF 7s), platelet-derived growth factor (PDGF), etc.;

a carrier and/or agent which creates a protective layer on and/or in a barrier, such as skin, against poison, light UV-, gamma- or other radiation; against detrimental biological agents such as viruses, bacteria, toxins, etc.; carrier components and/or agents can hamper the detrimental action by chemical, biochemical, or biological means or else may prevent or diminish the penetration of such adversary agents;

at least one fungicide, herbicide, pesticide, or insecticide;

at least one plant hormone, e.g. abscisic acid, abscisic acid-methylester, 3-acetyl-4-thiazolidine-carboxyl acid, 1-allyl-1-(3,7-dimethyloctyl)-piperidinium bromide, 6-benzylaminopurine, 6-benzylaminopurine 9-(betaglucoside), butanedio acid mono(2,2-dimethyl hydrazide), chlorocholine chloride, 2-chloroethyl-tris-(2'-methoxyethoxy)silane, 2-(o-chlorineophenoxy)-2-methylpropionic acid, 2-(p-chlorophenoxy)-2-methylpropionic acid, 2-(o-chlorophenoxyipropionic acid, 2-(m-chlorophenoxy)propionic acid, clofibrinic acid, colchicine, o-coumarinic acid, p-coumarinic acid, cycloheximide, alpha, beta-dichloroisobutiric acid, 2-(2,4-dichlorophenoxy)propanoic acid, 2,3-dihydro-5, 6-diphenyl 1,4-oxathiine, dihydrozeatine, 6-(gamma, gamma-dimethylallylamino)purino riboside, 3-(2-[3,5-dimethyl-2-oxocyclohexyl-2-hydroxyethyl])-glutarimide, trans-2-dodecenedioic acid, ethyl-8-chloro-1-indazol-3-yl-acetate, N6-furfuryladenosine, 6-furfurylaminopurineriboside, gibberellic acid methylester, gibberellin A3-acetate, gibberellin A1 methylester, gibberellin A4 methylester, gibberellin A5 methylester, gibberellin A7 methylester, gibberellin A9 methylester, gibberellin A3 methylester 3,13-diacetate gibberinic acid, allogibberinic acid, gibberinic acid methylester, glyoxim, 22(s), 23(s)-homobrassinolide, 9-hydroxyfluorene 9 -carboxylate, indol-3-acetic acid, indol-3-acetic acid ethylester, indol-3-propanoic acid, N6-(2-isopentenyl)adenine, N6-(2-isopentenyl) adenosine, 2-isopropyl-4-dimethylamino-5-methylphenyl-1-piperidinecarboxylat methylchloride, kinetinglucoside, kinetinriboside, melissylalcohol, 1-methyladenine, methyl 2-chloro-9-hydroxy-fluorene-9-carboxylate, methyl 3,6-dichloro-o-anisate, 6-methylmercaptopurine, 1-naphthylacetamide, nonanoic acid methylester, 6-piperidino-1-purine, n-triacontanol, (–)-xanthoxine, zeatine glucosides, etc.;

at least one pheromone or one pheromone-like substance, such as (–)-bornyl acetate, trans-5-decenol, cis-5-decenyl acetate, trans-5-decenyl acetate, 2,6-dichlorophenol, 1,7-dioxaspiro[5.5]undecane, trans-8, trans-10-dodecadienol ([E,E]-8,10-DDDOL), trans-7, cis-9-dodecadienyl acetate ([E,Z]-7,9-DDDA), trans-8, trans-10-dodecadienyl acetate ([E,E]-8,10-DDDA), cis-7-dodecen-1-ol (Z-7-DDOL), trans-10-dodecenol, cis-7-dodecenyl acetate (Z-7-DDA), cis-8-dodecenyl acetate, trans-8-dodecenyl acetate, 11-dodecenyl acetate, cis-7,8-epoxy-2-methyl-octadecane, cis-9-heneicosene, cis-7, cis-11-hexadecadienylacetate ([Z, Z]-7,11-HDDA), cis-7, trans-11-hexadecadienyl acetate ([Z,E]-7,11-HDDA), cis-9-hexadecenal (Z-9-HDAL), cis-11-hexadecenal (Z-11-HDAL), cis-11-hexadecenol (Z-11-HDOL), cis-11-hexadecenyl acetate (Z-11-HDA), trans-2-hexenyl acetate, cis-7-tetradecenal (Z-7-TDAL), cis-9-tetradecenol (Myristoleyl alcohol; Z-9-TDOL), cis-7-tetradecenol (Z-7-TDOL), cis-11-tetradecenol, cis-7-tetradecenyl acetate (Z-7-TDA), cis-9-tetradecenyl acetate (Myristoleyl acetate; Z-9-TDA), cis-11-tetradecenyl acetate (Z-11-TDA), trans-11-tetradecenyl acetate (E-11-TDA), cis-9-tetradecenyl formate (Myristoleyl formate; Z-9-TDF), isoamyl acetate (acetic acid 3-methylbutyl ester), 2-methyl-3-buten-2-ol, 3-methyl-2-cyclohexen-1-ol, cis-14-methyl-8-hexadecenal, cis-2-methyl-7-octadecene, 4-methylpyrrole-2-carboxylic acid methyl ester (Methyl 4-methylpyrrole 2-carboxylate) cis-13-octadecenal 13-octadecyn-1-ol, 2-(phenyl)ethyl propionate(phenylethanol propanoate), propyl cyclohexylacetate, cis-9,trans-11-tetradecadienol ([Z,E]-9,11-TDDOL), cis-9, trans-11-tetradecadienyl acetate ([Z,E]-9,11-TDDA), cis-9, trans-12-tetradecadienyl acetate ([Z,E]-9,12-TDDA), trichloroacetic acid esters, cis-9-tricosene, undecanal, etc.;

at least one pigment or one colouring substance;
at least one carbohydrate;

A carbohydrate, normally, has a basic formula $C_x(H_2O)_y$, e.g. in sugar, starch, cellulose, and, moreover, can be derivatised in many different ways.

A monomeric carbohydrate residue is, for example, a natural monosaccharide residue, which in many cases is an adduct of a pentose or a hexose in aldose or ketose form which, in principle, can adopt L- or D-configurations. Owing to the space constraints and due to their greater biological relevance, only the latter will be referred to in the following.

An aldose with five carbon atoms (aldo-pentose, or simply pentose) is for example D-arabinose, D-lyxose, D-ribose or D-xylose.

A ketose with five carbon atoms (keto-pentose) is e.g. D-ribulose or D-xylulose.

An aldose with six carbon atoms (aldo-hexose, or simply hexose) is e.g. D-allose, D-altrose, D-galactose, D-glucose, D-mannose or D-talose. A ketose with six carbon atoms (or simply keto-hexose) is e.g. D-fructose, D-psicose, D-sorbose or D-tagatose.

A hexose, very frequently, exists in a cyclic form, as a pyranose (aldose), for example; alpha- or beta-D-glucopyranose are two typical examples for this. Another type of hexose is furanose, e.g. in an alpha- or beta-D-fructose. The pyranosyl residue is particularly preferably conjugated to a hydroxy group, the latter then being located in 1- or 6-positions; the furanosyl residue is preferably conjugated to the corresponding groups in positions 1- or 5-.

A carbohydrate residue, moreover, can be a natural disaccharide residue, e.g. a disaccharide residue consisting of two hexoses. Such a disaccharide residue arises, for example, through condensation of two aldoses, e.g. D-galactose or D-glucose, or one aldose, e.g. D-glucose and one ketose, e.g. fructose; disaccharides formed from two aldoses, such as lactose or maltose, are preferably conjugated to the phosphatidyl group through the hydroxy group, which is located in position 6- of the corresponding pyranosyl residue. A disaccharide formed from an aldose and a ketose, such as saccharose, is preferably conjugated through a hydroxyl-group in position 6- of the pyranosyl residue or in position 1- of the furanosyl residue.

A carbohydrate residue, moreover, is any derivatised mono-, di- or oligosaccharide residue, in which, for example, an aldehyde group and/or one or two terminal hydroxy groups are oxidized to carboxy groups, e.g. in a D-glucar-, D-glucon- or D-glucoronic acid residue, all such residues being normally in the form of cyclic lactone residues. The aldehyde- or keto-groups in a derivatised mono- or disaccharide residue, moreover, can be reduced to hydroxy groups, e.g. in inositol, sorbitol or D-mannitol. Furthermore, individual hydroxy groups can be replaced by hydrogen atoms, e.g. in desoxysugars, such as 2-desoxy-D-ribose, L-fucose or L-rhamnose, or through amino groups, e.g. in aminosugars, such as D-galactosamine or D-glucosamine.

A carbohydrate can result from a cleaving action, starting with one of the mentioned mono- or disaccharides, by a strong oxidation agent, such as periodic acid. Amongst the biologically most important or most active carbohydrates are e.g. 2-acetamido-N-(epsilon-amino-caproyl)-2-deoxy-beta-gluccopyranosylamine, 2-acetamido-2-amino-1,2-dideoxy-beta-glucopyranose, 2-acetamido-1-beta-(aspartamido)-1,2-dideoxyglucose, 2-acetamido-4,6-o-benzyliden-2-deoxybeta-glucopyranose, 2-acetamido-2-deoxyallose, 3-acetamido-3-deoxyallose, 2-acetamido-2-deoxy-3-o-(beta-galactopyranosyl)-galactopyranose, 2-acetamido-2-deoxy-4-o-([4-o-beta-galactopyranosyl-beta-galactopyranosyl]-beta-galactopyranosyl)-glucopyranose, 2-acetamido-2-deoxy-3-o-(beta-galactopyranosyl)-alpha-glucopyranose, 6-o-(2-acetamido-2-deoxy-4-[beta-galactopyranosyl]-beta-glucopyranosyl)-galactopyranose, 4-o-acetamido-2-deoxy-6-o-(beta-galacto-4-o-(6-o-[2-acetamido-2-deoxy-beta-glucopyranosyl]-beta-galactopyranosyl)glucopyranose, 2-acetamido-2-deoxygalactose, 2-acetamido-2-deoxyglucose, 3-acetamido-3-deoxyglucose pyranose, 6-o-(2-acetamido-2-deoxy-beta-glucopyranosyl)-galactopyranose, 2-acetamido-2-deoxy-1-thio-beta-glucopyranose 3,4,6 -triacetate, acetopyruvic acid, N-acetylchondrosamine, N-acetylgalactosamine, N-acetylglucosamine, N-acetyl-alpha-glucosamine 1-phosphate, N-acetylglucosamine 6-phosphate, N-acetylglucosamine 3-sulfate, N-acetylglucosamine 6-sulfate, N-acetylheparine, N-acetyllactosamine, N-acetyl-beta-mannosamine, N-acetylneuraminic acid, N-acetyl-neuramine-lactose, 1-o-acetyl-2,3,5-tri-o-benzoyl-beta-ribofuranose, trans-aconic acid, adenine-9-beta-arabino-furanoside, adenosine 5'-diphospho-glucose, adenosine 5'-diphosphomannose, adonite, adonitol, adonose, agar, algin, alginic acid, beta-allose, alpha glycerophosphate, alpha ketoglutaric acid, altrose, (−)-altrose, p-amino-benzyl-1-thio-2-acetamido-2-deoxy-beta-glucopyranoside, N-epsilon-aminocaproyl-beta-fucopyranosylamine, N-epsilon-aminocaproyl-alpha-galactopyranosylamine, 2-amino-2-deoxygalactopyranose, 6-amino-6-deoxyglucopyranose, 1-amino-1-deoxy-beta-glucose, 6-aminohexyl-N-acetyl-beta-thioglucosaminide, 6-aminohexyl-1-thio-beta-galactopyranoside, 5-aminoimidazole-4-carboxamidoxime-1-beta-ribofuranosyl 3':5'-cyclo-monophosphate, delta-aminolevulinic acid, p-aminophenyl-2-acetamido-2-deoxy-beta-glucopyranoside, p-aminophenyl-2-acetamido-2-deoxy-1-thio-beta-glucopyranoside, p-aminophenyl-alpha-fucopyranoside, p-aminophenyl-alpha-galactopyranoside, p-aminophenyl-beta-galactopyranoside, p-aminophenyl-alpha-glucopyranoside, p-aminophenyl-beta-glucopyranoside, c-aminophenyl-beta-glucuronide, p-aminophenyl-1-thio-beta-glucuronide, p-aminophenyl-beta-lactopyranoside, p-aminophenyl-alpha-mannopyranoside, p-aminophenyl-beta-thiofucopyranoside, p-aminophenyl-1-thio-beta-galactopyranoside, p-aminophenyl-1-thio-beta-glucopyranoside, p-minophenyl-1-thio-beta-xylopyranoside, p-aminophenyl-beta-xylopyranoside, 5-amino-1-(beta-ribofuranosyl) imidazole 4-carboxamide, amygdaline, n-amyl beta-glucopyranoside, amylopectine, amylose, apigenine 7 -o-hesperidoside, arabinitol, arabinocytidine, 9-beta-arabinofuranosyladenine, 1-beta-arabinofuranosylcytosin, arabinose, arabinose 5-phosphate, arabinosylcytosine, arabite, arabitol, arbutine, atp-ribose, atractyloside, aurothioglucose, n-butyl 4-o-beta-galactopyranosyl-beta-glucopyranoside, calcium gluconate, calcium heptagluconate, carboxyatractyloside, carboxymethylamylose, carboxymethylcellulose, carboxyethylthioethyl-2-acetamido-2-deoxy-4-o-betagalactopyransol-beta-glucopyranoside, carboxyethylthioethyl 4-o-(4-o-[6-o-alpha-glucopyranosyl-alpha-glucopyranosyl]-alpha-glucopyranosyl)-beta-glucopyranoside, 4-o-(4-o-[6-o-beta-D-galactopyranosyl-beta-D-galactopyranosyl]-D-glucopyranose, carrageenan, D(+)cellobiose, D(+)cellopentaose, D(+)cellotetraose, D(+)cellotriose, cellulose, cellulose caprate, cellulose carbonate, chitin, chitobiose, chitosan, chitotriose, alpha-chloroalose, beta-chloroalose, 6-chloro-6-deoxy-alpha-glucopyranose, chondroitin sulfate, chondrosamine, chondrosine, chrysophanic acid, colominic acid, convallatoxin, alpha-cyclodextrine, beta-cyclodextrine, cytidine 5'-diphosphoglucose, cytosine 1-beta-arabinofuranoside, daunosamine, n-decyl-beta-glucopyranoside, 5-deoxyarabinose, 2-deoxy-2-fluoroglucose, 3-deoxy-3-fluoroglucose, 4-deoxy-4-fluoroglucose, 6-deoxygalactopyranose, 2-deoxygalactose, 1-deoxyglucohex-1-enopyranose tetrabenzoat, 2-deoxyglucose, 6-deoxyglucose, 2-deoxyglucose 6-phosphate, 1-deoxymannojerimycin, 6-deoxymannose, 1-deoxy-1-morpholinofructose, 1-deoxy-1-nitroalutol, 1-deoxy-1-nitroaltitol, 1-deoxy-1-nitrogalactitol, 1-deoxy-1-nitromannitol, 1-deoxy-1-nitrosorbitol, 1-deoxy-1-nitrotalitol, deoxynojirimycine, 3-deoxy-erythro-pentose, 2-deoxy-6-phosphogluconic acid, 2-deoxyribose, 3-deoxyribose, 2-deoxy-alpha-ribose 1-phosphate, 2-deoxyribose 5-phosphate, 5-deoxyxylofuranose, dextran, dextransulfate, dextrine, dextrose, diacetonefructose, diacetonemannitol, 3,4-di-o-acetyl-6-deoxyglucal, di-o-acetylrhamnal, 2,3-diamino-2,3-dideoxy-alpha-glucose, 6,9-diamino-2-ethoxyacridine lactate, 1,3:4,6-di-o-benzylidene mannitol, 6,6'-dideoxy-6,6'-difluorotrehalose, digalactosyl diglyceride, digalacturonic acid, (+)digitoxose, 6,7-dihydrocoumarin-9-glucoside, dihydroxyacetone, dihydroxyacetone phosphate, dihydroxyfumaric acid, dihydroxymalic acid, dihydroxytartaric acid, dihydrozeatinriboside, 2,3-diphosphoglycerolic acid, dithioerythritol, dithiothreitol, n-dodecyl beta-glucopyranoside, n-dodecyl beta-maltoside, dulcitol, elemigum, endotoxin, epifucose, erythritol, erythro-pentulose, erythrose, erythrose 4-phosphate, erythrulose, esculin, 17-beta-estradiol-3-glucuronide 17-sulfate, estriole glucuronide, estron beta-glucuronide, ethodin, ethyl 4-o-beta-D-galactopyranosyl)-beta-D-glucopyranoside, ethyl2-acetamido-4-o-(2-acetamido-2-deoxy-beta-glucopyranosyl)-6-o-(alpha-fucopyranosyl)-2-deoxy-beta-glucopyranoside, ethyl2-acetamido-2-deoxy-4-o-(4-o-alpha-galactopyranosyl-beta-galactopyranosyl)-beta-glucopyranoside, ethyl cellulose ethylene glycol chitin, ethyl 4-o-(4-o-alpha-galacto-pyranosyl-beta-galactopyranosyl)-beta-glucopyranoside, ethyl 4-o-beta-galactopyranosyl-beta-glucopyranoside, ethyl pyruvate, ethyl beta-thioglucoside, etiocholane-3alpha-ol-17-on glucuronide, ficoll, 6-fluoro-6-deoxyglucose, franguloside, fraxin, fructosazine, beta-(−)fructose, fructose-1,6-diphosphate, fructose-2,6-diphosphate, fructose-1-phosphate, fructose-6-phosphate, fucoidan, fucose, alpha-(−)-fucose-1-phosphate, fucosylamine, 2'-fucosyllactose, 3-fucosyllactose, fumaric acid, galactal, galactitol, galactopyranosylamine, 3-o-beta-galactopyranosyl-arabinose, 4-o-beta-galactopyranosyl-fructofuranose, 4-o-(4-o-beta-galactopyranosyl beta-galactopyranosyl)-glucopyranose, 4-o-alpha-galactopyranosyl-galactopyranose, 6-o-beta-galactopyranosylgalactose, 4-o-(beta-galactopyranosyl)-alpha-mannopyranose, alpha-galactopyranosyl 1-phosphate, galactopyranosyl-beta-thio-galactopyranoside, (+)galactosamine, alpha-galactosamine 1-phosphate, alpha-galactose 1-phosphate, galactose 6-phosphate, galactose 6-sulfate, 6-(alpha-galactosido)glucose, galacturonic acid, beta-gentiobiose, glucan, glucitol, glucoheptonic acid, glucoheptose, glucoheptulose, gluconate 6-phosphate, gluconic acid, 1-o-alpha-glucopyranosyl-beta-fructofuranoside, 6-o-alpha-glucopyranosylfructose, 1-o-alpha-glucopyranosyl-alpha-glucopyranoside, 4-o-beta-glucopyranosylglucopyranose, 4-o-(4-o-[6-o-alpha-glucopyranosyl-alpha-glucopyranosyl]-alpha-glucopyranosyl)glucopyranose, (+)glucosamine, alpha-glucosamine 6-2,3-disulfate, alpha-glucosamine 1-phosphate, glucosamine 6-phosphate, glucosamine 2-sulfate, alpha-glucosamine 3-sulfate, glucosamine 6-sulfate, glucosaminic acid, glucose, alpha-glucose 1,6-diphosphate, glucose 1-phosphate, glucose 6-phosphate, glucose 6-sulfate, glucuronamide, glucuronic acid, alpha-glucuronic acid 1-phosphate, glyceraldehyde, glyceraldehyde 3-phosphate, glycerate 2,3-diphosphate, glycerate 3-phosphate, glyceralic acid, alpha-glycerophosphate, beta-glycerophosphate, glycogen, glycolaldehyde, glycol chitosan, n-glycolylneuraminic acid, glycyric acid, glyoxylic acid, guanosine, 5'-diphosphoglucose, gulose, gums (accroides, agar, arab, carrageenan, damar, elemi, ghatti, guaiac, guar, karaya, locust bonne, mast, pontianac, storax, tragacanth, xanthan), heparin and heparin-like substances (mesoglycan, sulodexide, etc.), heptakis(2,3,6-tri-o-methyl)-beta-cyclodextrin, heptanoyl-N-methylglucamide, n-heptyl beta-glucopyranoside, hesperidin, n-hexyl-beta-glucopyranoside, hyaluronic acid, 16-alpha-hydroxyestronglucuronide, 16-beta-hydroxyestron glucuronide, hydroxyethyl starch, hydroxypropylmethyl-cellulose, 8-hydroxyquinolin-beta-glucopyranoside, 8-hydroxyquinolin glucuronide, idose, (−)-idose, indole-3-lactic acid, indoxyl-beta-glucoside, epi-inositol, myo-inositol, myo-inositol bisphosphate, myo-inositol-1,2-cyl phosphate, scyllo-inositol, inositolhexaphosphate, inositolhexasulfate, myo-insoitol 2-monophosphate, myo-inositol trisphosphate, (q)-epi-inosose-2, scyllo-inosose, inulin, isomaltose, isomaltotriose, isosorbid dinitrate, 11-ketoandrosterone beta-glucuronide, 2-ketogluconic acid, 5-ketogluconic acid, alpha-ketopropionic acid, lactal, lactic acid, lactitol, lactobionic acid, lacto-N-tetraose, lactose, alpha-lactose 1-phosphate, lactulose, laminaribiose, laminnarine, levoglucosan, beta-levulose, lichenan, linamarine, lipopolysaccharides, lithiumlactate, lividomycine A, lyxose, lyxosylamine, maltitol, maltoheptaose, maltohexaose, maltooligosaccharide, maltopentaose, maltose, alpha-(+)maltose 1-phosphate, maltotetraose, maltotriose, malvidine-3,5-diglucoside, mandelonitril beta-glucoside, mandelonitril glucuronic acid, mannan, mannit, mannitol, mannitol 1-phosphate, alpha-mannoheptitol, mannoheptulose, 3-c-alpha-mannopyranosyl-mannopyranose, alpha(+)mannopyranosyl-1-phosphate, mannosamine, mannosan, mannose, A(+)mannose 1-phosphate, mannose 6-phosphate, (+)melezitose, A(+) melibiose, mentholglucuronic acid, 2-(3'-methoxyphenyl)-N-acetylneuraminic acid, methyl 3-o-(2-acetamido-2-deoxy-beta-galactopyranosyl)-alpha-galactopyranoside, methyl 4-o-(3-o-[2-acetamido-2-deoxy-4-o-beta-galactopyranosyl beta-glucopyranosyl]-beta-galactopyranosyl)-beta-glucopyranoside, methyl 2-acetamido-2-deoxy-beta-glucopyranoside, methyl3-o-(2-acetamido-2-deoxy-beta-glucopyranosyl)-beta-galactopyranoside, methyl6-o-(2-acetamido)-2-deoxy-beta-glucopyranosyl)-alpha-mannopyranoside, methyl acosaminide, methyl alpha-altropyranoside, methyl3-amino-3-deoxy-alpha-mannopyranoside, methyl beta-arabinopyranoside, methyl 4,6-o-benzylidene-2,3-di-o- toluenesulfonyl-alpha-galactopyranoside, methyl 4,6-o-benzylidene-2,3-di-o-p-toluenesulfonyl-alpha-glucopyranoside, methyl cellulose, methyl alpha-daunosaminide, methyl6-deoxy-alpha-galactopyranoside, methyl 6-deoxy-beta-galactopyranoside, methyl 6-deoxy-alpha-glucopyranoside, methyl 6-deoxy-beta-glucopyranoside, methyl 3,6-di-o-(alpha-mannopyranosyl)-alpha-mannopyranoside, 1-o-methyl-alpha-galactopyranoside, 1-o-methyl-beta-galactopyranoside, methyl 3-o-alpha-galactopyranosyl-alpha-galactopyranoside, methyl-3-o-beta-galactopyranosyl-beta-galactopyranoside, 4-o-(2-o-methyl-beta-galactopyranosyl)glucopyranose, methyl 4-o-beta-galactopyranosyl-beta-glucopyranoside, methyl-4-o-(beta-galactopyranosyl-alpha-mannopyranoside, 5—5-methylgalacto pyranose, methylgalactoside, n-methylglucamine, 3-o-methyl-alpha-glucopyranose, 1-o-methyl-alpha-glucopyranoside, 1-o-methyl-beta-glucopyranoside, alpha-methyl glucoside, beta-methyl glucoside, methyl glycol chitosan, methyl-alpha-mannopyranoside, methyl-2-o-alpha-mannopyranosyl-alpha-mannopyranoside, methyl 3-o-alpha-mannopyranosyl-alpha-mannopyranoside, methyl-4-o-alpha-mannopyranosyl-alpha-mannopyranoside, methyl 6-o-alpha-mannopyranosyl-alpha-mannopyranoside, methyl alpha-rhamnopyranoside, methyl alpha-ribofuranoside, methyl beta-ribofuranoside, methylbeta-thiogalactoside, methyl 2,3,5-tri-o-benzoyl-alpha-arabinofuranoside, 4-methylumbelliferyl2-acetamido-4,6-o-benzylidene-2-deoxy-beta-glucopyranoside, 4-methylumbelliferyl N-acetyl-beta-galactosaminide, 4-methylumbelliferyl N-acetyl-alpha-glucosaminide, 4-methylumbelliferyl-N-acetyl-beta-glucosaminide, 4-methylumbelliferyl-alpha-arabinofuranoside, 4-methylum-belli-feryl-alpha-arabinopyranoside, 4-methylum-belliferyl-beta-cellobioside, 4-methylumbelliferyl-beta-n,n'-diacetylchitobioside, 4-methylumbelliferyl alpha-fucoside, 4-methylumbelliferyl beta-fucoside, 4-methylumbelliferyl alpha-galactopyranoside, 4-methylumbelliferyl beta-galactopyranoside, 4-methylumbelliferyl alpha-galactoside, 4-methylumbelliferyl beta -glucopyranoside, 4-methylumbelliferyl alpha-glucoside, 4-methylumbelliferyl beta-glucoside, 4-methylumbelliferyl beta-glucuronide, 4-methylumbelliferyl beta-mannopyranoside, 4-methylum-belliferylbeta-n,n',n"-triacetylchitotriose, 4-methyl-umbelliferyl2,3,5-tri-o-benzyl-alpha-arabinofuranoside, 4-methylumbelliferyl beta-xyloside, methyl beta-xylopyranoside, 2-o-methylxylose, alpha-methylxyloside, beta-methylxyloside, metrizamide, 2'-monophosphoadenosine 5'-diphosphoribose, 2'-monophosphoinosine 5'-diphosphoribose, mucine, muraminic acid, naringine, sodium lactate, sodium polypectate, sodium pyruvate, neoagarobiose, neoagarohexaitol, neoagarohexaose, neoagarotetraose, beta-neocarrabiose, neocarrabiose 4/1-sulfate, neocarrahexaose (2/4,4/1,4/3,4/5)-tetrasulfate, neocarratetraose(4/1,4/3)-disulfate, neocarratetraose(4/1)-sulfate, neohesperidin, dihydrochalcon, neohesperidose, neuraminic acid, neuraminic acid beta-methylglycoside, neuramine-lactose, nigeran, nigerantetrasaccharide, nigerose, n-nonyl glucoside, n-nonylbeta-glucopyranoside, octadecylthio-ethyl 4-o-alpha-galactopyranosyl-beta-galactopyranoside, octadecylthioethyl 4-o-(4-o-[6-o-alpha-glucopyranosyl-alpha-glucopyranosyl]-alpha-glucopyranosyl)-beta-glucopyranoside, octanoyl n-methylglucamide, n-octyl alpha-glucopyranoside, n-octyl-beta-glucopyranoside, oxidised starch, pachyman, palatinose, panose, pentaerythritol, pentaerythritol diformal, 1,2,3,4,5-pentahydroxy, capronic acid, pentosanpolysulfate, perseitol, phenolphthalein glucuronic acid, phenolphthalein mono-beta-glucosiduron phenyl 2-acetamido-2-deoxy-alpha-galactopyranoside, phenyl2-acetamido-2-deoxy-alpha-glucopyranoside, alpha-phenyl-N-acetyl-glucosaminide, beta-phenyl N-acetyl-glucosaminide, phenylethyl beta-galactoside, phenyl beta-galactopyranoside, phenyl beta-galactoside, phenyl alpha-glucopyranoside, phenyl beta-gluco-pyranoside, phenyl alpha-glucoside, phenyl beta-glucoside, phenyl beta-glucuronide, beta-phenyllactic acid, phenyl alpha-mannopyranoside, beta-phenylpyruvic acid, phenyl beta-thiogalactopyranoside, phenyl beta-thiogalactoside, phospho(enol)pyruvate, (+)2-phosphoglyceric acid, (–)3-phosphoglyceric acid, phosphohydroxypyruvic acid, 5-phosphorylribose 1-pyrophosphate, phytic acid, poly-N-acetylglucosamine, polygalacturonic acid, polygalacturonic acid methyl ester, polypectate, sodium, polysaccharide, 5beta-pregnane-3alpha, 2oalpha-diol glucuronide, n-propyl4-o-beta-galactopyranosyl-beta-glucopyranoside, prunasine, psicose, pullulan, quinolyl-8beta-glucuronic acid, (+)raffinose, alpha-rhamnose, rhapontine, ribitol, ribonolacton, ribose, D-2-ribose, alpha-ribose 1-phosphate, ribose 2-phosphate, ribose 3-phosphate, ribose 5-phosphate, ribulose, ribulose-1,5-diphosphate, ribulose 6-phosphate, saccharic acid, saccharolactic acid, saccharose, salicin, sarcolactic acid, schardingers-alpha-dextrine, schardingers-beta-dextrine, sedoheptulosan, sedoheptulose 1,7-diphosphate, sialic acid, sialyllactose, sinigrine, sorbitol, sorbitol 6-phosphate, (+)-sorbose, (–)sorbose, stachyose, starch, storax, styrax, sucrose, sucrose monocaprate, tagatose, alpha-talose, (–)-talose, tartaric acid, testosterone-beta-glucuronide, 2,3,4,6-tetra-o-methyl-glucopyranose, thiodiglucoside, 1-thio-beta-galactopyranose, beta-thioglucose, 5-thioglucose, 5-thioglucose 6-phosphate, threitol, threose, (+)threose, (–)threose, thymidine 5'-diphosphoglucose, thymin 1-beta-arabinofuranoside, tragacanth, (+)trehalose, trifluorothymin, deoxyriboside, 3,3',5-trihydroxy-4'-methoxy-stilbene-3-o-beta-gluco-side, trimethylsilyl(+)arabinose, trimethylsilyldulcitol, trimethylsilyl-beta(–)fructose, trimethylsilyl(+)galactose, trimethylsilyl-alpha-(+)-glucose, trimethyl-silyl(+) mannitol, trimethylsilyl(+]rhamnose, trimethyl-silyl(–) sorbitol, trimethylsilyl(+)xylose, rac-1-o-tritylglycerol, (+)turanose, n-undecyl beta-gluco-pyranoside, uracil beta-arabinofuranoside, uridine 5'-diphospho-N-acetylglucosamine, uridine 5'-diphospho-galactose, uridine 5'-diphosphoglucose, uridine 5'-diphospho-glucuronic acid, uridine 5'-diphosphomannose, uridine 5'-diphosphoxylose, vancomycine, xanthan gum, xylane, xylite, xylitol, xylobiose, alpha-xylopyranosyl 1-phosphate, xylose, alpha-xylose 1-phosphate, xylose 5-phosphate, xylotriose, xylulose, xylulose 5-phosphate, yacca, zeatine riboside, zinclactate, zymosan A, etc.

Denotations desoxyribonucleic-(DNA) and ribonucleic acid (RNA) have their common meaning; preferably such DNA or RNA forms, or their antagonists, are used which have a particularly strong biological action.

at least one nucleotide, peptide, protein or a related compound;

Nucleotides, which can be effectively transported with the aid of transfersomes, encompass adenine, adenosine, adenosine-3',5'-cyclic monophosphate, N6,O2'-dibutyryl, adenosine-3',5'-cyclic monophosphate, N6,O2'-dioctanoyl, adenosine, n6-cyclohexyl, salts of adenosine-5'-diphosphate, adenosine-5'-monophosphoric acid, adenosine-5'-o-(3-thiotriphosphate), salts of adenosine-5'-triphosphate, 9-beta-D-arabinoturanosyladenine, 1-beta-D- arabinoturanosylcytosine, 9-beta-D-arabinoturanosylguanine, 9-beta-D-arabinoturanosylguanine 5'-triphosphate, 1-beta-D-arabinoturanosylthymine, 5-azacytidine, 8-azaguanine, 3'-azido-3'-deoxythymidine, 6-beniylaminopurine, cytidine phosphoramidite, beta-cyanoethyl diisopropyl, 249802cytidine-5'-triphosphate, 2'-deoxyadenosine, 2'-deoxyadenosine 5'-triphosphate, 2'-deoxycytidine, 2'-deoxycytidine 5'-triphosphate, 2'-deoxyguanosine, 2'-deoxyguanosine 5'-triphosphate, 2',3'-dideoxyadenosine, 2',3'-dideoxyadenosine 5'-triphosphate, 2',3'-dideoxycytidine, 2',3'-dideoxycytidine 5'-triphosphate, 2',3'-dideoxyguanosine, 2',3'-dideoxyguanosine 5'-triphosphate, 2',3'-dideoxyinosine, 2',3' dideoxy-thymidine, 2',3'-dideoxythymidine 5'-triphosphate, 2',3'-dideoxyuridine, N6-dimethylallyladenine, 5-fluoro-2'-deoxyuridine, 5-fluorouracil, 5-fluorouridin, 5-fluorouridine 5'-monophosphate, formycine A 5'-triphosphate, formycine B, guanosine-3'-5'-cyclic monophosphate, guanosine-5'-diphosphate-3'-diphosphate, guanosine-5'-o-(2-thiotriphosphate), guanosine-5'-o-(3'-thiotriphosphate), guanosine 5'-triphosphate, 5'-guanylylimidodiphosphate, inosine, 5-iodo-2'-deoxyuridine, nicotinamide-adenine dinucleotides, nicotinamide-adenine dinucleotides, nicotinamide-adenine dinucleotide phosphate, oligodeoxythymidylic acid, (p(dT)10), oligodeoiythymidylic acid (p(dT)12–18), polyadenylic acid (poly A), polyadenylic acid-oligodeoxythymidynic acid, polycytidylic acid, poly (deoxyadenyl-deoxiythymidylic acid, polydeoxyadenylic-acid-oligodeoxythymidynic acid, polydeoxythymidylic acid, polyinosine acid-polycytidylic acid, polyuridynic acid, ribonucleic acid, tetrahydrouridine, thymidine, thymidine-3',5'-diphosphate, thymidine phosphoramidite, beta-cyanoethyl diisopropyl, 606102 thymidine 5'-triphosphate, thymine, thymine riboside, uracil, uridine, uridine-5'-diphosphoglucose, uridine 5'-triphosphate, xanthine, zeatine, transeatine riboside, etc. Further suitable polymers are: poly(DA) ss, poly(A) ss, poly(C) ss, poly(G) ss, poly(U) ss, poly(DA)-(DT) ds, complementary homopolymers, poly (D(A-T)) ds, copolymers, poly(DG).(DC) ds, complementary homopolymers, poly (d(G-C)) ds copolymers, poly (d(L-C)) ds copolymers, poly(I)-poly(C) ds, etc. An oligopeptide or a polypeptide preferably contains 3–250, frequently 4–100, and very often 4–50 amino acids which are mutually coupled via amide-bonds. Suitable amino acids are usually of the alpha- and L-type; exceptions, however, such as in dermorphine are possible.

Peptides with a particularly high biological and/or therapeutic significance, and which can also be combined with transfersomes, are, for example, N-acetyl-Ala-Ala-Ala-, N-acetyl-Ala-Ala-Ala methyl ester, N-acetyl-Ala-Ala-Ala-Ala, N-acetyl-Asp-Glu, N-acetyl-Gly-Leu, Nalpha-Acetyl-Gly-Lys methyl ester acetate, acetyl-hirudine fragments, acetyl-5-hydroxy-Trp-5-hydroxy-Trp amide, des-acetyl-alpha-melanocyte stimulating hormone, N-Acetyl-Met-Asp-Arg-Val-Leu-Ser-Arg-Tyr, N-acetyl-Met-Leu-Phe, acetyl-muramyl-Ala-isoGln, N-acetyl-Phe-Tyr, N-acetyl-Phe-norLeu-Arg-Phe amide, N-acetyl-renine substrate tetradecapeptide, N-acetyl-transforming growth factor, adipokinetic hormone II, adjuvant peptide, adrenal peptide E, adrenocorticotropic hormone (ACTH 1–39, Corticotropine A) and its fragments such as 1–4 (Ser-Tyr-Ser-Met), 1–10 (Ser-Tyr-Ser-Met-Glu-His-Phe-Arg-Trp-Gly), 1–17, 1–24 and 1–39, 11–24, 18–39, Ala-Ala, beta-Ala-Ala, Ala-Ala-Ala, Ala-Ala-Ala methyl ester, Ala-Ala-Ala-Ala, Ala-Ala-Ala-Ala-Ala, Ala-Ala-Ala-Ala-Ala, Ala-Ala-Phe, 7-amido-4-methylcoumarin, Ala-Ala-Phe p-nitroanilide, Ala-Ala-Val-Ala p-nitroanilide, Ala-Arg-Pro-Gly-Tyr-Leu-Ala-Phe-Pro-Arg-Met amide, beta-Ala-Arg-Ser-Ala-Pro-Thr-Pro-Met-Ser-Pro-Tyr, Ala-Asn, Ala-Asp, Ala-Glu, Ala-gamma-Gln-Lys-Ala-Ala, Ala-Gly, beta-Ala-Gly, Ala-Gly-Glu-Gly-Leu-Ser-Ser-Pro-Phe-Tyr-Ser-Leu-Ala-Ala-Pro-Gln-Arg-Phe amide, Ala-Gly-Gly, Ala-Gly-Ser-Glu, Ala-His, beta-Ala-His, Ala-isoGln-Lys-Ala-Ala, Ala-Ile, Ala-Leu, beta-Ala-Leu, Ala-Leu-Ala, Ala-Leu-Ala-Leu, Ala-Leu-Gly, Ala-Lys, beta-Ala-Lys, Ala-Met, N-beta-Ala-1-methyl-His, Ala-norVal, Ala-Phe, beta-Ala-Phe, Ala-Phe-Lys 7-amido-4-methylcoumarin, Ala-Pro, Ala-Pro-Gly, Ala-sarcosine, Ala-Ser, Ala-Ser-Thr-Thr-Thr-AsN-Tyr-Thr, Ala-Ser-Thr-Thr-Thr-Asn-Tyr-Thr amide, Ala-Thr, Ala-Trp, beta-Ala-Trp, Ala-Tyr, Ala-Val, beta-Ala-Val, beta-Ala-Trp-Met-Asp-Phe amide, alytesine, amanitine, amastatine, angiotensine I (Asp-Arg-Val-Tyr-Ile-His-Pro-Phe-His-Leu), II II (Asp-Arg-Val-Tyr-Ile-His-Pro-Phe), III and related peptides, angiotensine II antagonist, angiotensine II receptor binding protein, angiotensine converting enzyme and its inhibitor (e.g. entipaine, bestatine, chymostatine, E-64, elastatinal, etc.) anserine, antide, aprotinine, arginine, vasopressine-Ala-Gly, Arg-Ala, Arg-Arg-Leu-Ile-Glu-Asp-Ala-Glu-Tyr-Ala-Ala-Arg-Gly, Arg-Asp, Arg-Glu, Arg-Gly, Arg-Gly-Asp, Arg-Gly-Asp-Ser, Arg-Gly-Asp-Ser-Pro-Ala-Ser-Ser-Lys-Pro, Arg-Gly-Glu-Ser, Arg-Gly-Phe-Phe-Tyr-Thr-Pro-Lys-Ala, Arg-His-Phe, Arg-Ile, Arg-Leu, Arg-Lys, Arg-Lys-Asp-Val-Tyr, Arg-Phe, Arg-Phe-Asp-Ser, Arg-Pro-Pro-Gly-Phe-Ser-Pro-Phe-Arg, Arg-Ser-Arg, Arg-Ser-Arg-His-Phe, Arg-Val, Asn-Pro-Asn-Ala-Asn-Pro-Asn-Ala, Asn-Pro-Asn-Ala-Asn-Pro-Asn-Ala-Asn-Pro-Asn-Ala, alpha-Asp-Ala, Asp-Ala-Glu-Asn-Leu-Ile-Asp-Ser-Phe-Gln-Glu-Ile-Val, Asp-Asp, alpha-Asp-Glu, alpha-Asp-Gly, beta-Asp-Gly, beta-Asp-His, Asp-Leu amide, beta-Asp-Leu, alpha-Asp-Lys, alpha-Asp-Phe amide, alpha-Asp-Phe, alpha-Asp-Phe methyl ester, beta-Asp-Phe methyl ester, alpha-Asp-Ser-Asp-Pro-Arg, Asp-Val, beta-Asp-Val, atrial natriuretic peptide, especially its fragments 1–32 and 5–28, atriopeptine I, II and III, auriculine A and B, beauvericine, beniotript, bestatine, N-benzylated peptides, big gastrine I, bombesine, (D-Phe12,Leu14) (Tyr4), (Lys3)-bombesine, (Tyr4)-bombesine, adrenal medulla docosapeptide and dodecapeptide, Bradykinine (Arg-Pro-Pro-Gly-Phe-Ser-Pro-Phe-Arg) and related peptides, Bradykinine potentiators, brain natriuretic peptide, buccaline, bursine, S-t-butyl-Cys, caeruleine, calcitonine, calcitonine gene related peptide I and II, calmoduline binding domain, N-carboxymethyl-Phe-Leu, N-((R,S)-2-carboxy-3-phenyl-propionyl)Leu, cardioactive peptides A and B, carnosine, beta-casomorphine, CD4, cerebelline, N-chloroacetyl-Gly-Gly, chemotactic peptides such as formylated substances, cholecystokinine fragments, e.g., cholecystokinine octapeptide, coherine etc.

Also worth mentioning are the collagen peptides, conicostatine, conicotropine releasing factor, conotoxin G1, M1, and GVIA, corticotropine-like intermediate lobe peptide, corticotropine releasing factor and related peptides, C-peptide, Tyr-C-peptide, cyclic calcitonine gene related peptides, cyclo(His-Phe-), cyclo(His-Pro-), cyclo(Leu-Gly-), cyclo(Pro-Gly-), Cys-Asp-Pro-Gly-Tyr-Ile-Ser-Arg amide, Cys-Gln-Asp-Ser-Glu-Thr-Arg-Thr-Phe-Tyr, DAGO, Delta-sleep inducing peptide, dermorphine, (Ser (Ac)7)-dermorphine, diabetes associated peptide and its amide, N-alpha, N-epsilon-diacetyl-Lys-Ala-Ala, N-2,4-dinitrophenyl-Pro-Gln-Gly-Ile-la-Gly-Gln-Arg, diprotine A, dynorphines such as dynorphine A (Tyr-Gly-Gly-Phe-Leu-Arg-Arg-Ile-Arg-Pro-Lys-Leu-Lys-Trp-Asp-sn-Gln), fragments 1–6 (leucine encephaline-Arg), 1–8, 1–13 or E-64, dynorphine B, ebelactones (e.g. A and B) ecarine, elastatinal, eledoisine and related peptides, alpha-, beta- und gamma-endorphine, endothelins, endorphines (e.g. alpha (=beta-Lipotropine 61–76), (Tyr-Gly-Gly-Phe-Met-Thr-Ser-Glu-Lys-Ser-Gln-Thr-Pro-Leu-Val-Thr), beta(=beta-Lipotropine 61–91) and other beta-lipotropine-fragments, encephaline and Leu-encephaline (Tyr-Gly-Gly-Phe-Leu) and related peptides, encephalinase inhibitors (e.g. epiamastatine, epibestatine, foroxymithine, leupeptine, pepstatine, Nle-Sta-Ala-Sta), eosinophilo-tactic tetrapeptide, epiamastatine, epibestatine, (Cys(Acm)20,31)-epidermal growth factor and its fragments or receptors, epidermal mitosis inhibiting pentapeptide, trans-epoxysuccinyl-Leu amido-(4-guanidino)butane, erythropoietine and fragment, S-ethylglutathione, fibrinogen related peptide, fibrinopeptide A and B, Tyr-fibrinopeptide A, (Glu1)-fibrinopeptide S, fibrinopeptide B-Tyr, fibroblast growth factor fragment 1–11, follicular gonadotropine releasing peptide, N-formylated peptides, foroxymithine, N-(3(2-furyl)acryloyl) peptide derivatives, galanine, GAP 1–13, gastric inhibitory polypeptide, gastrine related peptides and derivatives, gastrine releasing peptide, gastrointestinal peptides (e.g. Ala-Trp-Met-Asp-Phe-Amid, bombesine, caeruleine, cholecystokinine, gelanine, gastrine, glucagon, motiline, neuropeptide K, pancreatic polypeptide, pancreozymine, Phi-27, secretine, valosine, etc.), Gln-Ala-Thr-Val-Gly-Asp-Val-Asn-Thr-Asp-Arg-Pro-Gly-Leu-Leu-Asp-Leu-Lys, (des-His1, Glu9)-glucagon amide, glucagon (1–37), glucagon-like peptide I, alpha-Glu-Ala, Glu-Ala-Glu, Glu-Ala-Glu-Asn, alpha-Glu-Glu, gamma-Glu-Glu, gamma-Glu-Gln, gamma-Glu-Gly, PGlu-Gly-Arg-Phe amide, alpha-Glu-Gly-Phe, gamma-Glu-His, gamma-Glu-Leu, alphaGlu-alpha-Lys, gamma-Glu-epsilon-Lys, N-gamma-Glu-Phe, PGlu-Ser-Leu-Arg-Trp amide, alpha-Glu-Trp, gamma-Glu-Trp, gamma-Glu-Tyr, alpha-Glu-Val, gamma-Glu-Val, PGlu-Val-Asn-Phe-Ser-Pro-Gly-Trp-Gly-Thr amide, A-Glu-Val-Phe, glutathiones and related peptides, glutathionesulfonic acid, Gly-Ala, Gly-beta-Ala, Gly-Ala-Ala, Gly-Ala-Ala-Ala-Ala, Gly-Ala-Tyr, Gly-alpha-aminobutyric acid, Gly-gamma-aminobutyric acid, Gly-Arg-Ala-Asp-Ser-Pro-Lys, Gly-Arg-Ala-Asp-Ser-Pro-OH, Gly-Arg-Gly-Asp-Ser, Gly-Arg-Gly-Asp-Asn-Pro-OH, Gly-Arg-Gly-Asp-Ser-OH, Gly-Arg-Gly-Asp-Ser-Pro-Lys, Gly-Arg-Gly-Asp-Ser-Pro-OH, Gly-Arg-Gly-Asp-Thr-Pro, Gly-Arg-Gly-Asp-Thr-Pro-OH, Gly-Arg p-nitroanilide, Gly-Arg-Gly-Asp, Gly-Arg-Gly-Asp-Ser, Gly-Asn, Gly-Asp, Gly-Asp-Asp-Asp-Asp-Lys, Gly-Glu, Gly-Gly and their derivatives such as methyl, ethyl or benzyl esters or amides, Gly-Gly-Ala, Gly-Gly-Arg, Gly-Gly-Gly, Gly-Gly-Gly-Gly, Gly-Gly-Gly-Gly-Gly, Gly-Gly-Gly-Gly-Gly-Gly, Gly-Gly-Ile, Gly-Gly-Leu, Gly-Gly-Phe, Gly-Gly-Phe-Leu, Gly-Gly-Phe-Leu amide, Gly-Gly-Phe-Met, Gly-Gly-Phe-Met amide, Gly-Gly-sarcosine, Gly-Gly-Tyr-Arg, Gly-Gly-Val, Gly-His, Gly-His-Arg-Pro, Gly-His-Gly, Gly-His-Lys, Gly-His-Lys-OH, Gly-Ile, Gly-Leu amide, Gly-Leu, Gly-Leu-Ala, Gly-Leu-Phe, Gly-Leu-Tyr, Gly-Lys, Gly-Met, Gly-norLeu, Gly-norVal, Gly-Phe amide, Gly-Phe, Gly-Phe-Ala, Gly-Phe-Arg, Gly-Phe-Leu, Gly-Phe-Phe, Gly-Pro, Gly-Pro-Ala, Gly-Pro-Arg, Gly-Pro-Arg-Pro, Gly-Pro-Arg-Pro-OH, Gly-Pro-Gly-Gly, Gly-Pro-hydroxy-Pro, Gly-sarcosine, Gly-Ser, Gly-Ser-Phe, Gly-Thr, Gly-Trp, Gly-Tyr amide, Gly-Tyr, Gly-Tyr-Ala, Gly-Val, Gly-Phe-Ser, granuliberine R, growth hormone releasing factor and its fragments, Hexa-Ala, Hexa-Gly, Hippuryl-Arg (Hip-Arg), Hippuryl-Gly-Gly (Hip-Gly-Gly), Hippuryl-His-Leu (Hip-His-Leu), Hippuryl-Lys, Hippuryl-Phe, hirudine and its fragments, His-Ala, His-Gly, His-Leu, His-Leu-Gly-Leu-Ala-Arg, His-Lys, His-Phe, His-Ser, His-Tyr, HIV envelope protein (gp120), Hydra peptides, P-hydroxyhippuryl-His-Leu, hypercalcemia malignancy factor (1–40), insulin chains B and C, P-iodo-Phe, Ile-Asn, Ile-Pro-Ile, insulin-like growth factor I (especially fragment 1–70), insulin-like growth factor II (especially its fragment 33–40), interleukin-1B fragment 163–171, isotocine, kassinine (Asp-Val-Pro-Lys-Ser-Asp-AGly-n-Phe-Val-Gly-Leu-Met-NH$_2$) katacalcine (calcitonine precursor peptide), Tyr-katacalcine, kemptide, kentsine, kyotorphine, laminine nonapeptide, laminine pentapeptide, laminine pentapeptide amide, leucine encephaline and related peptides, leucopyrokinine, Leu-Ala, Leu-beta-Ala, Leu-Arg, Leu-Asn, leucokinine I (Asp-Pro-Ala-Phe-Asn-Ser-Trp-Gly-NH$_2$) and II, Leucine-encephaline amide (Leu-encephaline amide) and related peptides, Leu-Gly, Leu-Gly-Gly, Leu-Gly-Phe, Leu-Leu amide, Leu-Leu, Leu-Leu-Leu amide, Leu-Leu-Leu, Leu-Leu-Phe amide, Leu-Leu-Tyr, Leu-Lys-Lys-Phe-Asn-Ala-Arg-Arg-Lys-Leu-Lys-Gly-Ala-Ile-Leu-Thr-Thr-Met-Leu-Ala, Leu-Met, Leu-Met-Tyr-Pro-Thr-Tyr-Leu-Lys, Leu-Phe, Leu-Pro, Leu-Pro-Pro-Ser-Arg, Leu-Ser, Leu-Ser-Phe, Leu-Trp, Leu-Tyr, Leu-Val, leucotriene, Leu-Leu methyl ester, leupeptin, Leu-Ser-p-nitro-Phe-Nle-Ala-Leu methyl ester, beta-lipotropin fragments, litorine, luteinizing hormone releasing hormone and related peptides, lymphocyte activating pentapeptide, Lys-Ala, Lys-Ala 7-amido-4-methylcoumarin, Lys-Asp, Lys-Cys-Thr-Cys-Cys-Ala, Lys-Glu-Glu-Ala-Glu, Lys-Gly, Lys-Leu, Lys-Lys, Lys-Met, Lys-Phe, Lys-Pro-Pro-Thr-Pro-Pro-Pro-Glu-Pro-Glu-Thr, Lys-Serum thymic factor, Lys-Trp-Lys, Lys-Tyr-Trp-Trp-Phe amide, Lys-Val, macrophage inhibitory peptide (Tuftsine fragment 1–3, Thr-Lys-Pro), magainine I and II, mast cell degranulating peptide, mastoparane, alpha1-mating factor, Melanine-Concentrating Hormone, MCD peptide, alpha-, beta-, gamma-, and delta-melanocyte stimulating hormones and related peptides, melittine, mesotocine, Met-beta-Ala, Met-Asn-Tyr-Leu-Ala-Phe-Pro-Arg-Met amide, methionine encephaline and related peptides, Met-Ala, Met-Ala-Ser, Met-Asn, methionine-encephaline (Met-encephaline, Tyr-Gly-Gly-Phe-Met) and related peptides, methionine-encephaline amide (Met-Encephaline amide, Tyr-Gly-Gly-Phe-Met-NH$_2$) and related peptides, Met-Gln-Trp-Asn-Ser-Thr-Thr-Phe-His-Gln-Thr-Leu-Gln-Asp-Pro-Arg-Val-Arg-Gly-Leu-Tyr-Phe-Pro-Ala-Gly-Gly, Met-Glu, Met-Gly, Met-Leu, Met-Leu-Phe, Met-Lys, Met-Met, Metorphamide, Met-Phe, Met-Pro, Met-Ser, Met-Tyr-Phe amide, Met-Val, N-Methoxycarbonyl-Nle-Gly-Arg, P-nitroaniline, methoxysuccinyl-Ala-Ala-Pro-Val, methoxysuccinyl-Ala-Ala-Pro-Val 7-amido-4-methylcoumarin, Met-somatotropine, molluscan cardioexcitatory peptide, morphiceptine, (Val3)-morphiceptine, motiline, MSH-release inhibiting factor, myeline basic protein or its fragments, naphthyl-amide-derivatives of various peptides, beta-naphthyl-Ala-Cys-Tyr-Trp-Lys-Val-Cys-Thr amide, alpha-neoendorphine, beta-neoendorphine, alpha-neurokinin, neurokinin A, (substance K, neuromedin L) and B, neoendorphine (alpha: Tyr-Gly-Gly-Phe-Leu-Arg-Lys-Tyr-Pro, beta, etc.) neuromedin B, C, K, U8, U-25 etc., neurokinin A and B, neuropeptides K and Y, neurophysin I and II, neurotensine and related peptides, nitroanilide peptide derivatives, Nle-Sta-Ala-Sta, NorLeu-Arg-Phe amide, opioid peptides (e.g. adrenal peptide E, Ala-Gly-Glu-Gly-Leu-Ser-Ser-Pro-Phe-Trp-Ser-Leu-Ala-Ala-Pro-Gln-Arg-Phe-amides, casein fragments, casomorphine, N-CBZ-Pro-D-Leu, dermorphine, kyotorphine, morphiceptine (Tyr-Pro-Phe-Pro-NH2), meorphamide (Tar-Gly-Gly-Phe-Met-Arg-Arg-Val, adrenorphine), osteocalcin (esp. its fragment 7–19), oxytocine and related peptides, pancreastatine and its fragments, such as 33–49, pancreatic polypeptide, pancreozymin, parathyroid hormone or fragments thereof, especially 1–34 and 1–84, penta-Ala, penta-Gly, penta-Phe, pepstatin A, peptide YY, peptide T, phalloidin, Phe-Ala-Ala-p-nitro-Phe-Phe-Val-Leu 4-pyridylmethyl ester, Phe-Leu-Phe-Gln-Pro-Gln-Arg-Phe amide, Phe-Ala, Phe-Gly, Phe-Gly-Gly, Phe-Gly-Gly-Phe, Phe-Gly-Phe-Gly, Phe-Leu amide, Phe-Leu, Phe-Leu-Arg-Phe amide, Phe-Leu-Glu-Glu-Ile, Phe-Leu-Glu-Glu-Leu, Phe-Leu-Glu-Glu-Val, Phe-Met, Phe-Met-Arg-Phe amide, Phe-Phe, Phe-Phe-Phe, Phe-Phe-Phe, Phe-Phe-Phe-Phe-Phe, Phe-Pro, Phe-Ser-Trp-Gly-Ala-Glu-Gly-Gln-Arg, Phe-Tyr, Phe-Val, PHI-27, PHM-27, phosphoramidone, physalaemine (pGlu-Ala-Asp-Pro-Asn-Lys-Phe-Tyr-Gly-Leu-Met-NH2), preproencephaline fragment 128–140, pressinoic acid and related peptides, Pro-Asn, proctoline (Arg-Tyr-Leu-Pro-Thr), proencephaline, Pro-His-Pro-Phe-His-Phe-Phe-Val-Tyr-Lys, Pro-Ala, Pro-Arg 4-methoxy-beta-naphthylamide, Pro-Asp, proglumide, Pro-Gly, Pro-Gly-Gly, Pro-hydroxy-Pro, Pro-Ile, Pro-Leu, Pro-Leu-Gly amide, Pro-Met, Pro-Phe amide, Pro-Phe, Pro-Phe-Arg 7-amido-4-methylcoumarin, Pro-Phe-Gly-Lys, Pro-Trp, Pro-Tyr, Pro-Val, cyclic AMP dependent protein kinase and its inhibitors, PyroGlu-Ala-Glu, PyroGlu-Ala, PyroGlu-Ala-Glu, PyroGlu-Asn-Gly, PyroGlu-Gly-Arg p-nitroanilide, PyroGlu-His-Gly amide, PyroGlu-His-Gly, PyroGlu-His-Pro amide, PyroGlu-His-Pro, PyroGlu-Lys-Trp-Ala-Pro, ranatensine, renine substrate tetradecapeptide, N-(alpha-rhamnopyranosyloxyhydroxyphosphinyl) Leu-Trp, sarcosyl-Pro-Arg p-nitroanilide, sauvagine, sleep-inducing peptide (Trp-Ala-Gly-Gly-Asp-Ala-Ser-Gly-Glu), secretine and related peptides, Ser-Ile-Gly-Ser-Leu-Ala-Lys, Ser-Ser-Ser, serum thymic factor, Ser-Ala, Ser-beta-Ala, Ser-Asn, Ser-Asp, Ser-Asp-Gly-Arg-Gly, Ser-Glu, Ser-Gln, Ser-Gly, Ser-His, Ser-Leu, Ser-Met, Ser-Phe, Ser-Ser-Ser, Ser-Tyr, sleep inducing peptide, somastotine and related peptides (e.g. cyclo(p-Trp-Lys-Trh-Phe-Pro-Phe), steroido-genesis activator polypeptide, substance P (Arg-Pro-Lys-Pro-Gln-Gln-Phe-Phe-Gly-Leu-Met-NH2) and related peptides, N-succinyl-derivatives of various peptides, syndyphalin-20 (Tyr-D-Met (O)-Gly-Phe-ol), tentoxin, tetra-Ala, tetra-Gly, thiostrepton, DL-thiorphane (encephalinase inhibitor), Thr-beta-Ala, Thr-Asp, Thr-Leu, Thr-Lys-Pro-Arg, Thr-Ser, Thr-Ser-Lys, Thr-Tyr-Ser, Thr-Val-Leu, thymopoietin fragments, thymosin alpha1 and its fragments, thymus circulating factor, thyrocalicitonin, thyrotropin releasing hormone, tocinoic acid, tosylated peptides, transforming growth factors, Tri-Ala, Tri-Ala methyl ester, Trp-Ala, Trp-Ala-Trp-Phe amide, Trp-Glu, Trp-Gly, Trp-Gly-Gly, Trp-His-Trp-Leu-Gln-Leu, Trp-His-Trp-Leu-Gln-Leu-Lys-Pro-Gly-Gln-Pro-Met-Tyr, Trp-His-Trp-Leu-Ser-Phe-Ser-Lys-Gly-Glu-Pro-Met-Tyr, Trp-Leu, Trp-Met-Asp-Phe amide, Trp-norLeu-Arg-Phe amide, Trp-Phe, Trp-Trp, Trp-Tyr, Tuftsin (Thr-Lys-Pro-Arg) and its fragments, Tyr-Ala, Tyr-Ala-Gly, Tyr-Ala-Gly-Ala-Val-Val-Asn-Asp-Leu, Tyr-Ala-Gly-N-methyl-Phe 2-hydroxyethylamide, Tyr-Ala-Phe-Met amide, Tyr-Arg, Tyr-atriopeptin II, Tyr-Glu, Tyr-Gly, Tyr-Gly-Ala-Val-Val-Asn-Asp-Leu, Tyr-Gly-Gly, Tyr-Gly-Gly-Phe-Leu-Arg-Lys-Arg, Tyr-Gly-Gly-Phe-Met-Arg-Arg-Val amide, Tyr-Gly-Trp-Phe-Phe amide, Tyr-Leu, Tyr-Phe, Tyr-Phe-Met-Arg-Phe amide, Tyr-Phe-Phe amide, Tyr-Pro-Leu-Gly amide, Tyr-Pro-Phe-Pro amide, Tyr-Pro-Val-Pro amide, Tyr-Thr-Gly-Leu-Phe-Thr, Tyr-Tyr-Phe amide, Tyr-Trp-Ala-Trp-Phe amide, Tyr-Trp-Ala-Trp-Phe methylamide, Tyr-Tyr-Leu, Tyr-Tyr-Phe, Tyr-Tyr-Tyr, Tyr-Tyr-Tyr methyl ester, Tyr-Tyr-Tyr-Tyr-Tyr, Tyr-Val amide, Tyr-Val, Tyr-Val-Gly, Urodilatin, Urotensin II, Valosin, Val-Ala, Val-Ala p-nitroanilide, Val-Ala-Ala-Phe, Val-Asp, Val-Glu, Val-Gln, Val-Glu-Glu-Ala-Glu, Val-Glu-Ser-Ser-Lys, Val-Gly, Val-Gly-Asp-Gln, Val-Gly-Gly, Val-Gly-Ser-Glu, Val-Gly-Val-Ala-Pro-Gly, Val-His-Leu-Thr-Pro, Val-His-Leu-Thr-Pro-Val-Glu-Lys, Val-Leu, Val-Lys, Val-Met, Val-Phe, Val-Pro, Val-Pro-Asp-Pro-Arg, Val-Pro-Leu, Val-Ser, Val-Thr, Val-Trp, Val-Tyr, Val-Tyr-Val, Val-Val, vasoactive intestinal peptides and related peptides, vasopressin related peptides, vasotocin and related peptides, xenopsin, etc.

Extended polypeptides are normally called proteins, independent of their detailed conformation. In this description, this term denotes, by and large, an enzyme or a coenzyme, an adhesion- or a recognition molecule, such as a CAMP or an OMP or a lectin, a histocompatibility complex, such as MHC-I or MHC-II, or an immunoglobuline (antibody)-or any (bio)chemical or (molecular)genetic modification thereof. Particularly useful for the applications according to this invention are the (bio)chemical modifications in which individual proteins are substituted with apolar residues, such as an alkyl, acyl, alkenoyl, etc. chains; but this is not a stringent limitation.

An enzyme is a catalytically active protein. Enzymes are normally grouped according to their basic functions. The most important enzymes for this invention are (E.C. numbers are given in brackets):

Oxidoreductases, such as: alcohol dehydrogenase (1.1.1.1), alcohol dehydrogenase (NADP dependent) (1.1.1.2), glycerol dehydrogenase (1.1.1.6), glycerophosphate dehydrogenase (1.1.1.8), xylulose reductase (1.1.1.10), polyol dehydrogenase (1.1.1.14), sorbitol dehydrogenase (1.1.1.14), myo-inositol dehydrogenase (1.1.1.18), uridine 5'-diphosphoglucose dehydrogenase (1.1.1.22), glyoxalate reductase (1.1.1.26), lactate dehydrogenase (1.1.1.27), lactate dehydrogenase (1.1.1.28), glycerate dehydrogenase (1.1.1.29), beta-hydroxybutyrate dehydrogenase (1.1.1.30), beta-hydroxyacyl CoA dehydrogenase (1.1.1.35), malate dehydrogenase (1.1.1.37), malate enzyme (1.1.1.40), isocitric dehydrogenase (1.1.1.42), 6-phosphogluconate dehydrogenase (1.1.1.44), glucose dehydrogenase (1.1.1.47), beta-galactose dehydrogenase (1.1.1.48), glucose-6-phosphate dehydrogenase (1.1.1.49), 3alpha-hydroxysteroid dehydrogenase (1.1.1.50), 3beta-hydroxysteroid dehydrogenase (1.1.1.51), 3alpha,2beta-hydroxysteroid dehydrogenase (1.1.1.53), 3-phosphoglycerate dehydrogenase (1.1.1.95), fucose dehydrogenase (1.1.1.122), lactate dehydrogenase (cytochrome) (1.1.2.3), glucose oxidase (1.1.3.4), cholesterol oxidase (1.1.3.6), galactose oxidase (1.1.3.9), alcohol oxidase (1.1.3.13), glycolate oxidase (1.1.3.15), choline oxidase (1.1.3.17), glycerol-3-phosphate oxidase (1.1.3.21), xanthine oxidase (1.1.3.22), alcohol dehydrogenase (1.1.99.8), fructose dehydrogenase (1.1.99.11), formaldehyde dehydrogenase (1.2.1.1), formate dehydrogenase (1.2.1.2), aldehyde dehydrogenase (1.2.1.5), glyceraldehyde-3-phosphate dehydrogenase (1.2.1.12), gabase (1.2.1.16), pyruvate oxidase (1.2.3.3), oxalate oxidase (1.2.3.4), dihydroorotate dehydrogenase (1.3.3.1), lipoxidase (1.3.11.12), alanine dehydrogenase (1.4.1.1), glutamic dehydrogenase (1.4.1.3), glutamate dehydrogenase (NADP) (1.4.1.4), L-amino acid oxidase (1.4.3.2), D-amino acid oxidase (1.4.3.3), monoaminoxidase (1.4.3.4), diaminoxidase (1.4.3.6), dihydrofolate reductase (1.5.1.3), 5,10-methylenetetrahydrofolat dehydrogenase (1.5.1.5), saccharopine dehydrogenase NAD+ (1.5.1.7), octopine dehydrogenase (1.5.1.11), sarcosine oxidase (1.5.3.1), sarcosine dehydrogenase (1.5.99.1), glutathione reductase (1.6.4.2), ferridoxin-NADP+ reductase (1.6.7.1), NADPH-FMN oxidoreductase (1.6.99.1), cytochrome c reductase (1.6.99.3), NADH-fmn oxidoreductase (1.6.99.3), dihydropteridin reductase (1.6.99.7), uricase (1.7.3.3), diaphorase (1.8.1.4), lipoamide dehydrogenase (1.8.1.4), cytochrome oxidase (1.9.3.1), nitrate reductase (1.9.6.1), phenolase (1.10.3.1), ceruloplasmine (1.10.3.2), ascorbate oxidase (1.10.3.3), NADH peroxidase (1.11.1.1), catalase (1.11.1.6), lactoperoxidase (1.11.1.7), myeloperoxidase (1.11.1.7), peroxidase (1.11.1.7), glutathione peroxidase (1.11.1.9), chloroperoxidase (1.11.1.10), lipoxidase (1.13.1.12), protocatechuate 3,4-dioxygenase (1.13.11.3), luciferase (glowworm) (1.13.12.7), salicylate hydroxylase (1.14.13.7), p-hydroxybenzoate hydroxylase (1.14.13.2), luciferase (bacterial) (1.14.14.3), phenylalanine hydroxylase (1.14.16.1), dopamine-beta-hydroxylase (1.14.17.1), tyrosinase (1.14.18.1), superoxide dismutase (1.15.1.1), ferredoxine-NADP reductase (1.18.1.2), etc.. Transferases, such as: catecholic o-methyltransferase (2.1.1.6), phenylethanol-amine N-methyl-transferase (2.1.1.28), aspartate transcarbamylase (2.1.3.2), ornithine carbamyl-transferase (2.1.3.3), transketolase (2.2.1.1), transaldolase (2.2.1.2), choline acetyltransferase (2.3.1.6), carnitine acetyltransferase (2.3.1.7), phosphotransacetylase (2.3.1.8), chloroamphenicol acetyltranferase (2.3.1.28), kanamycine 6'-acetyltransferase (2.3.1.55), gentamicine acetyltransferase (2.3.1.60), transglutaminase (2.3.2.13), gamma-glutamyl transpeptidase (2.3.2.2), phosphorylase A (2.4.1.1), phosphorylase B (2.4.1.1), dextransucrase (2.4.1.5), sucrose phosphornase (2.4.1.7), glycogen synthase (2.4.1.11), uridine 6'-diphosphoglucuronyltransferase (2.4.1.17), galactosyl transferase (2.4.1.22), nucleoside phosphorylase (2.4.2.1), orotidine-5'-monophosphate pyrophosphorylase (2.4.2.10), glutathione s-transferase (2.5.1.18), glutamine-oxalate transaminase (2.6.1.1), glutamic-pyruvate transaminase (2.6.1.2), gabase (2.6.1.19), hexokinase (2.7.1.1), galactokinase (2.7.1.6), fructose-9-phosphate kinase (2.7.1.11), gluconate kinase (2.7.1.12), phosphoribulokinase (2.7.1.19), NAD kinase (nicotinamide adenine dinucleotide kinase) (2.7.1.23), glycerokinase (2.7.1.30), choline kinase (2.7.1.32), protein kinase (3':5'-cyclic-AMP dependent) (2.7.1.37), phosphorylase kinase (2.7.1.38), pyruvate kinase (2.7.1.40), fructose-9-phosphate kinase (pyrophosphate dependent) (2.7.1.50), acetate kinase (2.7.2.1), carbamate kinase (2.7.2.2), 3-phosphoglyceric phosphokinase (2.7.2.3), creatine phosphokinase (2.7.3.2), etc.

Transpeptidases, such as: esterase (3.1.1.1), lipase (3.1.1.3), phospholipase A (3.1.1.4), acetylesterase (3.1.1.6), cholinesterase, acetyl (3.1.1.7), cholineesterase, butyryl (3.1.1.8), pectinesterase (3.1.1.11), cholesterol esterase (3.1.1.13), glyoxalase ii (3.1.2.6), phosphatase, alkaline (3.1.3.1), phosphatase acid (3.1.3.2), 5'-nucleotidase (3.1.3.5), 3'-nucleotidase (3.1.3.6), glucose-6-phosphatase (3.1.3.9), fructose-1,6-diphosphatase (3.1.3.11), phytase (3.1.3.26), phosphodiesterase i (3.1.4.1), glycerophosphorylcholine (3.1.4.2), phospholipase C (3.1.4.3), phospholipase D (3.1.4.4), deoxyribonuclease I (3.1.4.5), deoxyribonuclease II (3.1.4.6), ribonuclease N1 (3.1.4.8), sphingomyelinase (3.1.4.12), phosphodiesterase 3':5'-cyclic (3.1.4.17), phosphodiesterase II (3.1.4.18), endonuclease (3.1.4.21), ribonuclease A (3.1.4.22), ribonuclease B (3.1.4.22), 3'-phosphodiesterase 2':3'-cyclic nucleotide (3.1.4.37), sulfatase (3.1.6.1), chondro-4-sulfatase (3.1.6.9), chondro-6-sulfatase (3.1.6.10), ribonuclease T2 (3.1.27.1), ribonuclease Ti (3.1.27.3), ribonuclease u2 (3.1.27.4), nuclease (3.1.30.1), nuclease, (from micrococces) (3.1.31.1), alpha-amylase (3.2.1.1), beta-amylase (3.2.1.2), amyloglucosidase (3.2.1.3), cellulase (3.2.1.4), laminarinase (3.2.1.6), dextranase (3.2.1.11), chitinase (3.2.1.14), pectinase (3.2.1.15), lysozyme (3.2.1.17), neuraminidase (3.2.1.18), alpha-glucosidase, maltase (3.2.1.20), beta-glucosidase (3.2.1.21), alpha-galactosidase (3.2.1.22), beta-galactosidase (3.2.1.23), alpha-mannosidase (3.2.1.24), beta-mannosidase (3.2.1.25), invertase (3.2.1.26), trehalase (3.2.1.28), beta-N-acetylglucosaminidase (3.2.1.30), beta-glucuronidase (3.2.1.31), hyaluronidase (3.2.1.35), betaxylosidase (3.2.1.37), hesperidinase (3.2.1.40), pullulanase (3.2.1.41), alpha-fucosidase (3.2.1.51), mycodextranase (3.2.1.61), agarase (3.2.1.81), endoglycosidase F (3.2.1.96), endo-alpha-N-acetylgalactosaminidase (3.2.1.97), NADase (nicotinamide adenine glycopeptidase) F (3.2.2.5), dinucleotidase (3.2.2.18), thiogluc (3.2.3.1), s-adenosylhomocystein-hydrolase (3.3.1.1), leucin-aminopeptidase, (from cytosol) (3.4.11.1), leucin-aminopeptidase, microsomale (3.4.11.2), pyro-glutamateaminopeptidase (3.4.11.8), carboxypeptidase a (3.4.12.2), carboxypeptidase B (3.4.12.3), prolidase (3.4.13.9), cathepsin C (3.4.14.1), carboxypeptidase W (3.4.16.1), carboxypeptidase A (3.4.17.1), carboxypeptidase B (3.4.17.2), alpha-chymotrypsin (3.4.21.1), betachymotrypsin (3.4.21.1), gamma-chymotrypsin (3.4.21.1), delta-chymotrypsin (3.4.21.1), trypsin (3.4.21.4), thrombin (3.4.21.5), plasmin (3.4.21.7), kallikrein (3.4.21.8), enterokinase (3.4.21.9), elastase from pancreas (3.4.21.11), protease (subtilisin) (3.4.21.14), urokinase (3.4.21.31), elastase from leucocytes (3.4.21.37), cathepsin B, (3.4.22.1), papain (3.4.22.2), ficin (3.4.22.3), bromo-elain (3.4.22.4), chymopapain (3.4.22.6), clostripain (3.4.22.8), proteinase A (3.4.22.9), pepsine (3.4.23.1), renine (3.4.23.4), cathepsin D (3.4.23.5), protease (aspergillopeptidase) (3.4.23.6), collagenase (3.4.24.3), collagenase (3.4.24.8), pinguinain (3.4.99.18), renine (3.4.99.19), urokinase (3.4.99.26), asparaginase (3.5.1.1), glutaminase (3.5.1.2), urease (3.5.1.5), acylase i (3.5.1.14), cholylglycine hydrolase (3.5.1.24), urease(ATP-hydrolyzing) (3.5.1.45), penicillinase (3.5.2.6), cephalosporinase (3.5.2.8), creatininase (3.5.2.10), arginase (3.5.3.1), creatinase (3.5.3.3), guanase (3.5.4.3), adenosine-deaminase (3.5.4.4), 5'-adenylate acid-deaminase (3.5.4.6), creatinine deiminase (3.5.4.21), anorganic pyrophosphatase (3.6.1.1), adenosine 5'-triphosphatase (3.6.1.3), apyrase (3.6.1.5), pyrophosphatase, nucleotide (3.6.1.9), etc.

Lyases, such as: pyruvate-decarboxylase (4.1.1.1), oxalate decarboxylase (4.1.1.2), oxalacetate decarboxylase (4.1.1.3), glutamic decarboxylase (4.1.1.15), ornithine decarboxylase (4.1.1.17), lysine decarboxylase (4.1.1.18), arginin decarboxylase (4.1.1.19), histidine decarboxylase (4.1.1.22), orotidine 5'-monophosphate decarboxylase (4.1.1.23), tyrosine decarboxylase (4.1.1.25), phospho(enol) pyruvate carboxylase (4.1.1.31), ribulose-1,5-diphosphate carboxylase (4.1.1.39), phenylalanine decarboxylase (4.1.1.53), hydroxymandelonitrilelyase (4.1.2.11), aldolase (4.1.2.13), N-acetylneuramine acid aldolase (4.1.3.3), etc. citrate lyase (4.1.3.6), citrate synthase (4.1.3.7), tryptophanase (4.1.99.1), isozymes of carbonic anhydrase (4.2.1.1), fumarase (4.2.1.2), aconitase (4.2.1.3), enolase (4.2.1.11), crotonase (4.2.1.17), delta-aminolevulinate dehydratase (4.2.1.24), chondroitinase ABC (4.2.2.4), chondroitinase AC (4.2.2.5), pectolyase (4.2.2.10), aspartase (4.3.1.1), histidase (4.3.1.3), phenylalanine ammonia-lyase (4.3.1.5), argininosuccinate lyase (4.3.2.1), adenylosuccinate lyase (4.3.2.2), glyoxalase II (4.4.1.5), isomerases, such as: ribulose-5'-phosphate 3-epimerase (5.1.3.1), uridine 5'-diphosphogalactose 4-epimerase (5.1.3.2), mutarotase (5.1.3.3), triosephosphate isomerase (5.3.1.1), phosphoriboisomerase (5.3.1.6), phosphomannose isomerase (5.3.1.8), phosphoglucose isomerase (5.3.1.9), tautomerase (5.3.2.1), phosphoglucomutase (5.4.2.2), ligases, e.g.: aminoacyl-tRNA synthetase (6.1.1 ), s-acetyl coenzyme A synthetase (6.2.1.1), succinic thiokinase (6.2.1.4), glutamine synthetase (6.3.1.2), pyruvate carboxylase (6.4.1.1), etc.

The following are, amongst others, referred to as proteases: aminopeptidase M, amino acid-arylamidase, bromoelaine, carboxypeptidase A, carboxypeptidase B, carboxypeptidase P, carboxypeptidase Y, cathepsine C, chymotrypsine, collagenases, collagenase/dispase, dispase, elastase, endoproteinase Arg-c, endoproteinase Asp-n sequencing grade, encloproteinase Glu-c (proteinase V8), endoproteinase Glu-c sequencing grade, endoproteinase Lys-c, endoproteinase Lys-c sequencing grade, endoproteinases, factor Xa, ficine, kallikrein, leucine-aminopeptidase, papaine, pepsine, plasmin, pronase, proteinase K, proteinase V8 (endoproteinase Glu-c), pyroglutamate-aminopeptidase, pyroglutamate-aminopeptidase, restriction protease factor Xa, subtilisine, thermolysine, thrombine, trypsine, etc.

A coenzyme according to this invention is any substance which supports enzyme activity. Amongst the biologically important coenzymes are, for example, acetyl-coenzyme A, acetylpyridine-adenine-dinucleotide, coenzyme A, flavine-adenine-dinucleotide, flavine-mononucleotide, NAD, NADH, NADP, NADPh, nicotinamide-mononucleotide, s-palmitoyl-coenzyme A, pyridoxal-5'-phosphoric acid, etc.

Another class of proteins, which are important in the context of this invention, are lectins. Plants, and sometimes also animal, tissues are suitable sources of lectins; particularly convenient sources are *Abrus pregatorius, Agarigus bisporus, Agrostemma githago, Anguilla anguilla, Arachis hypogaea, Artogarpus integrifolia, Bandeiraea simplicifolia* BS-I und BS-II, (*Griffonia simplicifolia*), *Banhlula purpurea, Caragana arborescens, Cicer arietinum, Canavalia ensiformis* (jack bean), Caragana arborescens (Siberian pea tree), Codium fragile (green algae), Concanavalin A (Con A), *Cytisus scoparius, Datura stramonium, Dolichos biflorus, Erythrina corallodendron, Euonymus europaeus, Gelonium multiflorum, Glycine max* (soy), *Griffonia simplicifolia, Helix aspersa* (garden snail), *Helix pomatia* (escargot), *Laburnum alpinum, Lathyrus odoratus, Lens culinaris* (lentil), *Limulus polyphemus, Lycopersicon esculentum* (tomato), *Lotus tetragonolobus, Luffa aegyptiaca, Maclura pomifera* (Osaga orange), *Momordica charantia* (bitter pear melon), *Naja mocambique* (*Mozambiquan cobra*), Naja Naja kaouthia, *Mycoplasma gallisepticum, Perseau americana* (avocado), *Phaseolus coccineus* (beans), *Phaseolus limensis, Phaseolus lunatus, Phaseolus vulgaris, Phytolacga americana, Pseudomonas aeruginosa* PA-I, *Pisum sativum* (pea), *Ptilota plumosa* (red algae), *Psophocarpus tetragonolobus* (winged bean), *Ricinus communis* (castor bean), *Robinia pseudoacacia* (false acacia, black locust), *Sambucus nigra* (clematis), *Saponaria officinalis, Solanum tuberosum* (potato), *Sophora japonica, Tetragonolobus purpureas* (winged or asparagus pea), (*Lotus tetragono lobus*), *Tritigum vulgaris* (wheat germ), *Ulex europaeus, Vicia faba, Vicia sativa, Vicia villosa, Vigna radiata, Viscum album* (mistle), *Wisteria floribunda*, etc.

Further interesting proteins are, e.g. the activator of tissue-plasminogen, insulin, kallikrein, keratin, kininogene, lactoterrin, laminarin, laminin, alpha2-macroglobuline, alpha1-microglobuline, F2-microglobuline, high density lipoproteins, basic myeline-protein, myoglobine, neurofilaments I, II, and III, neurotensine, oxytocine, pancreatic oncofoetal antigen, parvalbumin, plasminogen, platelet factor 4, pokeweed antiviral protein, porphobilinogen, prealbumin, prostate specific antigens, protamine sulfate, protein C, protein C activator, protein S, prothrombin, retinol binding protein, S-100 protein, pregnancy protein-1, serum amyloid A, serum amyloid P component, tenascine, testosterone-estradiol binding globuline, thioredoxine, thrombine, thrombocytine, beta-thromboglobuline, thromboplastine, microsomal antigen from thyroidea, thyroidea stimulating hormone, thyroxine binding globuline, transcortine, transferrine, ubiquitine, vimentine, vinculine, vitronectine, etc.

Some typical examples of human and animal hormones which can be used as agents according to the invention are, for example, acetylcholine, adrenaline, adrenocorticotropic hormone, angiotensine, antidiuretic hormone, cholecystokinine, chorionic gonadotropine, corticotropine A, danazol, diethylstilbestrol, diethylstilbestrol glucuronide, 13,14-dihydro-15-keto-prostaglandins, 1-(3',4'-dihydroxyphenyl)-2-aminoethanol, 5,6-dihydroxytryptamine, epinephrine, follicle stimulating hormone, gastrin, gonadotropin, β-hypophamine, insulin, juvenile hormone, 6-ketoprostaglandins, 15-ketoprostaglandins, LTH, luteinizing hormone releasing hormone, luteotropic hormone, α-melanocyte stimulating hormone, gamma-melanocyte stimulating hormone, 5-melanocyte stimulating hormone, noradrenaline, norepinephrine, oxytocine, parathyroid hormone, parathyroid substances, prolactine, prostaglandins, secretine, somatostatine, somatotropine (STH), thymosine alpha 1, thyrocalcitonine, thyroglobuline, thyroid stimulating hormone, thyrotropic hormone, thyrotropine releasing hormone, 3,3',5-triiodothyroacetic acid, 3,3',5'-triiodothyronine, TSH, vasopressine, etc.

Oestrogens are mostly steroid hormones with 18 carbon atoms and one unsaturated (aromatic) ring. Amongst the most important oestrogens are, for example, chlorotrianisene, diencestrole, diethylstilboestrole, diethylstilboestrol-dipropionate, diethylstilboestroldisulfate, dimestrole, estradiole, estradiolbenzoate, estradiolundecylate, estriolsuccinate, estrone, ethinglestradiole, nexoestrole, nestranole, oestradiolvalerate, oestriole and quinestrole.

Gestagenes are typically synthetic hormones, mainly with progesterone-like characteristics; the most important agents belonging to this class are allylestrenole, chloromadinonacetate, dimethisterone, ethisterone, hydroxyprogesteron-caproate, lynestrenole, medrogestone, medroxyprogesteron-acetate, megestrolacetate, methyloestrenolone, norethisterone, norethisterone-acetate, and norgestrel.

Agents can also be parts of a biological extract. As sources of biologically and/or pharmacologically active extracts, the following are worth-mentioning: for example, *Acetobacter pasteurianum, Acokanthera ouabaio cathel, Aesculus hippocastanum, Ammi visnaga Lam., Ampi Huasca, Apocynum Cannabium, Arthrobotrys superba* var. oligospora (ATCC 11572), *Atropa belladonna, Bacillus Lentus, Bacillus polymyxa, Bacillus sphaericus, Castilloa elastica cerv., Chondrodendron tomentosum* (Ampi Huasca), *Convallaria majalis*, Coronilla-enzymes, *Corynebacterium hoagii* (ATCC 7005), *Corynebacterium simplex, Curvularia lunata* (Wakker) Boadijn, *Cylindrocarpon radicola* (ATCC 11011), *Cynara scolymus,* Datura Metel, didymella, digilanidase, digitalis Lanata, digitalis purpurea, Duboisia, *Flavobacterium dehydrogenans, Fusarium exquiseti saccardo, Hyoscyamus niger,* Jaborandi-leaves (*P. microphyilus* Stapf), *Micromonosporapurpurea u.*

*echinospora, Paecilomyces varioti Bainier var. antibioticus, Penicillium chrysogenum Thom, Penicillium notatum Westling, Penicillium patulum, Rauwolfia serpentina Benth., Rhizopus arrhizus Fischer* (ATCC-11145), *Saccharomyces cerevisiae*, Schizomycetes ATCC-7063, *Scilla maritima L., Scillarenase, Septomyxa affinis* (ATCC 6737), *Silybuin marianum Gaertn., Streptomyces ambofaciens*, Strophantusgratus, Strophantus Kombe, *Thevetia peruviana, Vinca minor L., Vinca rosea*, etc.

Unless stated otherwise, all substances, surfactants, lipids, agents or additives with one or several chiral carbon atoms can be used either as a racemic mixture or in the form of optically pure enantiomers.

WORKING PRINCIPLE

The transport of agents through permeation barriers can be mediated by such carriers which fulfill the following basic criteria:

carriers should experience or create a gradient which drives them into or through a barrier, e.g. from the body surface into or through the skin, or from the surface of a leaf into the depth of a leaf, or from one side of a barrier to the other;
- the resistance to permeation which is felt by the carriers in the barrier should be as small as possible in comparison to the driving force;
- carriers should be capable of permeating in and/or through a barrier without thereby losing their associated agents in an uncontrollable manner.

Carriers, moreover, should preferably provide control of the distribution of agents, as well as over the effectiveness and temporal development of the agents action. They should be capable of bringing materials into the depth of and across a barrier, if so desired, and/or should be capable of catalyzing such a transport. Last but not least, such carriers should affect the range and depth of action as well as the type of cells, tissue parts, organs and or system parts which can be reached or treated, under suitable conditions at least.

In the first respect, chemical gradients are especially convenient for biological applications. Particularly suitable are the physico-chemical gradients, such as the pressure of (de)hydration pressure (humidity gradient) or a difference in concentration between the sites of application and action; however, electrical or magnetic fields as well as thermal gradients are also interesting in this respect. In technological applications, an externally applied pressure or existing hydrostatic pressure difference are also of importance.

In order to fulfill the second condition, carriers must be sufficiently 'fluid' at the microscopic scale; this enables them to easily cross the constrictions in the permeability barrier.

Permeation resistance is a decreasing function of the decreasing carrier size. But also the carrier driving force frequently depends on the size of the permeating particle, droplet or vesicle; when the driving pressure is size-independent, the corresponding force also typically decreases with decreasing carrier size. This causes the transfer effectiveness to be a complex function of the carrier size, often showing a maximum depending on the chosen carrier and/or agent composition.

In the case of molecular aggregates the permeation resistance is largely determined by the mechanical elasticity and deformability of the carrier, the viscosity of the total preparation being also important, however. The former must be sufficiently high, the latter low enough.

Size and, even better, deformability can serve as a criterion for the optimization of the supramolecular carriers according to this invention. As an indication of deformability, the capacity of individual carriers to form protrusions can be studied, as a function of all relevant system parameters. (In practical terms, it is often sufficient to investigate only such variables which come into question for a controllable application. The examples given in this application, therefore, only pertain to varying the concentrations of the edge active components and the absolute carrier concentration which affect the forced diminishment of the lipid vesicle or of vesicle permeation.) This is true e.g. for transcutaneous and transcuticular transport as well as for the transport of agents through the lung alveoly, into the hair, into gels, and the like.

With regard to the third requirement, the choice of the carriers, agents and additives, as well as the applied carrier dose or concentration all play some role. Low dose, in the majority of cases, gives rise to a predominantly surface treatment: poorly water-soluble substances in such case remain confined largely to the apolar region of a permeability barrier (such as in the epidermal membranes); agents which are highly soluble and can diffuse easily from the carriers can attain a distribution which is different from that of the carrier particles; for such substances, the permeability of a transfersomal membrane is also important. Edge active substances with a tendency to leave carriers and move into a barrier give rise to a locally variable carrier composition, etc. These interdependencies should be thought of and considered prior to each individual application. In the search for a set of conditions under which a simple carrier vesicle becomes a transfersome, the following rules of thumb can be used:

- At first, the conditions are determined under which the carrier vesicles are solubilized by the edge active substances. At this critical point the 'vesicles' are maximally deformable owing to the fact that they are permanently formed and deformed. At the same time, however, they are also unstable and incapable of holding and transferring water soluble substances.
- Next, the carrier composition or concentration is adapted by reducing the edge activity in the system to an extent which ensures the vesicle stability as well vesicle deformability to be sufficiently high; this also ensures the permeation capacity of such carriers to be satisfactory. The term stability in this application implies, on the one hand, a mechanical tendency of the carrier components to "stay together"; on the other hand, that the carrier composition during the transport, and in particular during the permeation process, does not change at all or not much. The position of the corresponding optimum which one is looking for hereby depends on many boundary conditions. The type of agent molecules also plays an important role in this. The smaller and the more hydrophilic the agent to be transported, the further the carrier system must be spaced from the solubilization point; the desired shelf life of carriers is also important: upon approaching the solubilization point, the tendency of transfersomes to form larger particles may increase and the carrier's storage capacity simultaneously decrease.
- Ultimately, the system parameters need to be optimized with respect to the envisaged modes and goals of a given application. Rapid action requires a high permeation capability; in order to achieve slow drug release, it is advantageous to ensure gradual penetration through the permeability-barrier and a correspondingly 'finely adjusted' membrane permeability; in order to reach deep regions, high doses are needed; in order to obtain a broad distribution, it is recommended to use carrier concentrations which are not too high.

This application describes some relevant properties of the transfersomes as carriers for the lipid vesicles. Most of the examples pertain to carriers made of phospholipids, but the general validity of conclusions is not restricted to this carrier or molecule class. The vesicle examples should only illustrate the requirements which should be fulfilled in order to attain penetration through permeability barriers, such as skin. Similar properties, moreover, ensure carrier transport across animal or human epidermis, mucosa, plant cuticle, inorganic membranes, etc.

The fact that the cells in a horny skin layer continuously merge with the watery compartments of subcutis is probably one reason for the spontaneous permeation of transfersomes through the 'pores' in this layer: during the permeation process transfersomes are propelled by the osmotic pressure. As an alternative, external pressures, such as an electroosmotic or hydrostatic pressure, however, can also be applied in addition.

Depending on the vesicle dose used, the dermally applied carrier particles can penetrate as deep as the subcutaneous layer. Agents can then be locally released, enriched in (the depth of) the application site, or forwarded to other tissues and body systems through a system of blood and lymph vessels, the precise drug fate being dependent on the carrier size, composition and formulation.

It is sometimes convenient to adjust the pH-value of a formulation immediately after it has been prepared or directly prior to an application. Such an adjustment should prevent the deterioration of individual system components and/or drug carriers under the conditions of initial pH; simultaneously, a physiological compatibility should be achieved. For the neutralization of carrier suspensions, physiologically tolerable acids or bases are most frequently used as well as buffers with a pH-value between 3–12, preferably 5 to 9 and most often 6–8, depending on the goal and site of application. Physiologically acceptable acids are, for example, diluted aqueous solutions of mineral acids, such as hydrochloric acid, sulfuric acid, or phosphoric acid, or organic acids, such as carboxyalkane acids, e.g. acetic acid. Physiologically acceptable bases are, for example, diluted sodium hydroxide, suitably ionized phosphoric acids, etc.

Formulation temperature is normally chosen to be well suited for the given substances; for aqueous preparations it is normally in the range of 0 to 95° C. Whenever possible, one should work in the temperature range 18–70° C.; particularly preferred are temperatures between 15 and 55° C. for the work with fluid chain lipids; the preferred temperature range for the lipids with ordered chains is from 45 to 60° C. Other temperature ranges are possible, however, most notably for the non-aqueous systems or preparations containing cryo- or heat-stabilizers.

If required by the sensitivity of one of the system components, transfersome formulations can be stored in cold (e.g. at 4° C.). It is, moreover, possible to make and keep them under an inert atmosphere, e.g. under nitrogen. Shelf-life, furthermore, can be extended if no substances with multiple bonds are used, and if the formulation is (freeze) dried, or if a kit of dry starting materials is dissolved or suspended and processed at the site of application only.

In the majority of cases, carriers are applied at room temperature. But applications at lower or higher temperatures are also possible, especially when synthetic substances are used.

Transfersomal preparations can be processed previously or at the site of application, as has been described, for example, in our previous German patent application P 40 26 833.0-43, and exemplified in several cases in the handbook on 'Liposomes' (Gregoriadis, G., Edits. CRC Press, Boca Raton, Fla., Vols 1–3, 1987), in the monography 'Liposomes as drug carriers' (Gregoriadis, G., Edits. John Wiley & Sons, New York, 1988), or in the laboratory manual 'Liposomes. A Practical Approach' (New, R., Oxford-Press, 1989). If required any suspension of drugs, moreover, can be diluted or concentrated (e.g. by per ultracentrifugation or ultrafiltration) immediately prior to a final application; additives can also be given into a preparation at this or a previous time. Upon any such manipulation, however, a possible shift of the permeation optimum for a given carrier preparation must be taken into account or prevented.

Transfersomes as described in this applications are well suited to be used as carriers of lipophilic substances, such as fat-soluble biological agents, therapeutics, poisons, etc. But it is quite likely that transfersomes used in combination with water soluble substances, especially when the molecular weight of the latter exceeds 1000 Dt, will be of even greater practical value.

Transfersomes, moreover, can contribute to the stabilization of substances which are sensitive to hydrolysis; they can improve carrier and drug distribution in the specimen and at the site of application and can also ensure a more favourable effect of the drug in time. Basic carrier ingredients can also bring advantages of their own. However, the most important carrier characteristics is the capability of transporting materials into and through a permeability barrier; this opens up a way for applications which prior to this discovery were not feasible.

The specific formulations as described in this invention have been optimized for the topical use on—or in the vicinity of—(a) permeability barrier(s). Particularly interesting barriers of this kind are skin and plant cuticle. (But formulations according to this invention are also well suited for the peroral (p.o) or parenteral (i.v. i.m. or i.p.) application, especially when edge active substances have been chosen in order to keep the drug loss at the site of application low.) Edge active substances which have a diminished activity, are degraded preferentially, are absorbed particularly efficiently or are diluted strongly at the site of application are especially valuable in this last respect.

In dermatology, application doses of up to 50, often up to 10 and very frequently less than 2.5 (or even less than 1 mg) of carrier substance are used per cm of skin surface, the given masses pertaining to the basic carrier substance. The optimal mass depends on the carrier composition, desired penetration depth and duration of action, as well as on the detailed application site. Application doses useful in agrotechnics are typically lower and frequently below 0.1 g pro $m^2$.

Depending on the goal of application, each formulation can also contain suitable solvents up to a total concentration which is determined by certain plausible physical (no solubilization or appreciable shift of penetration optimum), chemical (no lowering of stability), or biological and physiological (little adversary side effects) formulation requirements.

Quite suitable for this purpose are, for example, the unsubstituted or substituted, e.g. halogenated, aliphatic, cycloaliphatic, aromatic or aromatic-aliphatic hydrocarbons, such as benzol, toluol, methylene chloride or chloroform, alcohols, such as methanol or ethanol, propanediol, erithritol, short-chain alkane carboxylic acid esters, such as acetic acid acid alkylesters, such as diethylether, dioxan or tetrahydrofuran, or mixtures therof.

A survey of the lipids and phospholipids which can be used for the applications as described in this report in addition to the ones already mentioned is given, for example, in 'Form and function of phospholipids' (Ansell & Hawthorne & Dawson, eds.), 'An Introduction to the Chemistry and Biochemistry of Fatty Acids and Their Glycerides' of Gunstone and in other reference books. All implicitly and explicitly mentioned lipids and surfactants as well as other suitable edge active substances and their preparation are well known. A survey of available surfactants, together with the trademarks under which they are marketed by their manufacturers, is given in the annals 'Mc Cutcheon's, Emulsifiers & Detergents', Manufacturing Confectioner Publishing Co. An up-to-date compilation of the pharmaceutically acceptable agents is given, for example, in 'Deutsches Arzneibuch' (and in the annually updated list 'Rote Liste'); furthermore, in the British Pharmaceutical Codex, European Pharmacopoeia, Farmacopoeia Ufficiale della Repubblica Italiana, Japanese Pharmacopoeia, Nederlandse Pharmacopoeia, Pharmacopoeia Helvetica, Pharmacopée Française, The United States Pharmacopoeia, The United States NF, etc. A concise list of suitable enzymes can be found in the volume on 'Enzymes', 3rd Edition (M. Dixon and E. C. Webb, Academic Press, San Diego, 1979); more recent developments are described in the series 'Methods in Enzymology'. Many examples of the glycohydrate-binding proteins which could be interesting for the use in combination with carriers as described in this invention are quoted in 'The Lectins: Properties, Functions, and Applications in Biology and Medicine' (I. E. Liener, N. Sharon, I. T. Goldstein, Eds. Academic Press, Orlando, 1986) as well as in the corresponding special publications; substances which are particularly interesting for agrotechnical applications are described, for example, in 'The Pesticide Manual' (C. R. Worthing, S. B. Walker, Eds. British Crop Protection Council, Worcestershire, Englande, 1986, e.g. 8th edition) and in 'Wirkstoffe in Pflanzenschutz und Schädlingsbekämpfung', which is published by Industrie-Verband Agrar (Frankfurt); most commonly available antibodies are listed in the catalogue 'Linscott's Directory', the most important neuropeptides in 'Brain Peptides' (D. T. Krieger, M. J. Brownstein, J. B. Martin, Eds. John Wiley, New York, 1983), corresponding supplementary volumes (e.g. 1987) and other special journals.

Methods for the preparation of liposomes, which in the majority of cases can also be used for manufacturing transfersomes, are described, for example, in 'Liposome Technology' (Gregoriadis, Ed., CRC Press) or older books dealing with similar topics, such as 'Liposomes in Immunobiology' (Tom & Six, Eds., Elsevier), 'Liposomes in Biological Systems' (Gregoriadis & Allison, Eds., Willey), 'Targeting of Drugs' (Gregoriadis & Senior & Trouet, Plenum), etc. Corresponding patent publications also are a valuable source of relevant information.

The following examples are aimed at illustrating this invention without restricting it. All temperatures are in degrees Celsius, carrier sizes in nanometers, pressures in Pascal and other units in standard SI system.

Ratios and percentages are given in moles, unless otherwise stated.

DETAILED DESCRIPTION OF PREFERRED EMBODIMENTS

Examples 1–13

Composition:

| | |
|---|---|
| 250–372 mg | phosphatidylcholine from soy-bean (+95% = PC) |
| 187–34.9 mg | oleic acid (+99%) |
| 0.312–0.465 ml | ethanol, absolute |
| 10 mM | Hepes |

Preparation:

Increasing amounts of oleic acid were pipetted into different volumes of alcoholic PC-solutions containing 75 micromoles of lipid so as to create a concentration series with a lipid/surfactant ratio beginning with L/S=0.5 and increasing by 0.2 units in each step. Subsequently, each lipid sample was supplemented with 4.5 ml of sterile buffer solution and the mixtures were incubated at 4° C. for one day. When the pH value had to be adjusted by addition of 1 M NaOH, the first incubation period was followed by another incubation for 24 hours. In order to obtain a final liposome suspension, each sample was thoroughly mixed and filtered through a polycarbonate filter (0.45 micrometer) into a glass vial which was then kept closed at 4° C.

Characterization:

Permeation resistance is assumed to be proportional to the relative pressure needed to perform a secondary filtration through a 0.2 micrometer filter. In this report this resistance is given in relative units of 1 to 10.

Vesicle size is measured by means of dynamic light scattering at 33 degrees C, using a Malvern Zeta-Sizer instrument. For the analysis of correlation curves, a special variant of the software package "Contin" is employed.

In this experimental series all vesicle sizes are relatively independent of the total concentration of edge active substances, in the range of 300 through 350 nm.

Permeation:

Permeation resistance first increases with decreasing relative concentration of fatty acid in the transfersomes. This trend is not monotonous, however. At a lipid/surfactant-ratio of approx. 2, the liposome permeation capacity starts to increase; but it then decreases again until, for L/S above 3, the transfersomes have nearly lost their capability for passing through narrow constrictions. Vesicles with a lipid/surfactant molar ratio of 1/2 are nearly perfectly permeable, however. (A suspension with 8% lipid in such case can be filtered nearly as easily as pure water.). At this concentration ratio, which corresponds roughly to 30% of the solubilization dose of fatty acids in an alkaline suspension, liposomes thus appear to correspond to optimal transfersomes.

Specific data points (0) are shown in FIG. 1. Vesicles diameters were always measured after permeation experiments.

Examples 14–20:

Composition:

| | |
|---|---|
| 349–358 mg | phosphatidylcholine from soy-bean (+95% = PC) |
| 63.6–52.2 mg | oleic acid (+99%) |
| 10 mM | Hepes |

Preparation:

4.5 ml of buffer in each case are pipetted to a corresponding amount of lipids and fatty acids to create a concentration series with L/S=1.92 through 2.4 in the steps of 0.08 units each; the pH value is set to 7.2–7.3 by 1 M NaOH. Lipid suspension after an incubation for 6 days at 4° C. is treated by ultrasonication until vesicles with an average diameter of 0.8 micrometers are formed.

Permeation and Characterization:

Permeation resistance is determined as described in examples 1–13. Its value, as a function of the concentration of edge active substance in the system resembles the results of measurements 1–13. The resulting vesicles are somewhat larger than in the previous set of experiments, however, having diameters in the order of 500 nm. This can be explained by the relatively slow material flow during filtration.

Corresponding measured points are shown as (+) in FIG. 1.

Examples 21–31

Composition:

| | |
|---|---|
| 322.6–372 mg | phosphatidycholine from soy-bean (+95% = PC) |
| 96.8–34.9 mg | oleic acid (+99%) |
| 0.403–0.465 ml | ethanol, absolute |
| 10 mM | Hepes |
| 130 mM | NaCl, p.a. |

Preparation:

Preparation procedure used essentially corresponds to the one of examples 14–20. The main difference is that the electrolyte concentration in the present case was isotonic with blood.

Figure 2:
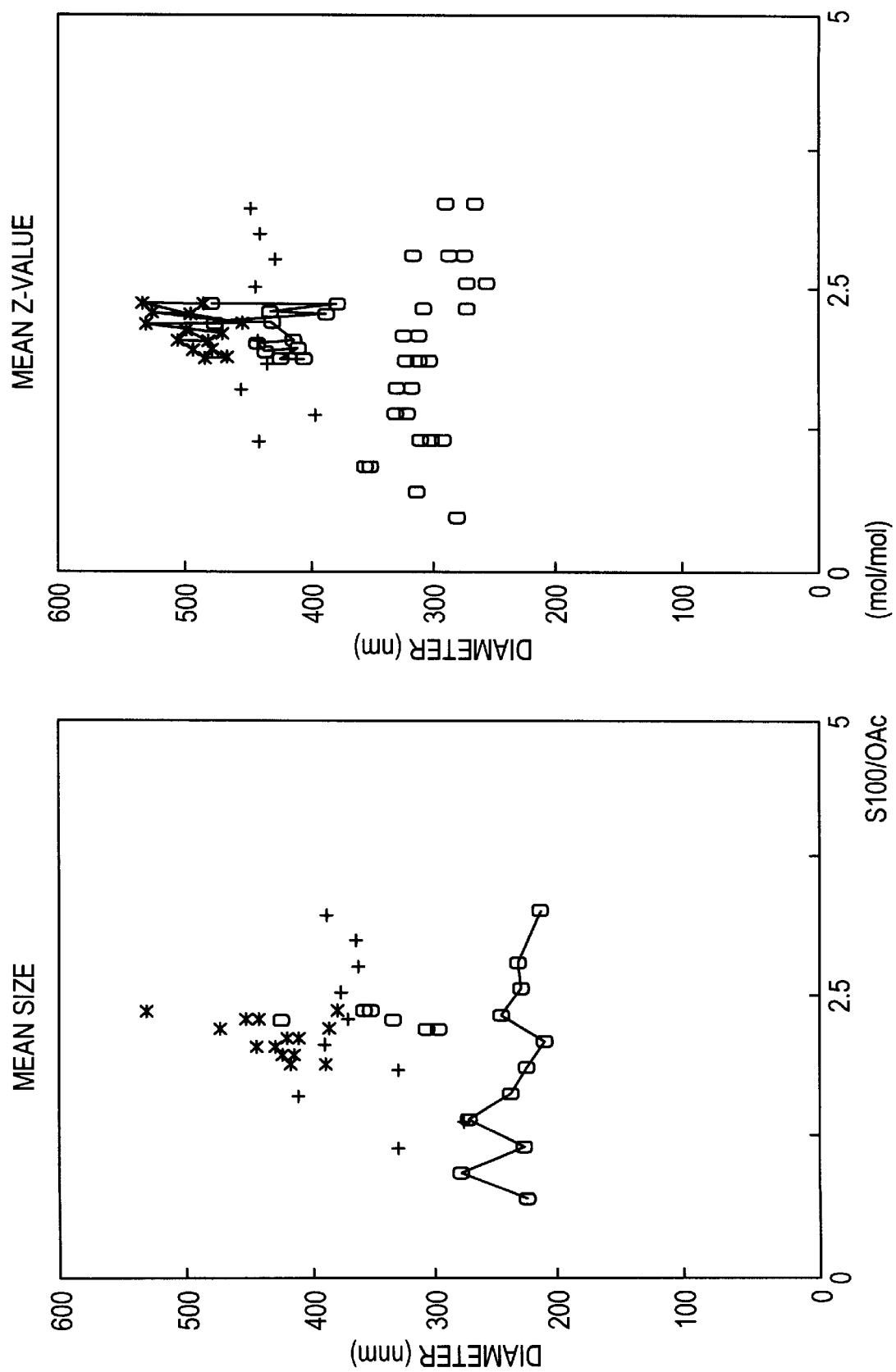
FIG. 2 is a graphical representation of the vesicle size data described in Examples 21–31.

Permeation and Characterization:

The measured permeation resistance corresponds, within the limits of experimental error, to the results given in examples 1–13. Vesicle sizes are also similar in both cases. Immediately after the lipid vesicle have been formulated, their diameters are in the range of 320–340 nm. 8 days later, however, the vesicle size has increased to approx. 440 nm. Corresponding experimental data is given in FIG. 2.

Examples 32–39

Composition:

| | |
|---|---|
| 184.5–199.8 mg | phosphatidylcholine from soy-bean (+95% = PC) |
| 20.5–22.2 mg | phosphatidylglycerol from egg PC (puriss., Na-salt, = PG) |
| 44.9–26.1 µl | oleic acid (+99%) |
| 0.165–0.178 ml | ethanol, absolute |
| 4.5 ml | Hepes, 10 mM |

Preparation:

Anhydrous PG is mixed with an alcoholic solution of PC to give a clear solution with 90% PC and 10% PG. Oleic acid is added to this solution; the resulting lipid/surfactant ratios are between 1.6 and 2.8; an isomolar specimen is made in addition to this. All mixtures are suspended in 4.5 ml of a sterile buffer solution to yield a final lipid concentration of 4% and then left for 3 days, after a pH-value adjustment with NaOH, in order to age.

Permeation and Carrier Characteristics:

For determining the permeation resistance, the same procedure as in examples 1–13 is used. All measured values are, as a rule, smaller than in the case of carriers which contained no charged species but had a similar L/S-ratio. Based on our experiments with a 4% suspension of PC and oleic acid we conclude that the relatively low total lipid concentration plays only a minor role in this respect.

As in previous examples, a resistance minimum is observed for the 4% PC/PG mixtures; this minimum, however, is found with L/S-ratios which are by some 20% higher than those measured with 8% lipid suspensions. Vesicle diameters, however, hardly differ from those measured in examples 1–13.

Figure 3:
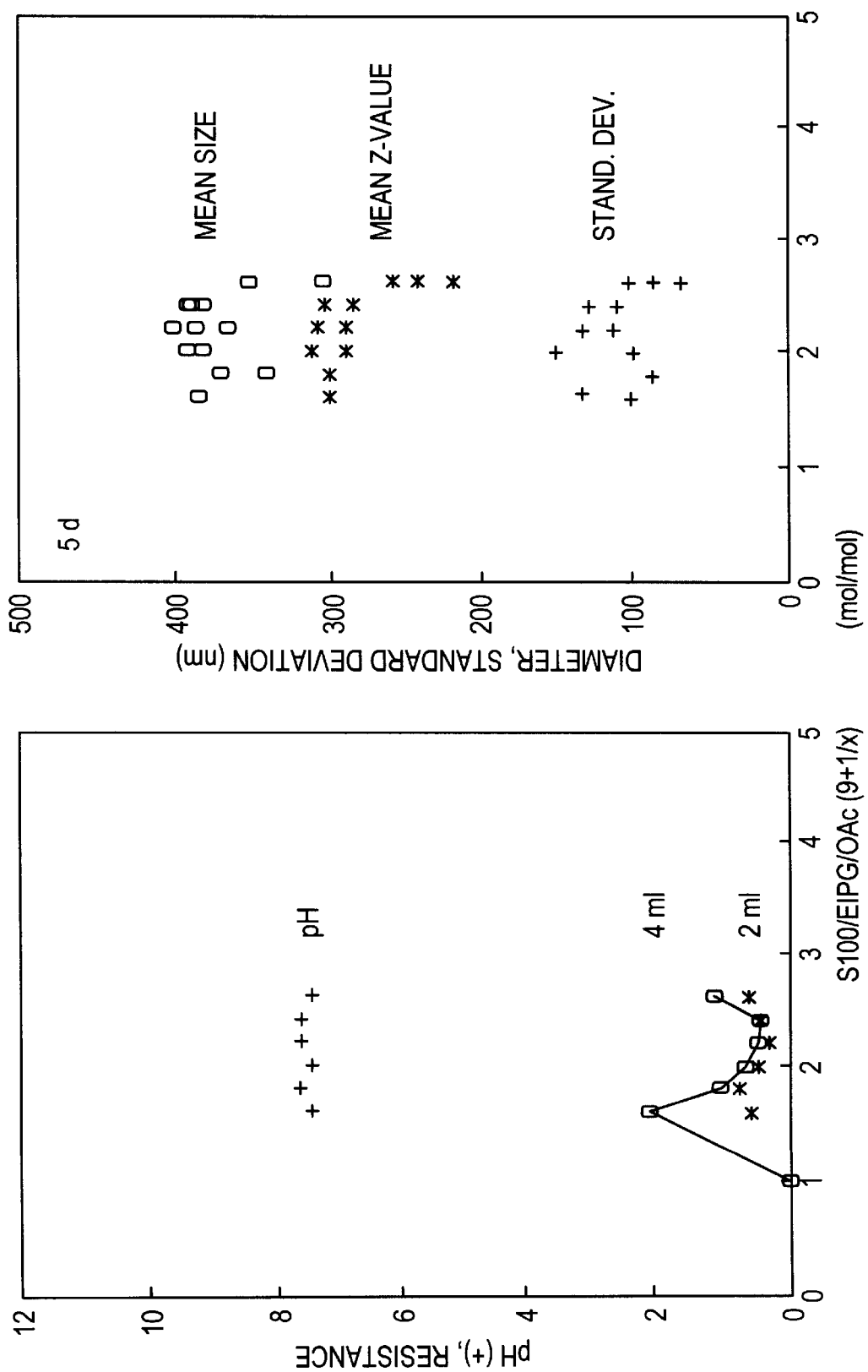
FIG. 3 is a graphical representation of the permeation resistance data and the vesicle size data desribed in Examples 32–39.
Figure 4:
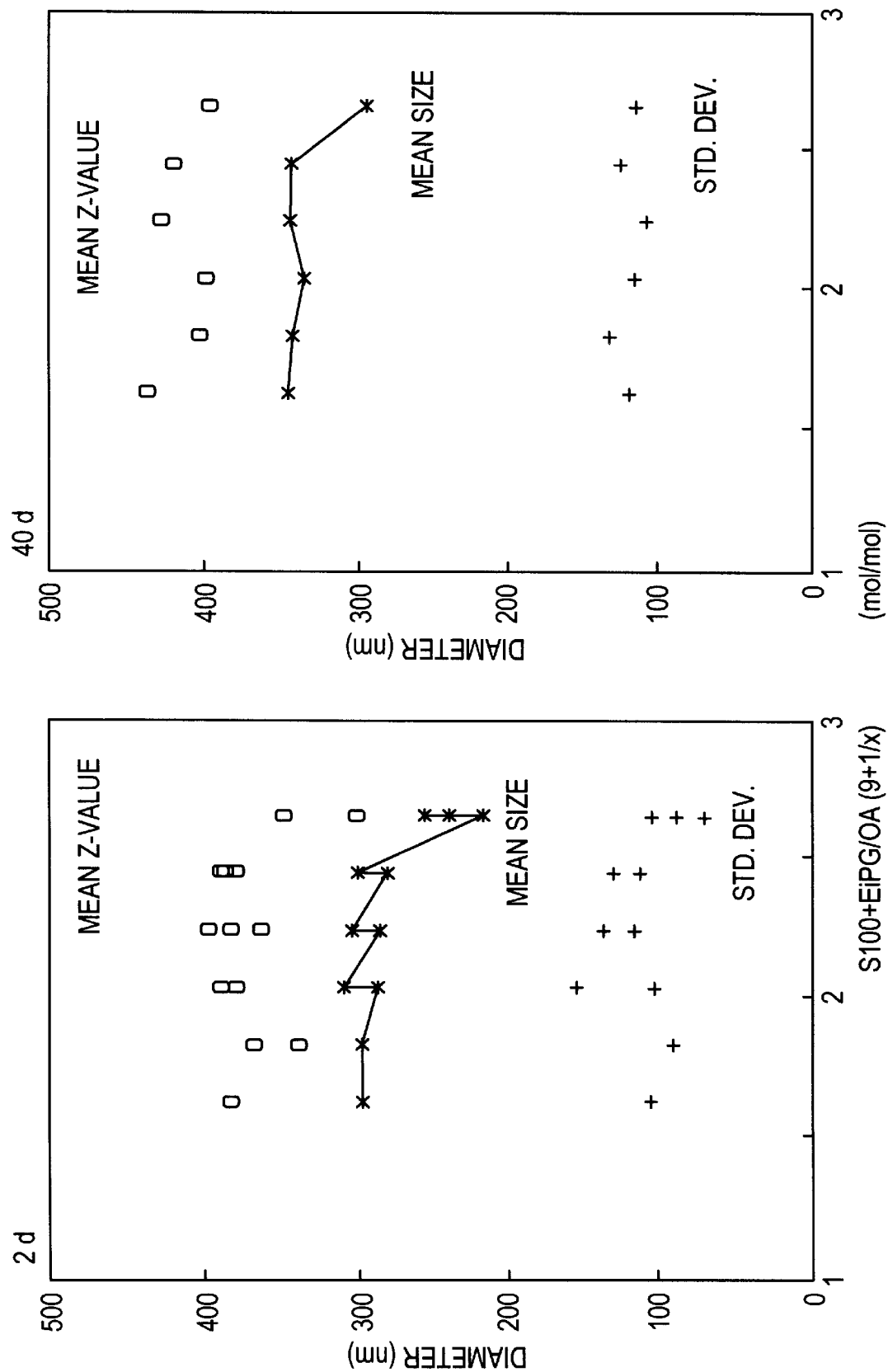
FIG. 4 is a graphical representation of the vesicle size data described in Examples 32–39.

Precise permeation data is shown in FIG. 3. All quoted diameters were measured immediately after individual permeation experiments. But even 40 days later, they are hardly bigger than at the beginning; FIG. 4 illustrates this.

Examples 40–49

Composition:

| | |
|---|---|
| 301.3–335.4 mg | phosphatidylcholine from soy-bean (+95% = PC) |
| 123.3–80.8 µl | Tween 80 (puriss.) |
| 0.38–0.42 ml | ethanol, absolute |
| 4.5 ml | phosphate buffer, isotonic, sterile |

Preparation:

Increasing volumes of Tween 80 are pipetted into appropriate volumes of an alcoholic PC solution. This gives rise to a concentration series with 12.5 through 25 mol-% surfactant (L/S=4–8). In addition to this, samples with L/S=2 and 3 are also made. After the addition of buffer, lipid vesicles are formed spontaneously: prior to further use, these are made somewhat smaller, with the aid of a 0.8 micrometer filter.

Permeation and Carrier Characteristics:

Permeation resistance is determined in the previously described manner. The corresponding values (0) are shown in the left part of FIG. 5. As in the case of transfersomes which contain oleic acid, a region of anomalously high permeation capability (at L/S=6) can be seen relatively far away from the solubilization point. But it is not before below L/S=4 that a maximum permeability is observed. The transfersomal optimum thus is located in a range which differs by a factor of 1.5–2 from the solubilization point.

Figure 5:
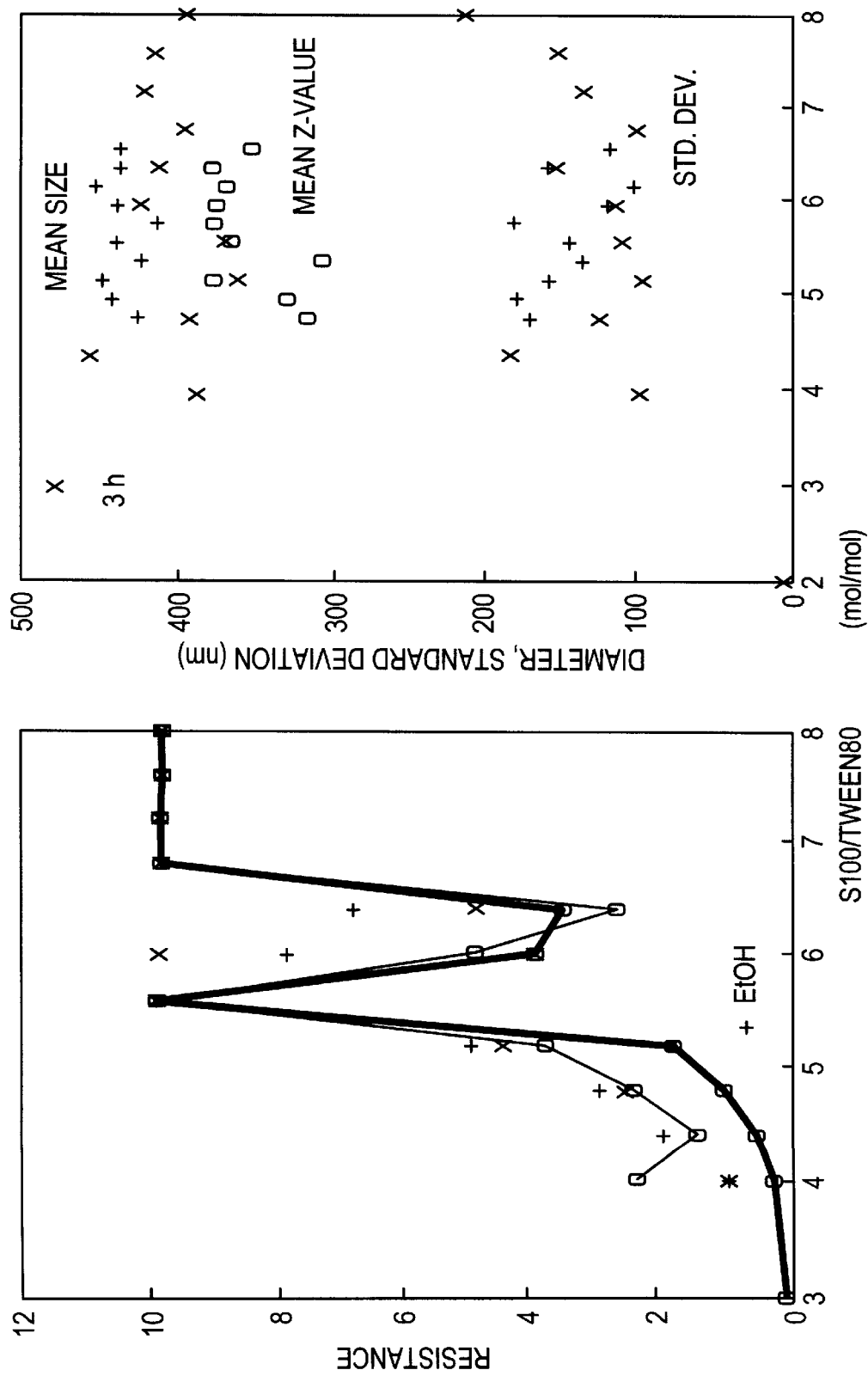
FIG. 5 is a graphical representation of the permeation resistance data and the vesicle size data described in Examples 40–49 and Examples 50–61.

Precise permeation data is given in FIG. 5 (wide lines, left panel). The experimental data in right panel documents the vesicle diameters determined after permeability measurements.

Examples 50–61

Composition:

| | |
|---|---|
| 314.2–335.4 mg | soy-bean phosphatidylcholine (+95% = PC) |
| 107.2–80.8 ml | Tween 80 (puriss.) |
| 4.5 ml | phosphate buffer, isotonic, sterile |

Preparation:

First Tween 80 and subsequently phosphate buffer are added to appropriate quantities of PC. The resulting mixture is agitated at room temperature for 4 days. The further procedure is as described in examples 40–49.

Permeation and Carrier Characteristics:

Corresponding permeability data is given in FIG. 5 (thin lines). It confirms, by and large, the results of experiments nos. 40–49.

Examples 62–75

Composition:

| | |
|---|---|
| 193–361 mg | phosphatidylcholine from soy-bean (grade I, S100) |
| 207.2–38.8 mg | Na-cholate, puriss. |
| 4.5 ml | phosphate buffer (isotonic with a physiologic solution) |
| | ethanol, absolute |

Preparation:

0.5 ml of a hot solution of S100 in ethanol (2/1, M/V) are mixed with sufficient amounts of bile acid salts which give rise to a concentration series with increasing lipid/surfactant ratio between 1/2 and 5/1. The final total lipid concentration is 8% in all cases.

Vesicle permeation through constrictions and vesicle solubilization:

The permeation resistance of each sample is measured as in examples 1–13. The vesicle size is determined by means of light scattering. (Radii of particles smaller than 5 nm cannot be measured owing to the insufficient power of the laser source used.)

Figure 6:
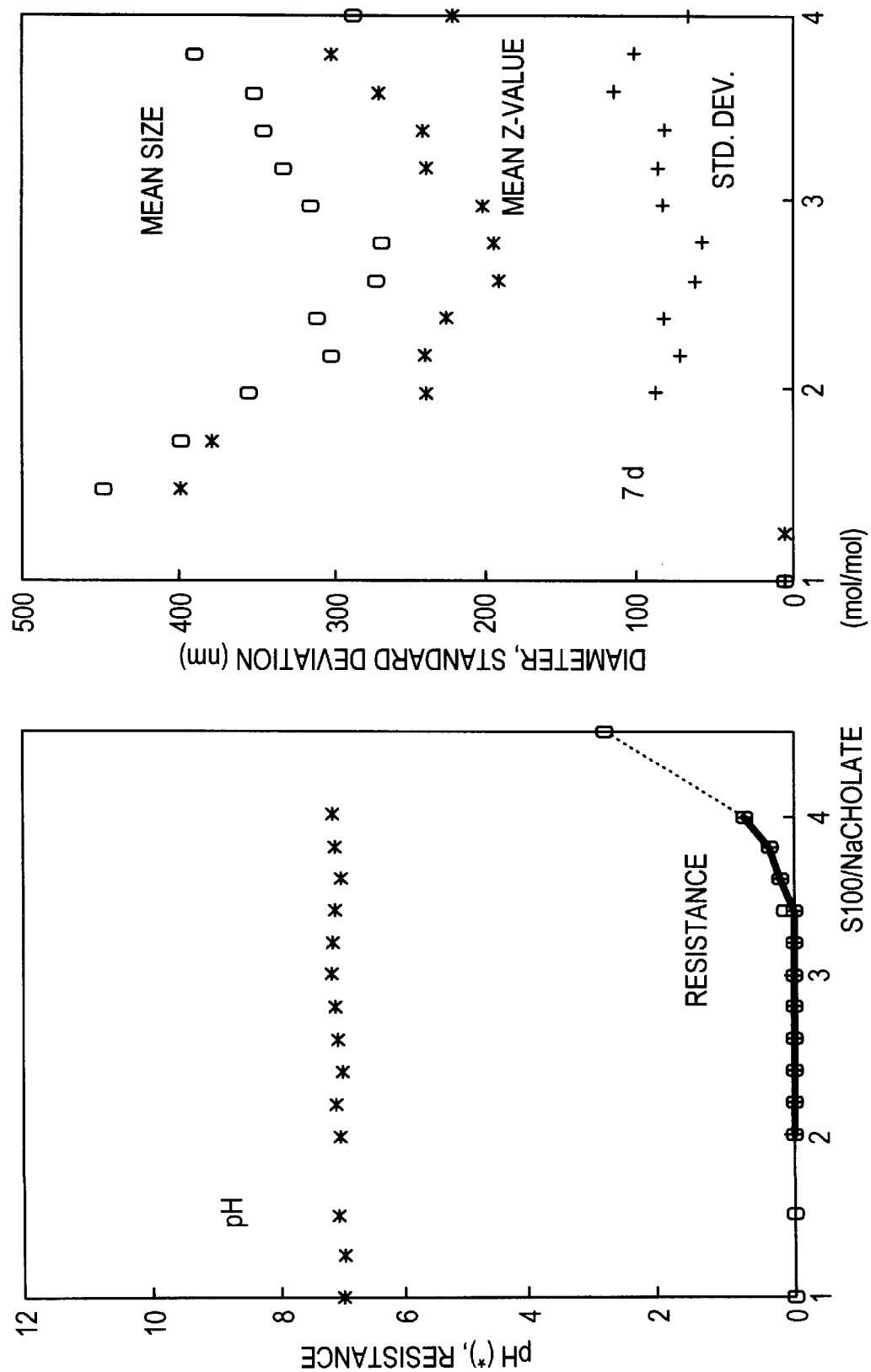
FIG. 6 is a graphical representation of the permeation resistance data and the vesicle size data described in Examples 62–75.

Corresponding measured data is shown in FIG. 6. It indicates that the permeation resistance of transfersomes with an L/S ratio below 3.5/1 is very small but that this resistance increases significantly at higher L/S values (left panel); the increase of the mean vesicle diameter above L/S=2.75 (right panel) is probably a consequence of the decreased flow (and thus of a diminished hydrodynamic shear) caused by the greater permeability resistance in this concentration range.

Within only a few hours after preparation the size of vesicles just above the solubilization limit (at L/S between 1.25/1 and 2.5/1) is significantly bigger than in the vicinity the 'transfersome optimum'. Such undesired consequences of surfactant activity (cf. Fromherz, P. in: 'Galstone disease, Pathophysiology and Therapeutic Approaches', pp. 27–33, Springer, Berlin, 1990) should always be taken into account. At L/S of approx. 1.25/1, solubilization sets in which leads to the formation of, in our case unmeasurably, small mixed micelles of a size of approximately 5 nm.

Examples 76–91

Composition:

| | |
|---|---|
| 1.627–0.5442 g | phosphatidylcholine from soy-bean (gradeI, S100) |
| 4.373–0.468 g | Na-cholate, puriss. |
| 60 ml | phosphate buffer (physiological) |

Preparation:

A 10% suspension of S100 in phosphate buffer is ultrasonicated at room temperature until the mean vesicle size is approx. 350 nm.

This suspension is divided into three equal volume parts containing 10%, 1% and 0.2% phospholipids. Starting with these preparations, aliquots containing 5 ml of suspension each are prepared. These are supplemented with increasing amounts of sodium cholate (partly in the form of a concentrated micelle suspension), yielding a concentration series with L/S ratios between 1/5 and 5/1. Prior to each permeation- and solubilization measurement, the starting suspension is aged for 1 week at 4° C.

Vesicle permeation through constrictions and vesicle solubilization:

In order to determine the permeation resistance of these samples two different procedures are used.

In the first series, each suspension is diluted prior to an actual measurement to get a final lipid concentration of 0.2%; subsequently it is pressed through a filter with a pore size of 0.1 micrometers. The sample resistance is identified with the inverse value of the volume which has passed through the filter pores during a period of 5 minutes.

In the second series, the permeation resistance is determined as in examples 1–13 and finally renormalized by dividing the values thus obtained with regard to the final lipid concentration.

The resulting data shows that both the solubilization limit and the position of a 'transfersome optimum' expressed in terms of preferred L/S ratios are dependent on the overall lipid concentration. In the case of a 10% suspension the corresponding values are approx. 1/1 and 2.75/1, respectively; for the 0.2% suspension they increase to 1/4 and 1/1, however.

Examples 92–98

Composition:

| | |
|---|---|
| 16.3–5.4 mg | phosphatidylcholine from soy-bean (Grade I, S100) |
| 41.5–5.5 mg | Na-desoxycholate, puriss. |
| 5 ml | phosphate buffer (physiological) |

Preparation:

A suspension of 1% desoxycholate containing vesicles is prepared as described in examples 76–91.

Vesicle permeation through constrictions and vesicle solubilization:

The measurements of this experimental series show that vesicles containing desoxycholate are solubilized already at L/S ratios near 1/2, i.e. at an L/S ratio which is by a factor of 2–3 lower than in the case of S100/Na-cholate vesicles.

Examples 99–107

Composition:

| 3 mM | Suspension of phosphatidylcholine from soy-bean (grade I, S100) in phosphate buffer Na-cholate, puriss. |
|---|---|

Preparation:

A 3 mM suspension of S100 in phosphate buffer is partly homogenized at room temperature. 3 ml of this suspension are supplemented each with increasing amounts of sodium cholate in order to create a series with increasing L/S ratios between 1/2 and 12/1. After three days of incubation, these aliquots are ultrasonicated at 55° C., using a 50% duty-cycle; simultaneously, the optical density at 400 nm of each sample is recorded. An analysis of the resulting experimental data within the framework of a bimodal exponential model reveals two characteristic vesicularization rates (tau 1 and tau 2); these characterize the temporal dependence of the number of lamellae in each vesicle (tau 1) and the changes in the mean size of vesicles (tau 2).

Vesicle characterization and deformability.

Figure 7:
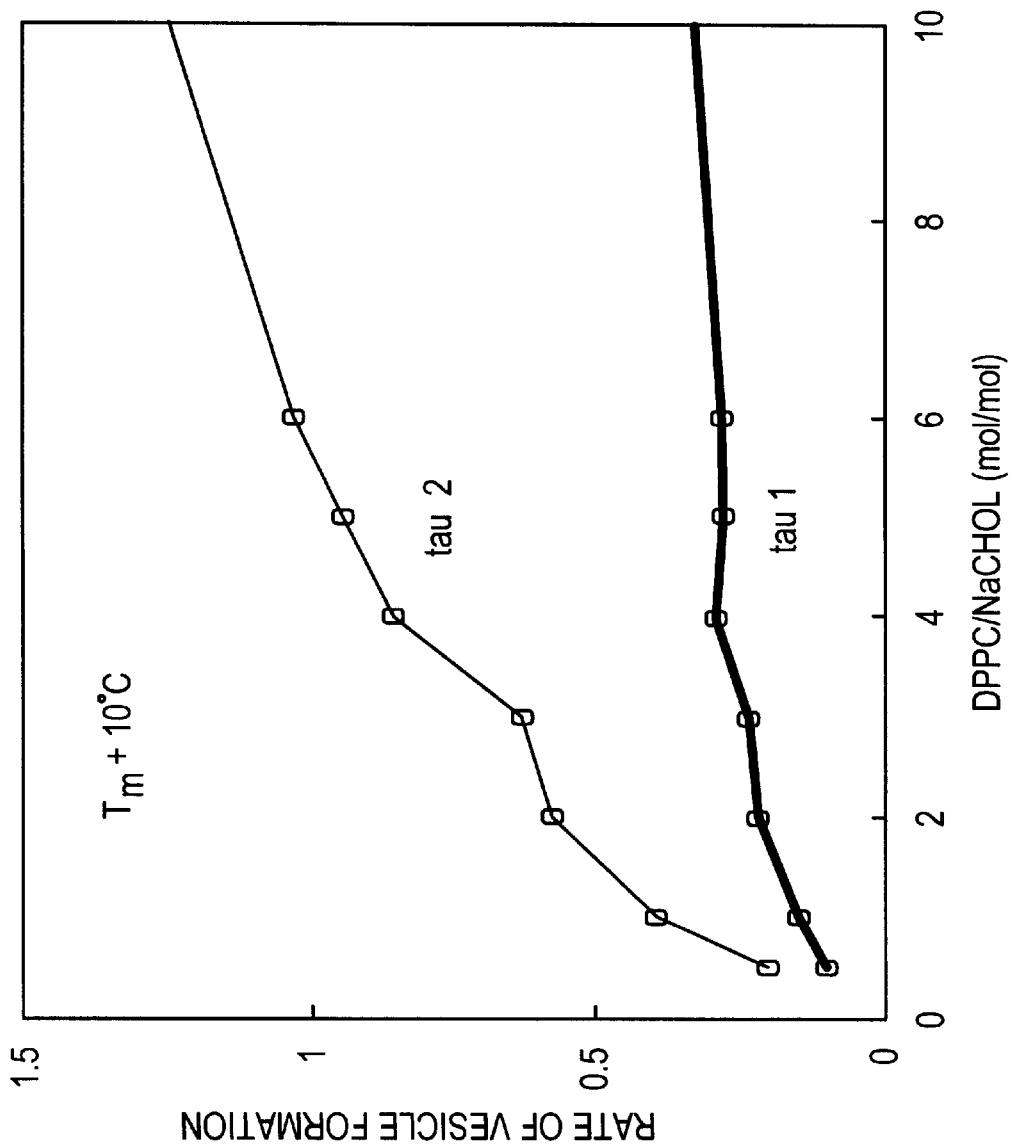
FIG. 7 is a graphical representation of the data pertaining to the rate of vesicle formation, described in Examples 99–107.

The tau 1 and tau 2 values represented in FIG. 7 show that the mechanical properties of transfersomes, which are reflected in the value of parameter tau 2, exhibit a similar L/S dependence as the solubilization and permeation tendency (cf. FIG. 6). For a 0.2% suspension investigated in this series 1 cholate molecule per lipid is required for a rapid formation of vesicles (for the formation of largely unilamellar vesicles).

Examples 108–119

Composition:

| 121.2–418.3 mg | phosphatidylcholine from soy-bean (Grade I, PC) |
| 378.8–81.7 mg | Triton X–100 |
| 4.5 ml | 0.9% NaCl solution in water |

Preparation:

A 10% PC-suspension in isotonic solution of sodium chloride is homogenized at 22° C. until the mean size of lipid vesicles is approx. 400 nm. This suspension is then distributed in aliquots of approx. 4.8 ml. A sufficient volume of Triton X-100 is pipetted into each of these aliquots to give a concentration series with nominal PC/Triton ratios in the range of 0.25 through 4 in steps of 0.5. All resulting samples are occasionally mixed and incubated at 4° C. for 14 days.

Vesicle solubilization

Figure 8:
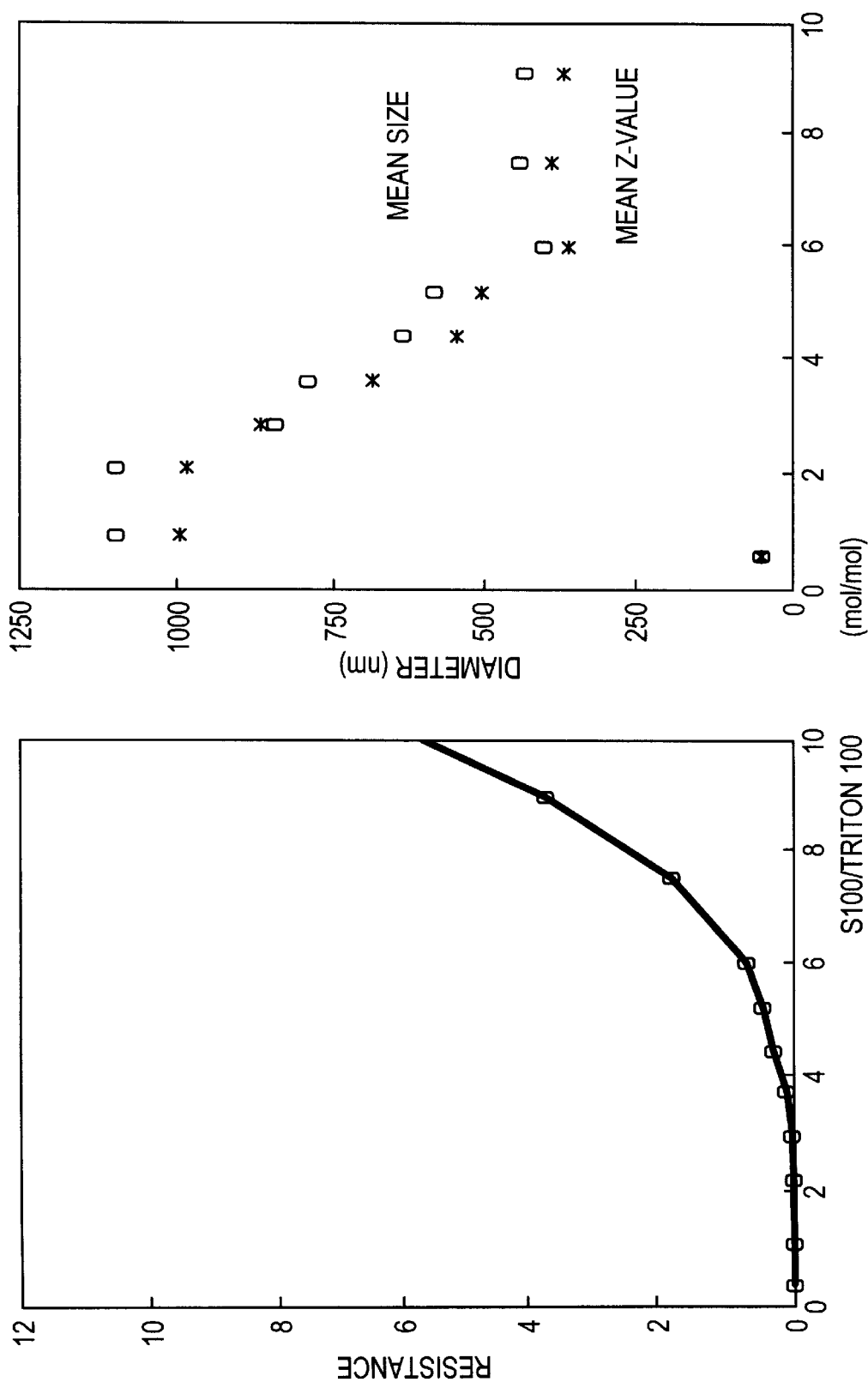
FIG. 8 is a graphical representation of the vesicle solubilization data and the permeation resistance data described in Examples 108–119.

The optical density (OD (400 nm)) of a lipid-triton mixture after a 10-fold dilution provides insight into the vesicle solubilization; this is represented in the right panel of FIG. 8. The solubilization limit is approx. 2 triton molecules per PC-molecule. Right below this limit, the optical density (OD (400 nm))—and thus the vesicle diameters—attain the greatest values. At PC/triton ratios higher than 2,5/1, the change in the optical density of given suspensions is only minimal.

Vesicle permeation and characteristics:

In order to evaluate the permeation capability of the resulting lipid vesicles and transfersomes all suspensions were pressed through fine-pore filters (0.22 micrometer), as described in examples 1–13. The required pressure increases gradually with the decreasing total triton concentration in the suspension; for L/S ratios higher than 2/1 this significantly limits the permeation capability of carriers.

Corresponding results are summarized in the left half of FIG. 8.

Examples 120–128

Composition:

| 403.5–463.1 mg | dipalmitoyl tartaric acid ester, Na-salt |
| 96.5–36.9 mg | laurylsulfate, Na-salt (SDS) |
| 4.5 ml | triethanolamine buffer, pH 7.5 |

Preparation:

In this test series a synthetic lipid, which is not found in biological systems, was chosen to be the basic transfersome constituent. For each experiment the required dry lipid mass was weighed into a glass vial and mixed with 4.5 ml of buffer.

The latter contained sufficient amounts of sodiumdodecylsulfate (SDS) to give various L/S ratios between 2/1 and 6/1. Well mixed suspensions were first kept at room temperature for 24 hours and subsequently mixed again thoroughly.

Permeation capacity and vesicle characteristics:

Liposomes were pressed through a 0.2 micrometer filter. Simultaneously, the permeation resistance was measured. Vesicles with an L/S ratio below 4/1 can pass the membrane pores very easily; in contrast to this, all vesicles with lower surfactant concentrations or vesicles without edge active components can pass through the porous constrictions only with difficulty (not before an excess pressure of 5 MPa has been created) or not at all (membranes burst).

Examples 129–136

Composition:

| 101.6–227 mg | phosphatidylcholine from soy-bean |
| 148.4–22.2 mg | octyl-glucopyranoside (β-octylglucoside), |
| puriss. 9.85 ml | phosphate buffer, pH 7.3 |
| | ethanol, absolute |

Preparation:

Phosphatidylcholine in ethanol (50%) and octylglucopyranoside were mixed in different relative ratios in order to prepare a concentration series with increasing L/S values between 1/4 and 2/1 (and a final total lipid concentration of 2.5%). Each lipid mixture in a glass vial was then supplemented with 4.5 ml of buffer. Subsequently, the resulting suspension was mixed in an agitator for 48 hours at 25° C. The suspension turbidity was greater for the specimen containing lower amounts of octylglucoside. A fine sediment formed in standing samples. Each suspension was mixed thoroughly before the experiment.

Vesicle permeation and characteristics:

All suspensions can be filtered without any problem through filters with a pore diameter of 0.22 micrometer, using only minimal excess pressures of less than 0.1–0.2 MPa; the only two exceptions are the samples with the lowest surfactant concentration. These give rise to small permeation resistances which on the renormalized scale (cf.

Figure 9:
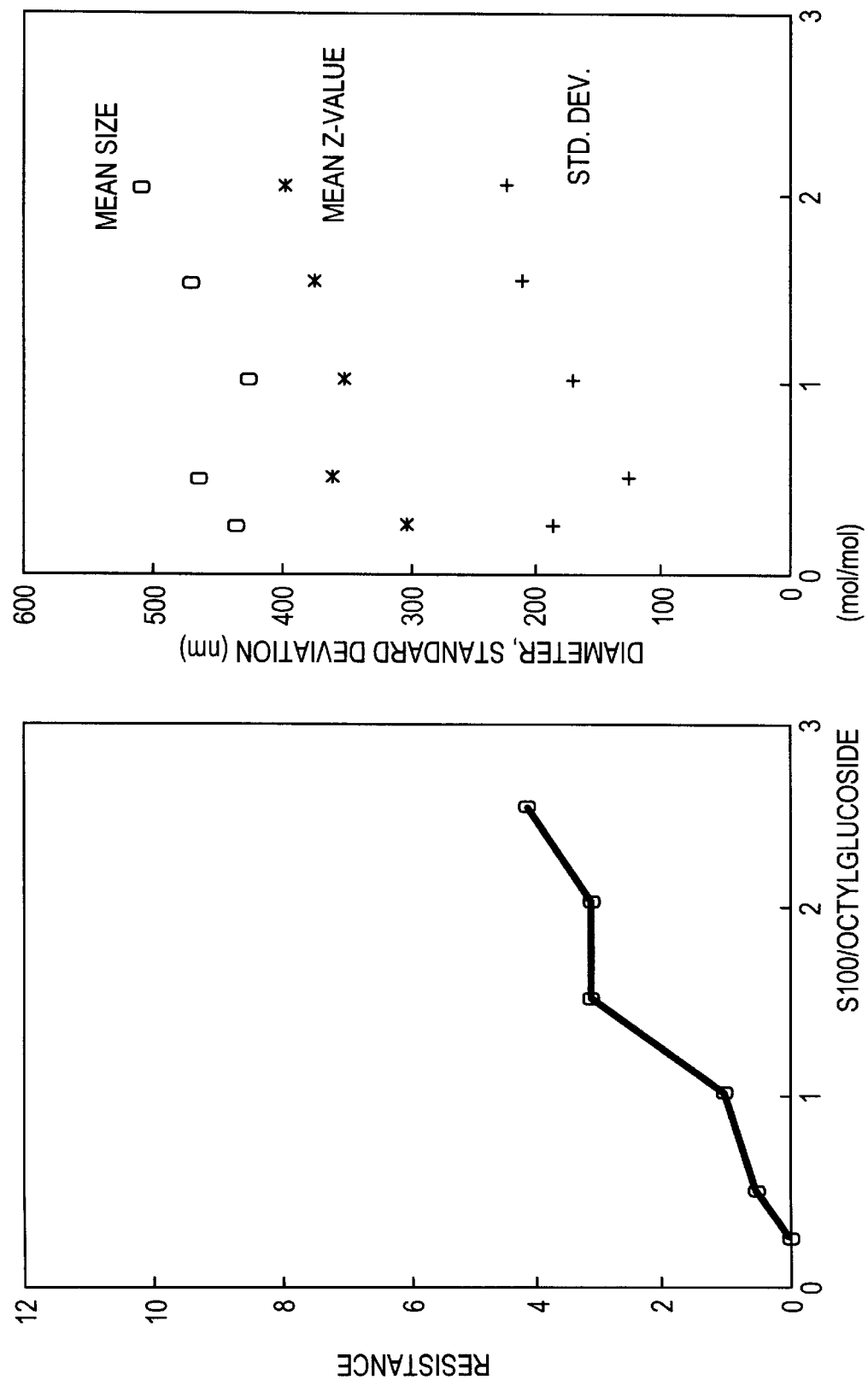
FIG. 9 is a graphical representation of the permeation resistance and the vesicle size data described in Examples 129–136.
Figure 10:
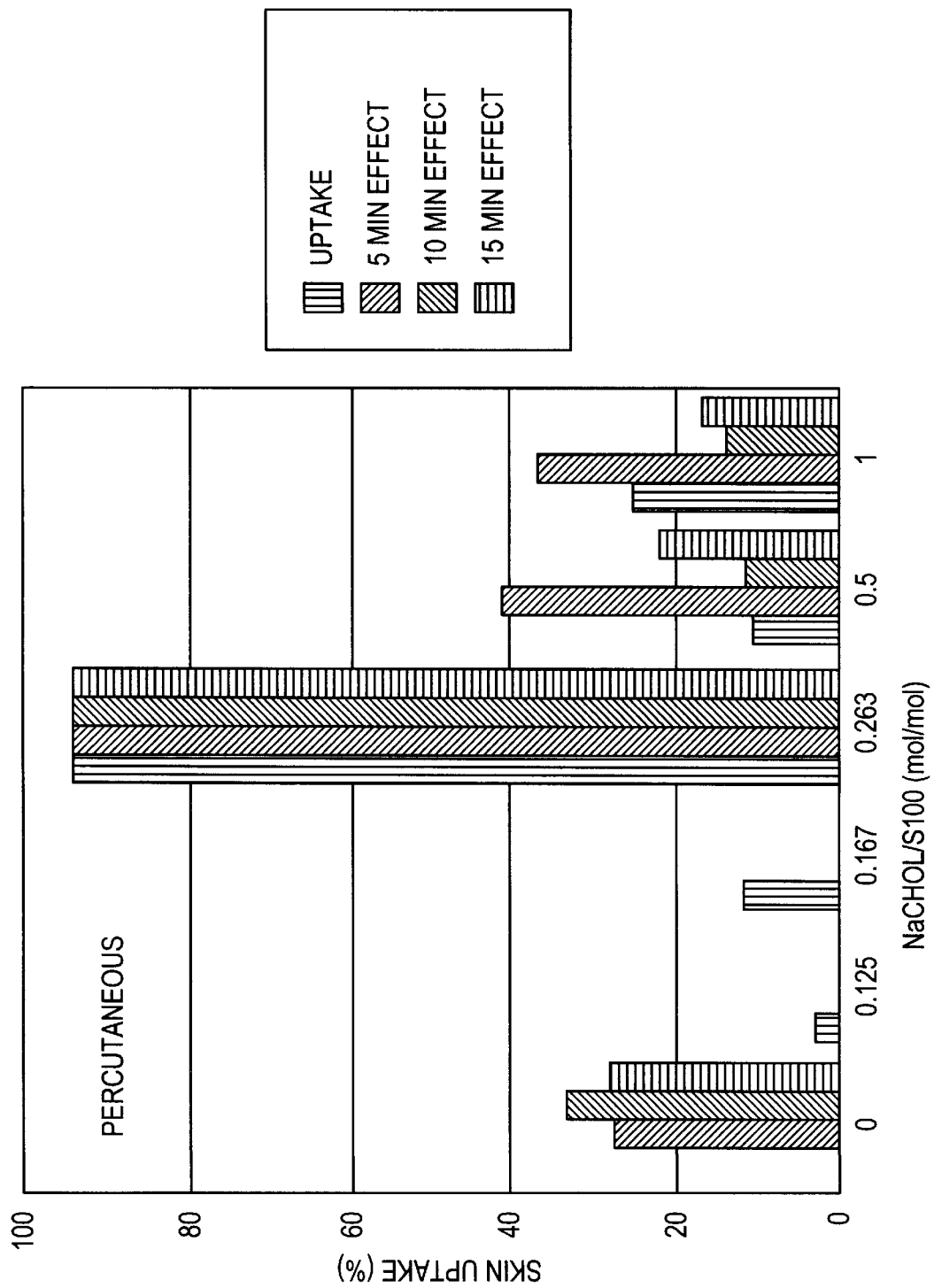
FIG. 10 is a graphical representation of the skin-uptake data described in Examples 151–157.
Figure 11:
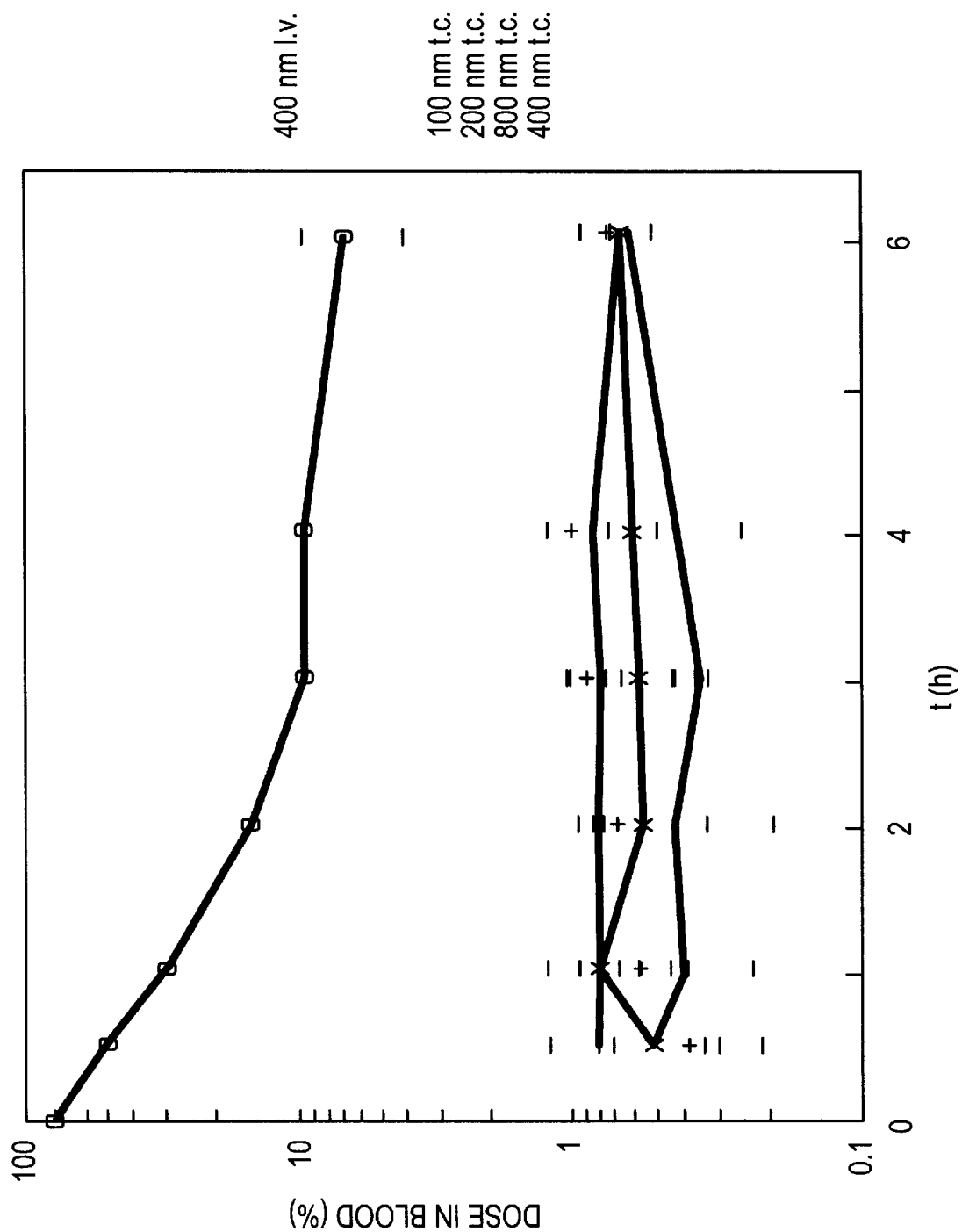
FIG. 11 is a graphical representation of the experimental data described in Examples 158–162.

FIGS. 1–5) corresponds to values of approx. 1 and 2.5, respectively. FIG. 9 presents said data.

If the pore diameter is reduced to 0.05 micrometers only suspensions with L/S ratios below 2/1 can still be filtered.

Irrespective of the pore size used all preparations with L/S ratios below 2/1 are unstable; after only a few days, a phase separation is observed between a micelle rich and a vesicle rich phase.

Examples 137–138

Composition:

| | |
|---|---|
| 43.3 mg, 50 mg | phosphatidylcholine from soy–bean |
| 0.5 mg | phosphatidylethanolamine-N-fluorescein |
| 6.7 mg, 0 mg | cholate, Na-salt, p.a. |
| 5 ml | Hepes–buffer, pH 7.3 |

Preparation:

Phosphatidylcholine with the addition of 1%-fluoresceinated lipids with or without desoxycholate is suspended in 5 ml buffer. The lipid/surfactant ratio is 3.5/1 or 1/0. Both 1%-suspensions are then ultrasonicated in a glass vial for 1.5 or 15 minutes (25 W, 20° C.), until the mean vesicle size is approx. 100 nm.

Spontaneous vesicle permeation:

Onto a Millipore-filter with 0.3 micrometer pore diameter, mounted into a Swinney-holder, the lower half of which has been wetted and filled with water, 50 microliters of a lipid suspension are pipetted through the upper opening. By a gentle swinging motion, a relatively homogeneous sample distribution on the filter surface is ensured. After 30 minutes, the holder is carefully opened and left to dry for 60 minutes. Subsequently the water from below the filter is collected and checked fluorimetrically (excitation 490 nm, emission 590 nm). (The determined light intensity is a measure of the permeation capacity.)

The transport of fluorescence markers mediated by surfactants containing transfersomes gives rise to a fluorescence signal of 89.5; in control experiment a value of 44.1 is established. This indicates that transfersomes are capable of transporting encapsulated substances across permeability barriers.

Examples 137–139

Composition:

| | |
|---|---|
| 43.5, 45.3, 50 mg | phosphatidylcholine from soy-bean |
| 0.5 mg | phosphatidylethanolamine-N-fluorescein |
| 6.5, 4.7, 0 mg | desoxycholate, Na-salt, p.a. |
| 25 ml | Hepes-buffer, pH 7,3 |

Preparation and results:

Lipid vesicles are made and tested as described in examples 137–138. Measurements show that the transfersomes which contain deoxycholate already show similarly good results at a characteristic L/S ratio of 5/1 as transfersomes which contain cholate at a ratio of L/S=3.5.

Examples 140–142

Composition:

| | |
|---|---|
| 50 mg; 43.3 mg, 15.9 mg 0.5mg | phosphatidylcholine from soy-bean phosphatidylethanolamine-N-fluorescein |
| 0 mg; 6.7 mg; 34.1 mg | cholate, Na-salt, p.a. |
| 5 ml | Hepes-buffer, pH 7.3 |

Preparation:

Lipid vesicles consisting of phosphatidylcholine and a fluorescent additive were made as in examples 137–138. For this experiment, suspensions with a lipid/surfactant ratio of 1/0, 4/1 and 1/4 were used. The former two contained fluorescent lipid vesicles, the latter a micellar suspension.

Spontaneous penetration into Plant leaves:

A fresh onion is carefully opened in order to gain access to individual leaves; these correspond to low-chlorophyll plant leaves. For each measurement, 25 microliters of a fluorescinated suspension are applied onto the concave (inner or upper) side of each onion leaf; as a result of this a convex droplet with an area of approx. 0.25 square centimeters is formed. (Carriers which contain surfactants can be easily identified owing to their higher wetting capability.) After 90 minutes the (macroscopically) dry lipid film is eliminated with the aid of a water stream from a jet-bottle with a volume of 50 ml.

After this treatment, the 'leaf surface' attains a slightly reddish appearance in the case of surfactant containing transfersomes as well as mixed micelles. Leaves incubated with surfactant-free vesicles cannot be distinguished from the untreated leaves.

Fluorescence measurements using a red filter (excitation through a blue filter from above) show that leaves which were covered with transfersomes are intensively fluorescent throughout the treated area. In certain places extremely brilliant aggregates are detected; these probably correspond to the non-eliminated vesicle-clusters. The fluorescence of leaves which were treated with a surfactant solution in some places is comparably intensive; at other positions their fluorescence is weaker, however, than in the case of transfersome-treated leaves.

The leaves which were treated with standard lipid vesicles do not fluoresce. Over large surface areas they are indistinguishable from the non-treated leaf regions.

This shows that transfersomes can transfer lipophilic substances spontaneously and irreversibly into a plant leaf or its surface. Their penetration capacity exceeds that of preparations containing highly concentrated surfactants, i.e. well established 'membrane fluidizers'.

Examples 143–145

Composition:

| | |
|---|---|
| 50 mg; 43.5 mg; 17.1 mg | phosphatidylcholine from soy-bean |
| 0.5 mg | phosphatidylethanolamine-N-fluorescein |
| 0 mg; 4.7 mg; 32.9 mg | desoxycholate, Na-salt, p.a. |
| 5 ml | Hepes-buffer, pH 7.3 |

Preparation and results:

The preparation and results are identical with those of experiments 140–142.

Examples 146–148

Composition:

| | |
|---|---|
| 50 mg; 36.4; 20 mg | phosphatidylcholine from soy-bean |
| 0.5 mg | phosphatidylethanolamine-N-fluorescein |
| 0 mg; 13.6 mg; 30 mg | Brij 35 |
| 5 ml | Water |

Preparation and results:

Preparation and results are comparable to those of experiments 140–142 and 143–145.

Examples 146–150

Composition:

| | |
|---|---|
| 84.2 to 25 mg | phosphatidylcholine from soy-bean 80% |
| 75 kBq | Giberellin A4, 3H-labelled |
| 15.8 to 75 mg | polyoxyethylene (23)-laurylether (Brij 35) |
| 1 ml | water |
| | ethanol, absolute |

Preparation:

An ethanolic lipid solution (50%) is mixed with a corresponding amount of an ethanolic solution of giberellin and suspended in 1 ml of water or in appropriate volumes of a surfactant suspension to obtain a total lipid concentration of 10% and L/S ratios of 8/1, 4/1, 2/1, 1/1 and 1/2. The resulting (mixed) suspension is then briefly homogenized with the aid of ultrasound so that the mean vesicle size is always below 300 nm.

Carrier suspensions are distributed over the surface of 3 leaves of Ficus Benjaminii; there, they are permitted to dry for 6 hours. After subsequent intensive washing of each leaf surface with 5 ml of water per square centimeter and destaining with a peroxide solution, the radioactivity in the homogenized plant material is measured scintigraphically in a beta-counter.

Agent transport in plant leaves:

Experiments show, as in examples 140–142, that transfersomes can bring the agent molecules into a leaf surface much more effectively than a micellar solution.

Examples 151–157

Composition:

| | |
|---|---|
| 32.8–0.64 mg | phosphatidylcholine from soy-bean (purity higher than 95%, PC) |
| 75 kBq | dipalmitoylphosphatidylcholine tritium-labelled |
| 2.2–34.4 mg | bile acid, Na-salt, p.a. |
| 0.32 ml | phosphate buffer, pH 7.3 |

Preparation:

In each case, 35 mg of lipid are mixed with tritium-labelled dipalmitoylphosphatidylcholine in chloroform. After thorough drying under vacuum, the resulting mixture is suspended in 0.32 ml of buffer; the nominal surfactant/lipid ratios are 0; 0.125; 0.167; 0.263; 0.5 and 1 mol/mol. All suspensions are ultrasonicated until they are comparably opalescent, with the exception of the last, optically clear micellar solution. (The time for efficient necessary sonication decreases with increasing S/L). Control measurements with non-radioactive suspensions indicate that the mean 'particle' size in all samples must be around 100 nm. In all experiments approximately 1 day old suspensions are used.

Penetration into and through the intact skin:

On the back of an immobilized nude-mouse anaesthesized with ether six areas of 1×1 cm are marked. Each of these areas is covered with 20 microliters of a carrier suspension at 3×5 minutes intervals. 60 minutes later, the mouse is killed. From each treated area a sample is excised which is then cut to pieces, solubilized and de-stained. The skin-associated radioactivity is measured scintigraphically.

The corresponding results are summarized in FIG. 10. For comparison, the normalized values are also given which were taken from our patent application pertaining to the use of liposomes for topical anaesthesia. Optimal transfersomes are appreciably better than non-optimal preparations containing surfactants.

Examples 158–162

Composition:

| | |
|---|---|
| 31 mg | phosphatidylcholine from soy-bean (purity higher than 95%, PC) |
| 75 kBq | dipalmitoylphosphatidylcholine tritium-labelled |
| 4 mg | deoxycholate, Na-salt, p.a. |
| 0.32 ml | phosphate buffer, pH 7.3 |

Preparation:

In each case 35 mg of lipid (PC and deoxycholate) are mixed with tritium-labelled dipalmitoylphosphatidylcholine in a chloroform solution. The resulting lipid mixture is dried and then dissolved in 30 microliters of warm, absolute ethanol. This solution is then mixed with 0.32 ml of a buffer solution (phosphate buffer, 10 mM, 0.9% NaCl); this corresponds to a lipid/surfactant ratio of 4/1. The resulting suspension is thoroughly mixed and subsequently filtered through filters with pore sizes of 0.8; 0.45; 0.22 and 0.1 micrometers; this gives rise to vesicles with diameters of approx. 800, 400, 200 or 100 nm (suspensions A, B, C, D).

Penetration into and through the skin:

Tails of 2 anaesthesized mice are treated with 50 microliters of a corresponding vesicle suspension for 15 minutes. Two control animals obtain an i.v. injection of 0.2 ml 1/10 diluted suspension B. After 30, 60, 120, 180, 240 and 360 minutes, blood specimens are drawn from the tail-tip. The radioactivity of these samples, which is determined by means of beta-scintigraphy, is a reliable indication of the systemic concentration of carrier-associated, radioactively labelled lipids.

Experimental data show (FIG. 11) that systemically applied transfersomes are eliminated from blood comparably as rapidly as standard liposomes. The size of carrier particles appears not to affect the spontaneous penetration into skin. All transfersomes investigated in this study can penetrate intact skin and get into the depth of a body quite effectively within a period of 4 hours at approx. 1 carrier; tendency increasing.

Examples 163–165

Composition:

| | |
|---|---|
| 88 mg | phosphatidylcholine from soy-bean (purity higher than 95%, PC) |
| 75 kBq | insulin, tritium labelled |
| 12 mg | deoxycholate, Na-salt, p.a. |
| 100 ml | ethanol, absolute |
| 0.9 ml | isotonic salt solution |

Preparation:

100 mg of PC dissolved in 100 ml of warm ethanol, or a corresponding PC/deoxycholate solution (L/S=4.5), are mixed with 0.9 ml of an isotonic salt solution (suspensions A and B, respectively). Each suspension is ultrasonicated until the mean vesicle size is about 150 nm.

12 microliters of an aqueous solution of tritium-labelled inulin are pipetted into 38 microliters of a freshly prepared suspension of empty liposomes (A) or transfersomes (B). Subsequently, all mixtures are sonicated in closed vials for 60 minutes in an ultrasound bath at room temperature; they are all used for experiments within 24 after vesicle preparation.

Spontaneous inulin transfer through the skin:

On the abdomen of NMRI-mice in general anaesthesia, which three days before were depillated using medical tweezers, 10 microliters of a vesicle suspension containing inulin in every case are applied twice at time intervals of approx. 3–5 minutes.

15, 30, 60, 120, 180, 240, 300 and 360 minutes later, 0.05 ml of blood are routinely taken from the tail of a each mouse to be then investigated scintigraphically. 6 hours later the subcutaneous tissues at the application site, as well as liver and spleen of all animals of this experiment are collected. After solubilization and decolouring procedures, these organs are also checked scintigraphically.

Figure 12:
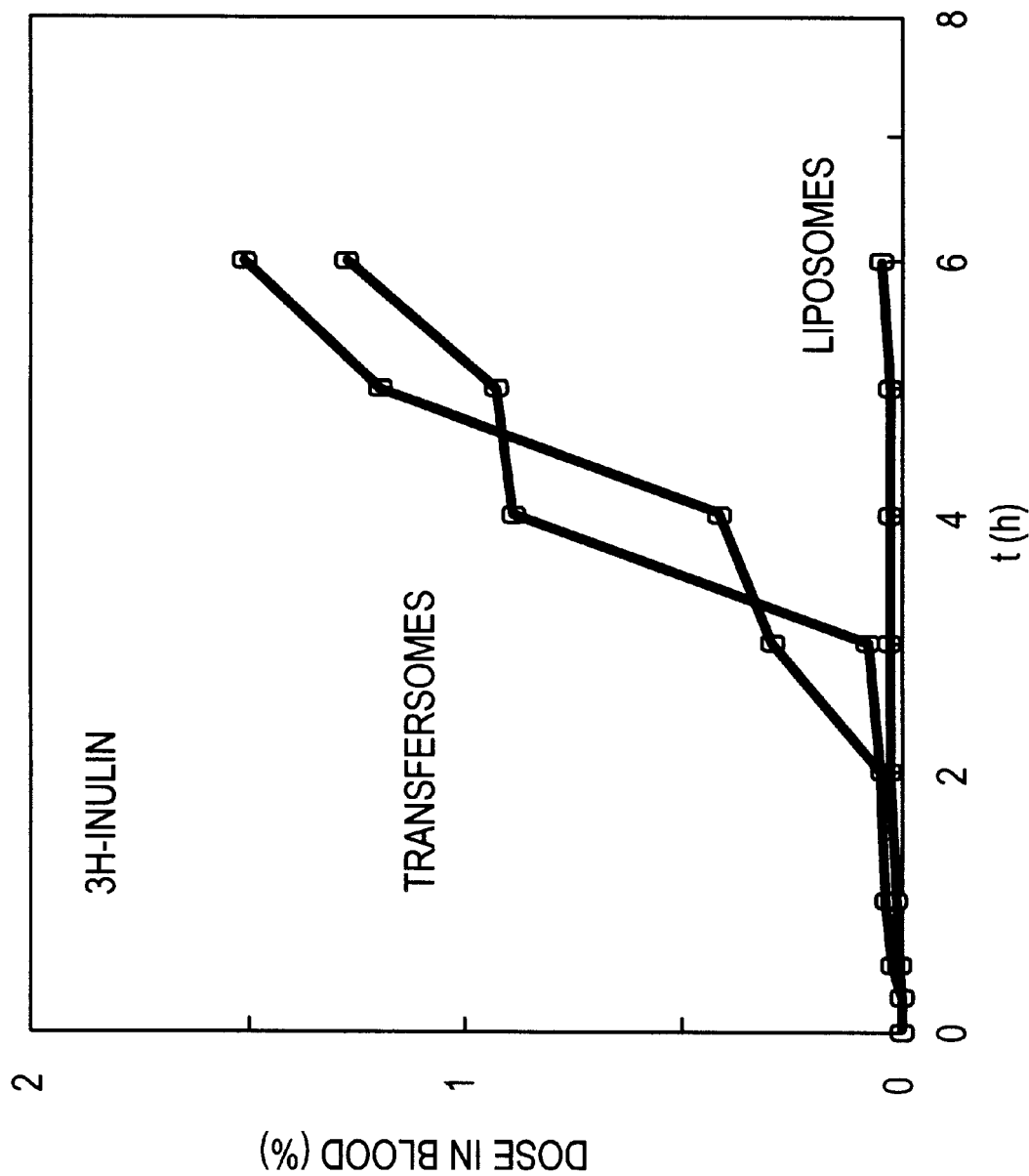
FIG. 12 is a graphical representation of the experimental data described in Examples 163–165, showing the insulin dose in blood over time.

The results of this study are collected in FIG. 12. They show that normal liposomes can hardly mediate a percutaneous inulin uptake; in contrast to this, 6 hours later approx. 1.4% of this marker which was applied in the form of transfersomes are found in the blood. This transfer sets in approximately 2–3 hours after the application and is not yet completed 6 hours after each application.

After 6 hours in the case of transfersomes, an average of 0.8% (this corresponds to 24.1% of the recovered dose) are in the skin at the application site; 0.9% are found in the liver; spleen contains less than 0.1% of the absolute dose. In the body (blood, spleen, liver) approximately 73.8% of the recovered dose are thus found again.

In contrast to this, approximately 2% of the normal liposomes at the application site can be detected by eye, the corresponding doses in the liver and spleen being below 0.1%. This corresponds to a recovery of 95.3% at the application site and 6.7% of this dose in the body of the test animal.

Example 166

Composition:

| | |
|---|---|
| 386 mg | phosphatidylcholine from soy-bean (purity > 95%) |
| 58.5 mg | sodium-cholate (L/S = 3.5) |
| 500 ml | ethanol (96%) |
| 2.25 ml | 0.9% NaCl solution (per inject.) |
| 2.25 ml | Actrapid HM 40 (corresponds to 90 I.U. of recombinant human insulin) |

Preparation:

Samples are prepared essentially as described in examples 62–75. A mixture of aqueous salt solution and human recombinant insulin (with 6.75 mg m-cresole) is mixed with a lipid solution in ethanol. The resulting, opaque suspension is aged over night. 12 hours later, this suspension is pressed through a sterile filter (Anodisc, pore diameter 0.2 micrometers) with the aid of nitrogen gas with excess pressure of 0.25 MPa under sterile conditions to be then filled into the glass container.

The nominal lipid/surfactant ratio is 3.5; the calculated molar surfactant concentration in the lipid double layer is approx. 5/1. This corresponds to 50% of the concentration required for solubilization.

The mean radius of vesicles in final suspension in this experiment was 97 nm.

Application:

0.5 ml of a fresh, insulin containing transfersome suspension are applied onto the untreated skin of the left forearm of an informed, healthy male volunteer aged 37 years (starved for 18 hours) and distributed over an area of approx. 10 cm$^2$. 5 minutes later, additional 300 microliters of identical suspension are positioned in two halves on the forearm and upper arm, respectively. 5–10 minutes later, the suspension on the upper arm (dose approx. 2,5 mg/cm$^2$) has almost completely disappeared; it has thus nearly completely penetrated into skin. In contrast to this, lipids applied onto the forearm (dose approx. 7.5 mg/cm$^2$) are still well perceptible.

Figure 13:
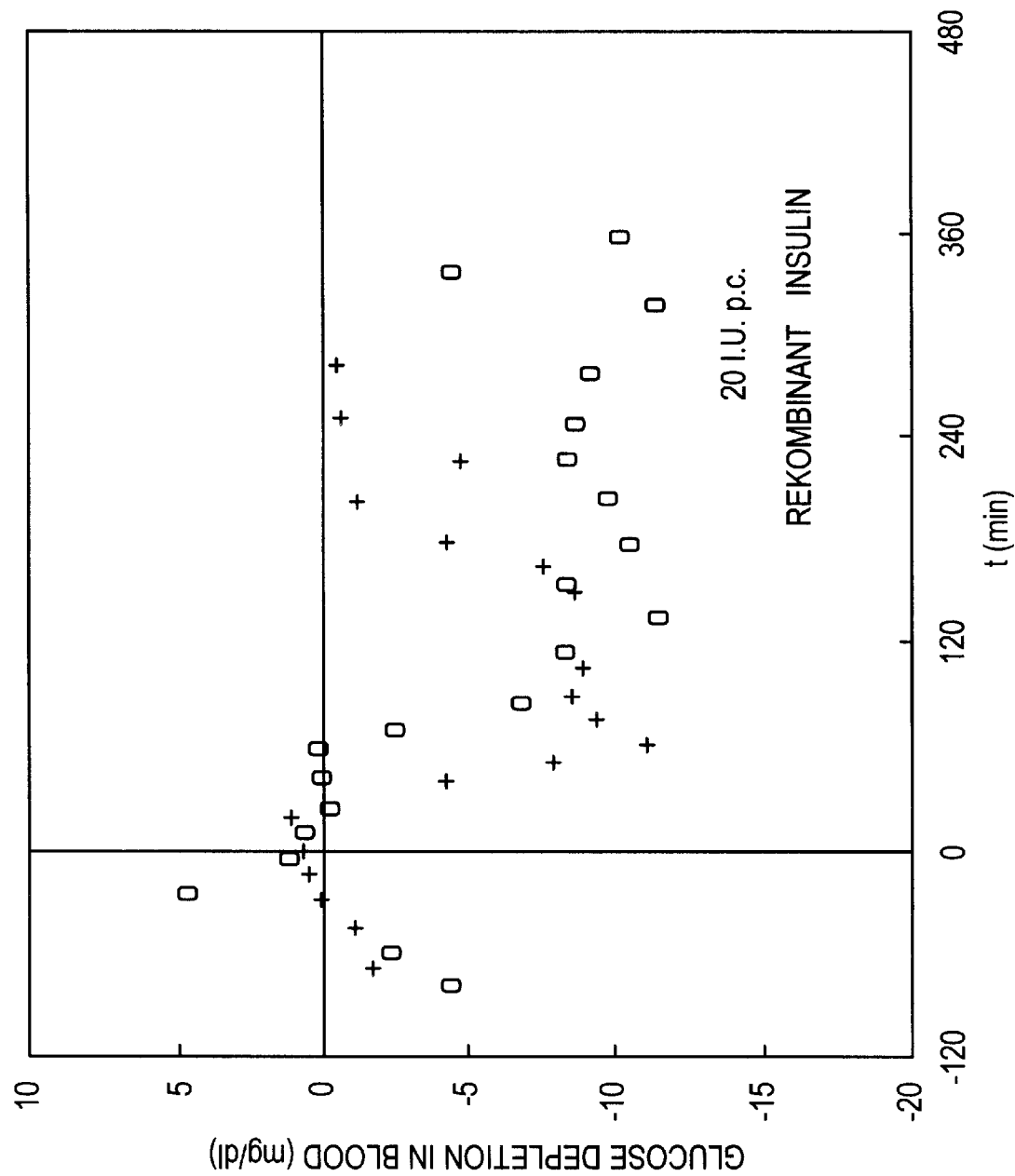
FIG. 13 is a graphical representation of the experimental data described in Example 166.

Activity:

In order to assess the biological activity of insulin, approx. 2 hours before the sample application, a permanent, soft catheter is placed into a vein in the right hand. Every 15–45 minutes, 1–1.5 ml of blood are collected from this catheter; the first 0.5–1 ml thereof are discarded; the remaining 0.5 ml are measured with a standard enzymatic glucose test. In each case three determinations with three to four independent specimens are made. The corresponding experimental data is summarized in FIG. 13. It shows that transfersomes mediate a significant hypoglycemia in the peripheral blood some 90 minutes after the drug application; this effect lasts for approx. 2 hours and amounts to approx. 50% of the magnitude of the hypoglycemic effect of a comparable dose of subcutaneously applied insulin; the effect of the former lasts 200% longer, however.

Examples 167–172

Composition:

| | |
|---|---|
| 956 mg | phosphatidylcholine from soy-bean (+95%) |
| 0–26 mg | sodium-deoxycholate |

-continued

| | |
|---|---|
| 1 mg | prostaglandine E1 |
| 1 ml | ethanol absolute |
| 50 ml | 0.9% NaCl solution (per inject.) |

Preparation:

1 ml of ethanol is pipetted into a glass flask with 1 mg of prostaglandine. After thorough mixing, the resulting prostaglandine solution is transferred to the appropriate amount of dry lipid in another glass vial. The original flask is flushed once again with the new lipid/prostaglandine solution and subsequently supplemented with 6 ml of an isotonic salt solution. The prostaglandine containing flask is washed twice with 2 ml of 0.9% NaCl and mixed with the original lipid suspension. The sample is then divided into 5 parts; into individual aliquots sodium-desoxycholate is added at concentrations of 0; 1.6; 3.25; 6.5 or twice 13 mg/ml.

The resulting 10% suspensions are aged for 24 hours. Subsequently they are either ultrasonicated or filtered manually through a 0.2 micrometer-filter, depending on cholate concentration. The specimens with the highest surfactant concentration are either filtered or ultrasonicated. Finally, the samples are diluted to obtain a final PGE1 concentration of 20 micrograms/ml and kept in dark glass bottles in a refrigerator. Vesicle radius right after sample preparation is 85 nm, two months later 100 nm.

Application and Action:

In each experiment 0.25 ml of a lipid suspension are applied on neighbouring but not interconnected regions of abdominal skin. 10 minutes later the skin surface is macroscopically dry; 15 minutes later, some of the application sites show a reddish appearance which, according to the test person's statement, is associated with a weak local pain. The intensity of oedema grades as 0, 0, 0, 0–1, 3 and 3 points (on a scale from 1–10).

This shows that merely transfersomes—but not liposomes or sub-optimal surfactant-containing vesicles—can penetrate into intact skin and thereby transfer drugs into body. The precise mode of sample preparation plays no role in this.

Examples 173–175

Composition:

| | |
|---|---|
| 79.4 mg; 88.5 mg | phosphatidylcholine from soy-bean (+95%) |
| 20.6 mg, 11.5 mg | sodium-deoxycholate |
| 10 µg | hydrocortison |
| 0.1 ml | ethanol absolute |
| 1 ml | phosphate buffer, physiological |

Preparation:

Lipids and hydrocortison are mixed as approx. 50% ethanolic solution and subsequently supplemented with 0.95 ml of phosphate buffer. The resulting, very heterogeneous suspension is treated with ultrasound (25 W, 3–5 min). Specimens with an L/S ratio of 2/1 can be homogenized with ease, specimens with L/S=4/1 are relatively difficult to homogenize.

Specimens with 1 and 2.5 weight-% result in stable suspensions independent of the precise L/S ratio; 10 weight-% of agent cannot be incorporated into stable transfersomes of the given composition.

Examples 175–200

Composition:

| | |
|---|---|
| 1.1–2 mg | phosphatidylcholine from soy-bean (+95% = PC) |
| 0–32.5 mol-% | Tween 80 |
| pH 7.2 | isotonic phosphate buffer |

Preparation:

Different amounts of phospholipid and surfactant in each experiment are weighed or pipetted into 25 ml of buffer at ratios which yield suspensions with 0–32,5 mol-% of Tween 80 and a constant total lipid concentration of 2%. Specimens are sterilized by filtering, filled into sterile glass vials and aged for 4 through 34 days. Then, the optical density of each sample is determined. This depends strongly on surfactant concentration but hardly on time within the framework of measuring conditions.

Characterization:

23 specimens each containing 3 ml of an individual lipid suspension are ultrasonicated in closed vials in a bath sonicator. Three, four and six hours later the samples' optical density is determined. Such measurements are repeated with every new sample series after the relative sample positions were exchanged in a systematic manner; the determination of optical density, again, is performed three, four and six hours after the start of sonication. All values corresponding to one concentration are summed up and divided by the number of measurements; the resulting value is a measure of the samples' capacity for vesicularization under given conditions.

Figure 16:
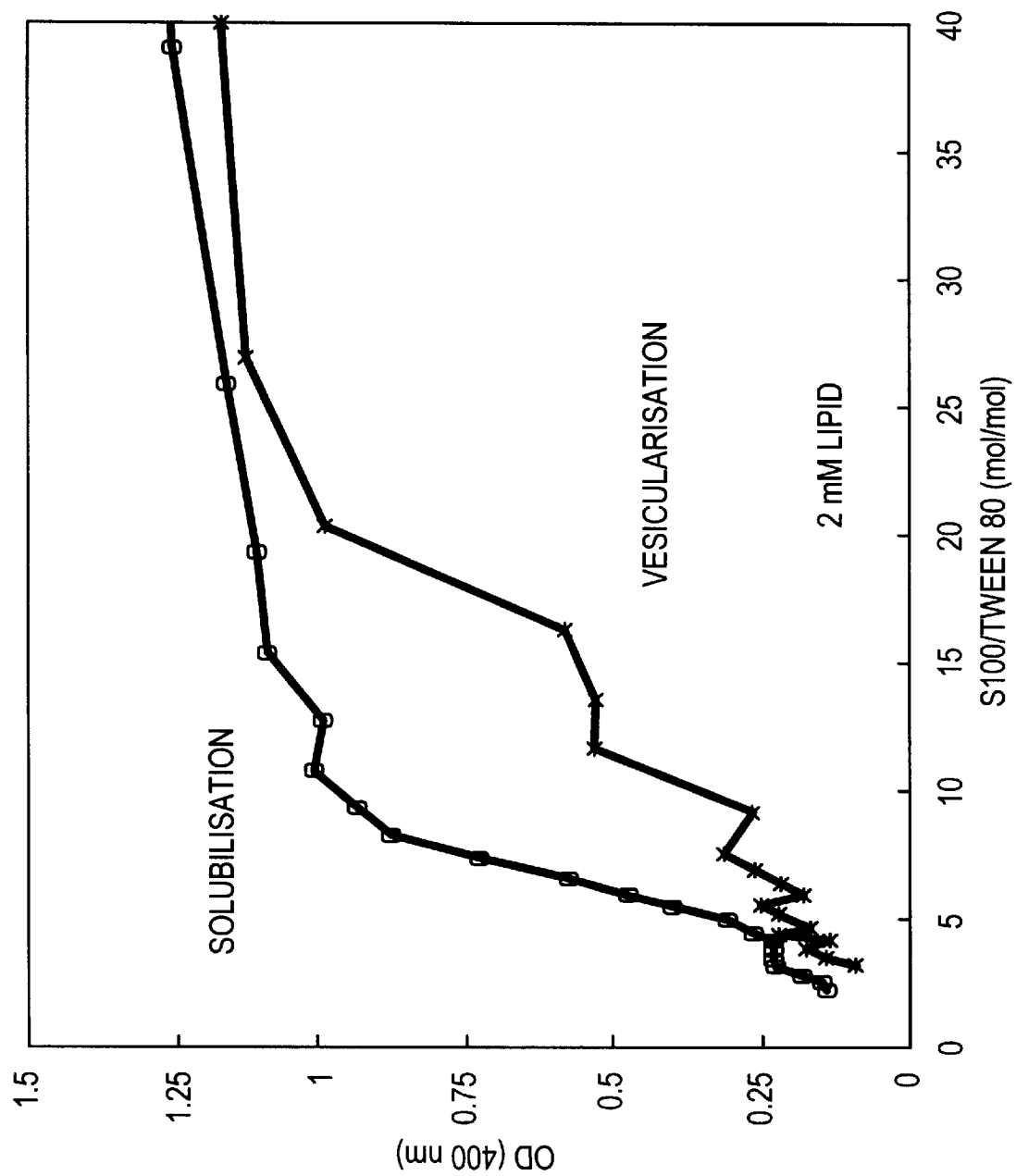
FIG. 16 is a graphical representation of the optical density data described in Examples 175–200.

This procedure is an alternative or a supplement to the permeation resistance measurements as described in examples 40–49. FIG. 16 shows, for example, that the amount of surfactant required for good mechanical deformability in the case of Tween 80 is 2–3 times lower than the corresponding solubilization concentration. This result is in good accord with the results of the permeation experiments.

Examples 201–215

Composition:

| | |
|---|---|
| 256.4–447 mg | phosphatidylcholine from soy-bean (+95% PC) |
| 243.6–53.1 mg | Brij 96 |
| 0.26–0.45 ml | ethanol, absolute |
| 4.5 ml | phosphate buffer, pH 6.5. 10 mM |

Preparation:

Increasing volumes of Brij 96 are pipetted into the corresponding volumes of an alcoholic PC solution. Thus, a concentration series is obtained with L/S values between 1/1 and 1/8. After the addition of a buffer very heterogeneous liposomes are formed which are homogenized by means of filtering through a 0.2 µm filter.

Figure 14:
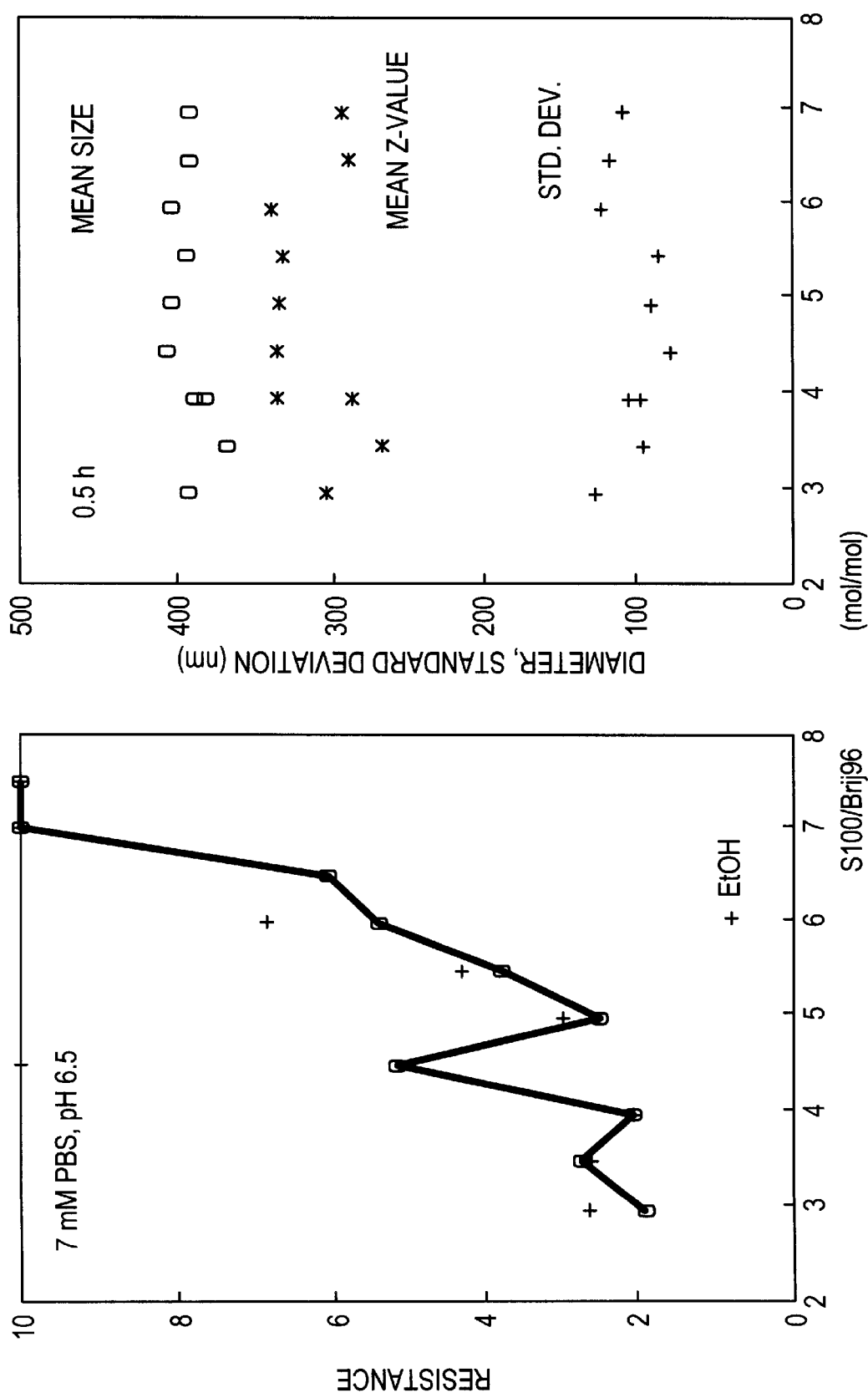
FIG. 14 and FIG. 15 are graphical representations of the permeation resistance data and the vesicle size data described in Examples 201–215 and Examples 216–235.

Permeation and carrier characteristics:

The already described method for the determination of suspensions permeability resistance is used. Corresponding values are given in the left panel of FIG. 14 as circles or crosses (two independent test series). The functional dependence of the samples' permeability resistance as a function of the L/S ratio is similar to that of comparable transfersomes and is illustrated in the right panel of FIG. 14. The maximum permeation capacity is not reached before the L/S-value is below 3.

Examples 216–235

Composition:

| | |
|---|---|
| 202.0–413 mg | phosphatidylcholine from soy-bean (+95% = PC) |
| 298.0–87.0 mg | Myrj 49 |
| 0.26–0.45 ml | ethanol, absolute |
| 4.5 ml | phosphate buffer, pH 6.5. 10 mM |

Figure 15:
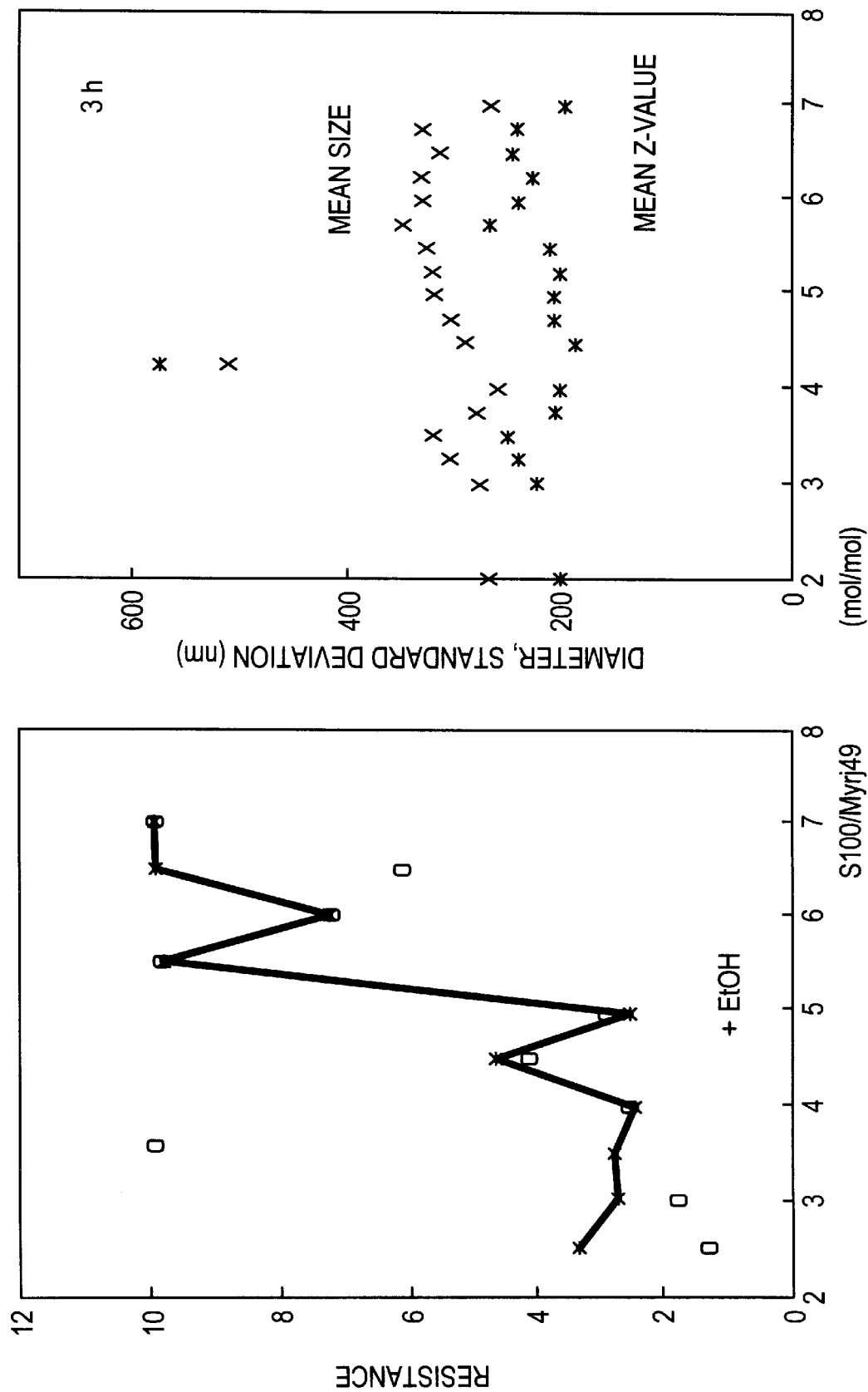

Preparation and Characterization:

Transfersomes are made and characterized as described for examples 201–215. Their permeation properties as a function of the relative surfactant concentration in the individual specimen is given in the left panel of FIG. 15. The right panel gives corresponding equilibrium values; the latter, however, provide no information about vesicle suitability for permeation and agent transport.

Example 236

Composition:

| | |
|---|---|
| 144.9 mg | phosphatidylcholine from soy-bean |
| 24.8 mg | desoxycholate, Na-salt |
| 1.45 ml | Actrapid HM 100 (145 I.U.) |
| 0.16 ml | ethanol, absolute |

Preparation:

Appropriate quantities of both lipids are dissolved in corresponding amounts of ethanol and mixed with a standard solution of insulin. 12 hours later, the crude carrier suspension is homogenized by means of filtration. Average vesicle diameter is 225±61 nm and nominal insulin concentration is 83 I.U. Over an area of appr. 10 square centimeters on the right forearm 0.36 ml (30 I.U.) of insulin in transfersomes are distributed. Blood samples are taken every 10 minutes through a heparinized soft catheter positioned in a vein in the right forearm; the first 0.5 ml are always discarded; the following 0.5–0.8 ml of each sample are sedimented and immediately frozen; the remainder of each sample is used for the determination of blood glucose concentration during the experiment.

Figure 17:
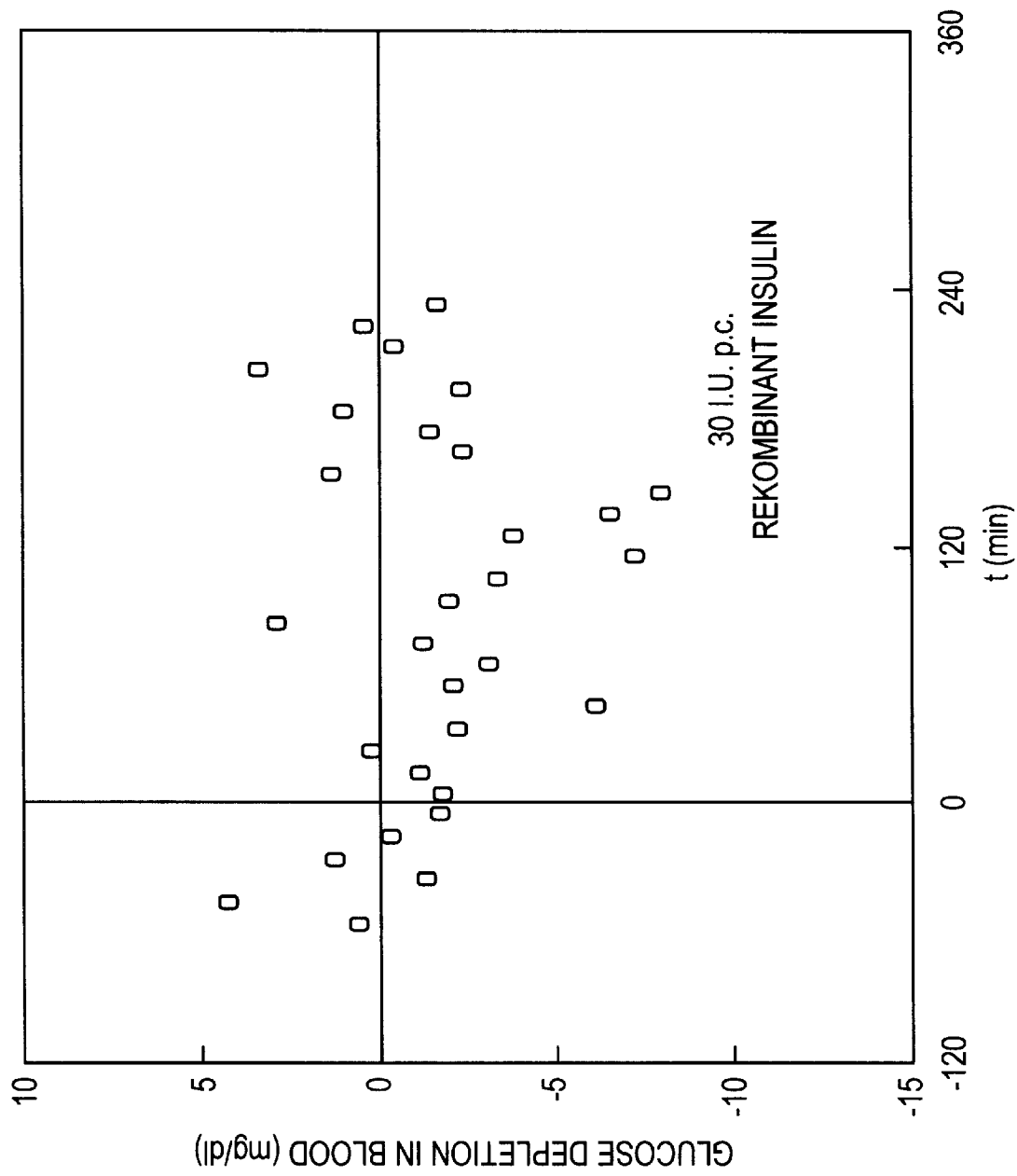
FIG. 17 is a graphical representation of the blood glucose level data described in Example 236.

Activity:

These liposomes with a relatively high surfactant concentration have only a very limited capability of transporting insulin across skin, as is seen from FIG. 17. Depending on the choice of data used for evaluation, the lowering of the blood glucose level does not exceed 2 to 5 mg/dl over a period of 30–40 minutes at the most. The effect of a comparable subcutaneous injection is 50 to 200 times higher. Surfactant-containing liposomes, which have not been optimized with regard to their 'transfersomal' properties, are consequently poorly suited for the use as carriers in the case of dermal applications. Surfactant concentration in such carriers thus cannot mediate an optimal agent permeation through skin.

This shows that formulations prepared according to this invention can (still) have a partial activity even if their content of edge active substances has not been optimized; however, a maximum advantage can only be achieved after the concentration of an edge active substance requiring maximum permeation has been determined and used as described in this patent application.

Possible use of transfersomes for the application of antidiabetics, most notably of insulin, which has been discussed above in examples 166 and 236, will be investigated in more detail in the following text.

Attempts to bring antidiabetic agents into a body without the use of an injection needle have been known for quite some time already (see, for example, the review article by Lassmann-Vague, Diabete. Metab. 14,728,1989). It has been proposed, for example, to use implantable insulin containers (Wang, P. Y, Biomaterials 10. 197, 1989) or pumps (Walter, H et al., Klin. Wochenschr. 67, 583, 1989), to administer an insulin solution transnasally (Mishima et al., J. Pharmacobio.-Dynam. 12, 31, 1989), perocularly (Chiou et al., J. Ocul. Pharmacol. 5, 81, 1989), perorally in a liposomes suspension (Rowland & Woodley, Biosc. Rep. 1, 345, 1981) or transrectally; in order to introduce insulin molecules through the skin, a corresponding solution was jet-injected (Siddiqui & Chies, Crit. Rev. Ther. Drug. Carrier. Syst. 3, 195, 1987), or brought through the skin with the aid of small injectors (Fiskes, Lancet 1, 787, 1989), electric fields (Burnette & Ongpipattanakul, J. Pharm. Sci. 76, 765, 1987; Meyer, B. R et al., Amer. J. Med. Sci. 297, 321, 1989); chemical additives should also support drug permeation.

All these procedures have hardly brought any real improvements for the therapy of diabetes patients—with the exception of jet injection, perhaps; but the latter is only a very refined, technically extremely complicated form of injection and, consequently, not very common. The daily therapy of each insulin-dependent patient, consequently, still involves injecting an insulin solution under the skin or into the muscle tissue (De Meijer, P. et al., Neth. J Med. 34, 210. 1989).

Lipids have thus far been discussed as excipients for delayed insulin release in insulin implants (Wang, P. Y Int. J Pharm. 54, 223, 1989); in the form of liposomes they were also suggested for use as vehicles for peroral applications (Patel, 1970), without the therapeutic results really being reproducible, however, (Biochem. Int. 16, 983, 1988). Subsequent publications in the field of insulin containing liposomes, therefore, have dealt with methodological rather than therapeutic issues (Wiessner, J. H. and Hwang, K. J. Biochim. Biophys. Acta 689, 490 1982; Sarrach, D. Stud. Biophys. 100. 95, 1984; Sarrach, D. and Lachmann, U. Pharmazie 40. 642, 1985; Weingarten, C. et al., Int. J. Pharm. 26, 251, 1985; Sammins, M. C. et al., J. Pharm. Sci. 75, 838, 1986; Cervato, G. et al., Chem. Phys. lipids 43, 135, 1987).

According to this invention, the transfersomes described above are used for non-invasive applications of antidiabetic agents, most frequently of insulin, in formulations which were optimized for this purpose.

It is advantageous to use at least one carrier substance for this purpose from the class of physiologically tolerable polar or non-polar lipids or some other pharmacologically acceptable amphiphiles; well-suited molecules are characterized by their ability to form stable agent carrying aggregates. The preferred aggregate form are lipid vesicles, the most preferred membrane structure is a lipid double layer.

It is, furthermore, considered advantageous if at least one such substance is a lipid or a lipoid from a biological source or some corresponding synthetic lipid; or else, a modification of such lipids, for example a glyceride-, glycerophospholipid, sphingolipid, isoprenoidlipid, steroid, sterine or sterol, a sulfur- or carbohydrate-containing lipid, or any other lipid which forms stable double layers; for example, a half-protonated fluid fatty acid. Lipids from eggs, soy-bean, coconuts, olives, safflower, sunflower, linseed, whale oil, Nachtkerze or primrose oil, etc. can be used, for example, with natural, partly or completely hydrogenated or exchanged chains. Particularly frequently, the corresponding phosphatidylcholines are used; as well as phosphatidylethanolamine, phosphatidylglycerol, phosphatidylinositol, phosphatidic acids and phosphatidylserines, sphingomyelines or sphingophospholipids, glycosphingolipids (e.g. cerebrosides, ceramidpolyhexosides, sulfateids, sphingoplasmalogenes); gangliosides or other glycolipids are also suitable for the use in transfersomes according to this invention. Amongst the synthetic lipids especially the corresponding dioleoyl-, dilinoleyl-, dilinolenyl-, dilinolenoyl-, diaracidonyl-, dimyristoyl-, less frequently dipalmitoyl-, distearoyl-, phospholipide or the corresponding sphingosin derivatives, glycolipids or other diacyl- or dialkyl-lipids are used; arbitrary combinations of the above-mentioned substances are also useful.

It is advantageous if an edge active substance is a nonionic, a zwitterionic, an anionic or a cationic surfactant. It can also contain an alcohol residue; quite suitable components are long-chain fatty acids or fatty alcohols, alkyl-trimethyl-ammonium-salts, alkylsulfate-salts, cholate-, deoxycholate-, glycodeoxycholate-, taurodeoxycholate-salts, dodecyl-dimethyl-aminoxide, decanoyl- or dodecanoyl-N-methylglucamide (MEGA 10, MEGA 12), N-dodecyl-N,N-dimethylglycine, 3-(hexadecyldimethylammonio)-propanesulfonate, N-hexadecylsulfobetaine, nonaethyleneglycol-octylphenylether, nonaethylene-dodecylether, octaethyleneglycol-isotridecylether, octaethylene-dodecylether, polyethylene glycol-20-sorbitane-monolaurate (Tween 20), polyethylene glycol-20-sorbitane-monooleate (Tween 80), polyhydroxyethylenecetylstearylether (Cetomacrogo, Cremophor O, Eumulgin, C 1000) polyhydroxyethylene-4-laurylether (Brij 30), polyhydroxyethylene-23-laurylether (Brij 35), polyhydroxyethylene-8-stearate (Myrj 45, Cremophor AP), polyhydroxyethylene-40-stearate (Myrj 52), polyhydroxyethylene-100-stearate (Myrj 59), polyethoxylated castor oil 40 (Cremophor EL), polyethoxylated hydrated castor oil, sorbitane-monolaurate (Arlacel 20, Span 20), especially preferred decanoyl- or dodecanoyl-N-methylglucamide, lauryl- or oleoylsulfate-salts, sodiumdeoxycholate, sodiumglycodeoxycholate, sodiumoleate, sodiumelaidate, sodiumlinoleate, sodiumlaurate, nonaethylene-dodecylether, polethylene-glycol-20-sorbitane-monooleate (Tween 80), polyhydroxyethylene-23-lauryl ether (Brij 35), polyhydroxyethylene-40-stearate (Myrj 52), sorbitane-monolaurate (Arlacel 20, Span 20) etc.

Amongst the most suitable surfactants in these classes of substances are: n-tetradecyl(=myristoyl)-glycero-phosphatidic acid, n-hexadecyl-(=palmityl)-glycero-phosphatidic acid, n-octadecyl(=stearyl)-glycero-phosphatidic acid, n-hexadecylene(=palmitoleil)-glycero-phosphatidic acid, n-octadecylene(=oleil)-glycero-phosphatidic acid, n-tetradecyl-glycero-phosphoglycerol, n-hexadecyl-glycerophosphoglycerol, -n-octadecyl-glycero-phosphoglycerol, n-hexadecylene-glycero-phosphoglycerol, n-octadecylene-glycerophosphoglycerol, n-tetradecyl-glycero-phosphoserine, n-hexadecyl-glycero-phosphoserine, -n-octadecyl-glycero-phosphoserine, n-hexadecylene-glycero-phosphoserine and n-octadecylene-glycero-phosphoserine.

Total concentration of the basic carrier subtance is normally between 0.1 and 30 weight-%; preferably, concentrations between 0.1 and 15%, most frequently between 5 and 10% are used.

Total concentration of the edge active substance in the system amounts to 0.1% through to 99 mol-% of the quantity which is required to solubilize the carrier, depending on each application. Frequently, the optimum is drug dependent—in a concentration range between 1 and 80 mol-%, in particular between 10 and 60 mol-%; most frequently values between 20 and 50 mol-% are favoured.

The concentration of the drug agent in the case of insulin is most frequently in the range between 1 and 500 I.U./ml; concentrations between 20 and 100 I.U./ml are preferred; carrier concentration in the latter case is in the range between 0.1-20 weight-%, frequently between 0.5 and 15 weight-%, most frequently between 2.5 and 10 weight-%.

For preparing a therapeutic formulation, the carrier substances, which are very frequently lipids, are taken as such or dissolved in a physiologically acceptable solvent or a water-miscible solubilizing agent, combined with a polar solution, and made to form carriers.

It is advantageous to use polar solutions containing edge active substances; the latter can also be used with lipids or be contained in a lipid solution.

Carrier formation is preferably initiated by stirring in, by means of evaporation from a reverse phase, by means of an injection or a dialysis procedure, through mechanical agitation, such as shaking, stirring, homogenization, ultrasonication, friction, shear, freezing-and-thawing, by means of high-and low-pressure filtration, or any other use of energy.

It may be advantageous to incorporate agents only after carrier formation.

If transfersomes are prepared by means of filtration, materials with a pore size of 0.1–0.8 micrometers, very frequently of 0.15–0.3 micrometers, and particularly preferred of 0.22 micrometers are preferably used; several filters can also be used in combination or in a row.

In the case that transfersomes are made by means of ultrasonication, energy densities in the order of 10–50 kW/liter/minute are preferably used; in stirring or rotary machines 1,000 through to 5,000 revolutions per minute are typically used. If high pressure homogenizers are used, pressures in the order of 300–900 Bar normally ensure sufficient transfersome homogeneity and quality after a single passage; in the latter case even suspensions with 20–30% lipids can be processed without any difficulty.

It is often sensible to prepare transfersomes only shortly before an application from a concentrate or lyophylisate.

Cryopreservatives, such as oligosaccharides, can facilitate the formation of transfersomes from a lyophylisate.

Standard agent, supporting, or additional substances, in particular the stabilizing, protective, gel-forming, appearance-affecting substances and markers can also be used as described in this application.

The following examples illustrate this invention without implying any limits to its general use. Temperatures are given in degree Celsius, carrier sizes in nanometers, and other quantities in common SI units.

Example 237

Composition:

| | |
|---|---|
| 120 mg | phosphatidylcholine from soy-bean (purity > 95%) |
| 20 mg | sodium-cholate p.a. (L/D = 3.2) |
| 150 µl | ethanol (96%) |
| 1.45 ml | Actrapid HM 100 (recombinant human insulin 100 I.U./ml) |

Preparation:

This preparation is produced as described in example 166, with only minor modifications. The main difference is that the lipid/insulin mixture is hand-filtered through a 0.22 µm polycarbonate filter (Sartorius) using a 1 ml injection already few minutes after mixture preparation. The final volume of the suspension is 1.2 ml; the nominal lipid/cholate ratio is 2.8/1, in lipid membranes approx. 2.4/1. The final concentration of insulin is approx. 83 I.U./ml; the vesicle radius one day after preparation is 94 nm on the average; one week later, 170 nm.

Application:

One and half hours after the beginning of the experiment, 240 µl of a sterile suspension of insulin containing transfersomes (with 20 I.U.) were taken. These were applied and uniformly smeared at a dose of approx. 0.7 mg lipid/cm$^2$ over the inner side of the right forearm of a male test person starved for 18 hours prior to experiment. 5 minutes later the skin surface is macroscopically dry. Another 45 minutes later no traces of application are visible anymore.

Activity:

At irregular intervals of between 15 and 40 minutes, blood samples are drawn from a soft i.v. catheter placed in the left forearm. The determination of the blood glucose level is performed as described in example 166.

Figure 18:
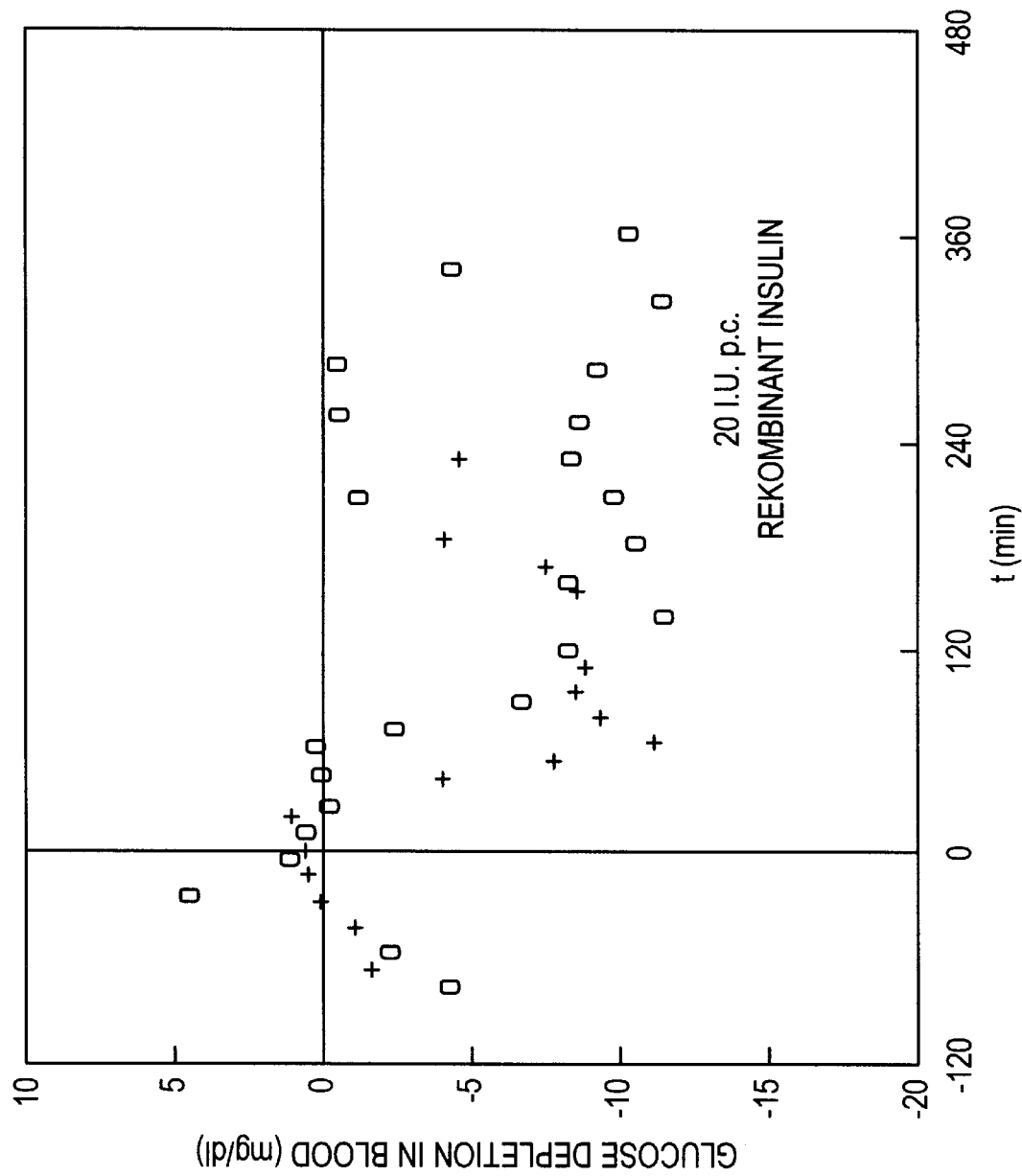
FIG. 18 is a graphical representation of the blood glucose level data described in Example 237.

The course in time of the transfersome mediated hypoglycemia is represented in FIG. 18. The blood glucose level decreases approx. 1.5 hours after drug application by some 10 mg/ml; this artificial hypoglycemia lasts for 4 hours at least and thus attains 70–80% of the value which can be achieved by a subcutaneous application of a comparable amount of the drug Actrapid. The results of control experiments in which the insulin containing transfersomes are injected subcutaneously are shown as crosses in this figure. The total effect in the latter case is similar to that induced by the free drug injected s.c.

Example 238

Composition:

| | |
|---|---|
| 216 mg | phosphatidylcholine from soy-bean (487 µl of a 50% solution in absolute ethanol) |
| 27 mg | phosphatidylglycerol from egg (98%) |
| 29.45 mg | oleic acid, puriss. |
| 3 ml | Actrapid HM 100 (recombinant human insulin 100 I.U. /ml) |
| 40 µl | 1N NaOH |
| 20 µl | 1N NaCl |

Preparation:

Lipids are mixed until solution is homogeneously clear. After the addition of an actrapid solution, of alkali and salt solution, an optically opalescent suspension is formed. Filtering of this suspension through a polycarbonate filter with a pore diameter of 0.2 µm yields a much less opalescent suspension which consists of vesicles (transfersomes) with a mean diameter of 320 nm.

Application:

Starting glucose concentration in the blood of a test person (70 kg, 37 years, normoglycemic, starved for 24 hours) is measured over a period of 90 minutes for reference. Subsequently, the above-mentioned transfersome suspension with a nominal concentration of 85 I.U. insulin/ml, which has been aged for 12 hours at 4° C., is applied on the right forearm skin (approx. 330 µl over an area of approx. 15 cm$^2$); this corresponds to a total applied dose of 28 I.U.

Figure 19:
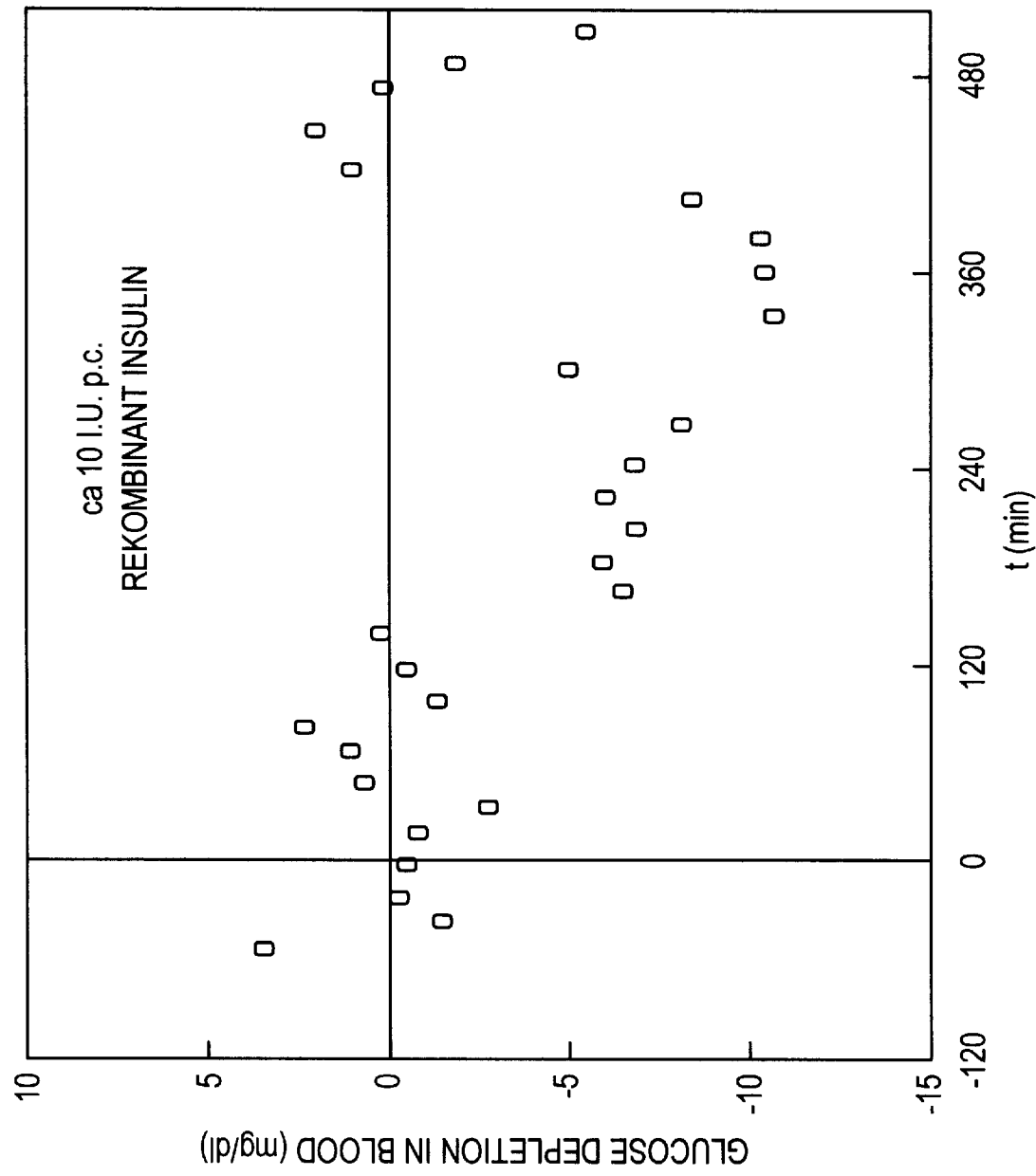
FIG. 19 and FIG. 20 are graphical representations of the data pertaining to glucose depletion in blood, described in Example 238.

Activity:

Blood specimens are collected through a heparinized, permanent, soft catheter placed in a vein in the left forearm; 0.5 ml of each sample are sedimented and immediately frozen for further use. The remaining volume is used for the in situ determination of the blood glucose concentration by an enzymatic method. The measured glucose concentration decreases by approx. 8 mg/dl after approx. 2.5 hours and remains diminished for more than 4.4 hours. This corresponds to 75% of the maximally achievable effect, as concluded from control experiments performed by injecting insulin s.c. The pharmacokinetics of this experimental series is represented in FIG. 19.

Figure 20:
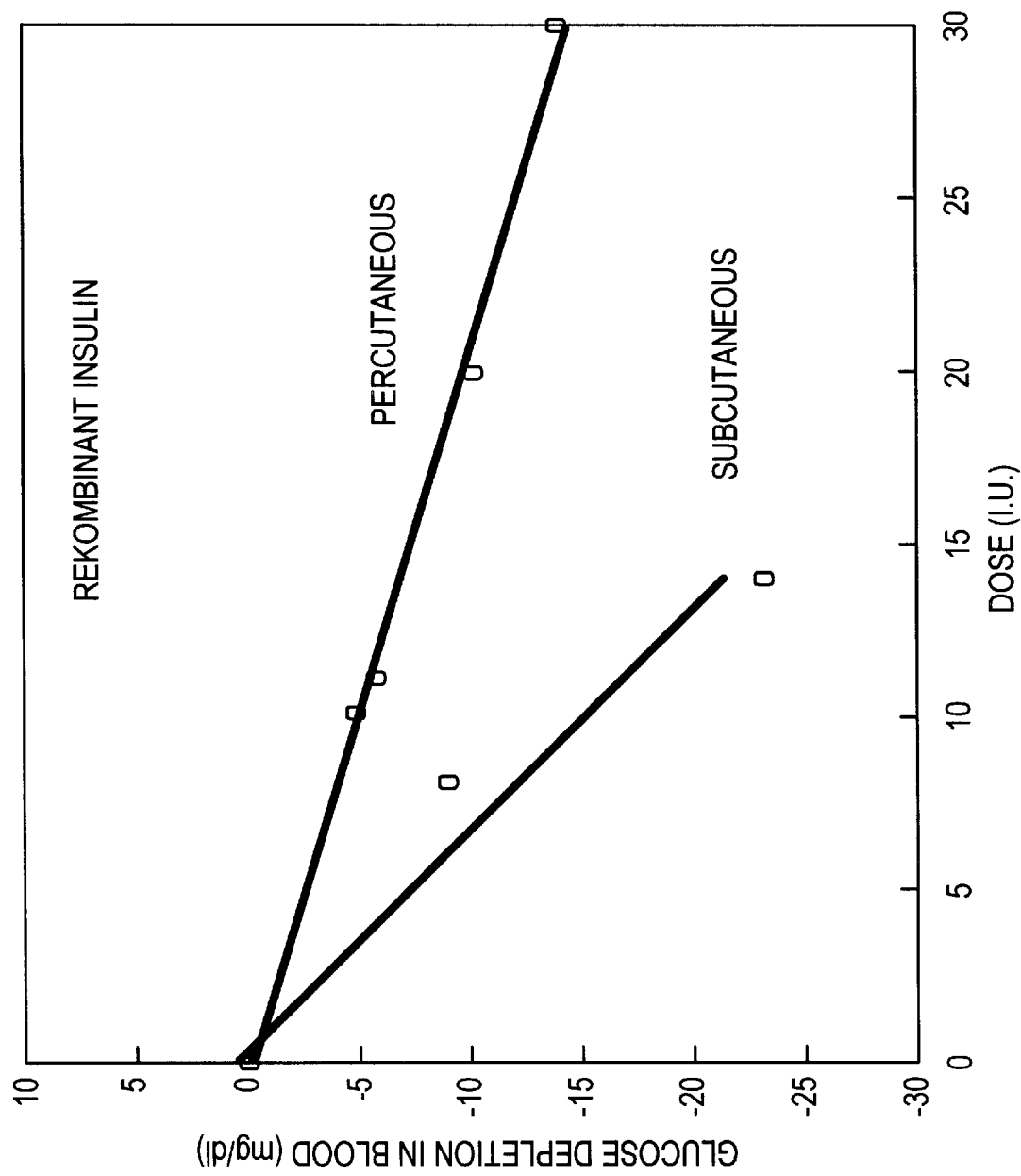

FIG. 20 gives the results of three typical experiments with insulin. They illustrate the results obtained by one percutaneous and two s.c. drug applications.

Example 239

Composition:

| | |
|---|---|
| 143 mg | phosphatidylcholine from soy-bean |
| 18 mg | phosphatidylglycerol from egg (98%) |
| 19.6 mg | oleic acid, puriss. |
| 2 ml | Actrapid HM 100 (200 I.U.) |
| 25 µl | 1N NaOH |

Preparation:

Lipids are weighed into a glass vial and mixed with a standard insulin solution. The resulting opaque suspension is ultrasonicated directly, using a titanium probe-tip (approx. 5 W, 3×5 seconds at 22° C. in 60 seconds intervals). The resulting, optically clear but still opalescent suspension contains vesicles with a mean radius of 114±17 nm.

Application and Activity:

The results of this test series are within the limits of experimental error identical to those obtained in example 238.

Example 240

Composition:

| | |
|---|---|
| 143 mg | phosphatidylcholine from soy-bean |
| 18 mg | phosphatidylglycerol from egg (98%) |
| 20.5 mg | sodium oleate |
| 2 ml | Actrapid HM 100 (200 I.U.) |

Preparation:

The lipids are dissolved in a glass vial in 0.15 ml abs. ethanol and then combined with a standard insulin solution. Further procedure is as described in example 239.

Application and Activity:

Over an area of approx. 5 cm² on the forearm skin of a test person a piece of fine-mesh synthetic cloth is fixed. This is then covered with 350 µl of an insulin containing transfersome suspension and left uncovered to dry.

The resulting decrease of the blood glucose level after 4 hours amounts to 7.8 mg/dl and after 6 hours to 8.5 mg/dl. It is thus comparable to the result obtained in experiment no. 238.

Example 241

The procedure is at first as described in example 238 except that no salt solution is added to the sample suspension; the opaque crude transfersome suspension is divided into two parts. One of these consisting of 50% of the total volume is passed through a sterile filter; the other half is ultrasonicated for 15 seconds at room temperature at a power of approx. 5 W. The mean diameter of carriers in both halves is similar, 300 nm or 240 nm, respectively.

Example 242

The procedure is as described in examples 238 and 240. Transfersomes, however, are filtered one, two and three times in a row. The mean vesicle diameter in the resulting three samples are 300, 240, and 200 nm, resp.

The transfersomes of examples 241 and 242 yield similar hypoglycemic results in biological tests as those of example 238.

Example 243

Composition:

| | |
|---|---|
| 144.9; 152 mg | phosphatidylcholine from soy-bean |
| 24.8; 17.6 mg | desoxycholate, Na-salt |
| 1.45; 1.55 ml | Actrapid HM 100 (145 I.U.) |
| 0.16 ml | ethanol, absolute |

Preparation:

Lipids are weighed into glass vials, dissolved with ethanol and mixed with an insulin solution. The resulting opaque suspension is aged over night and subsequently filtered through a 0.22 micrometer filter at t=12 hours. The nominal insulin concentration is 83 or 84 I.U; the mean vesicle radius in both cases is 112 nm.

Application and Activity:

General experimental conditions are as described in examples 237–239. Transfersome suspensions (0.36 ml, corresponds to 30 I.U.) are applied onto the inner side of a forearm skin in both cases; the blood samples are taken from a soft catheter placed in a vein in the other forearm.

Figure 21:
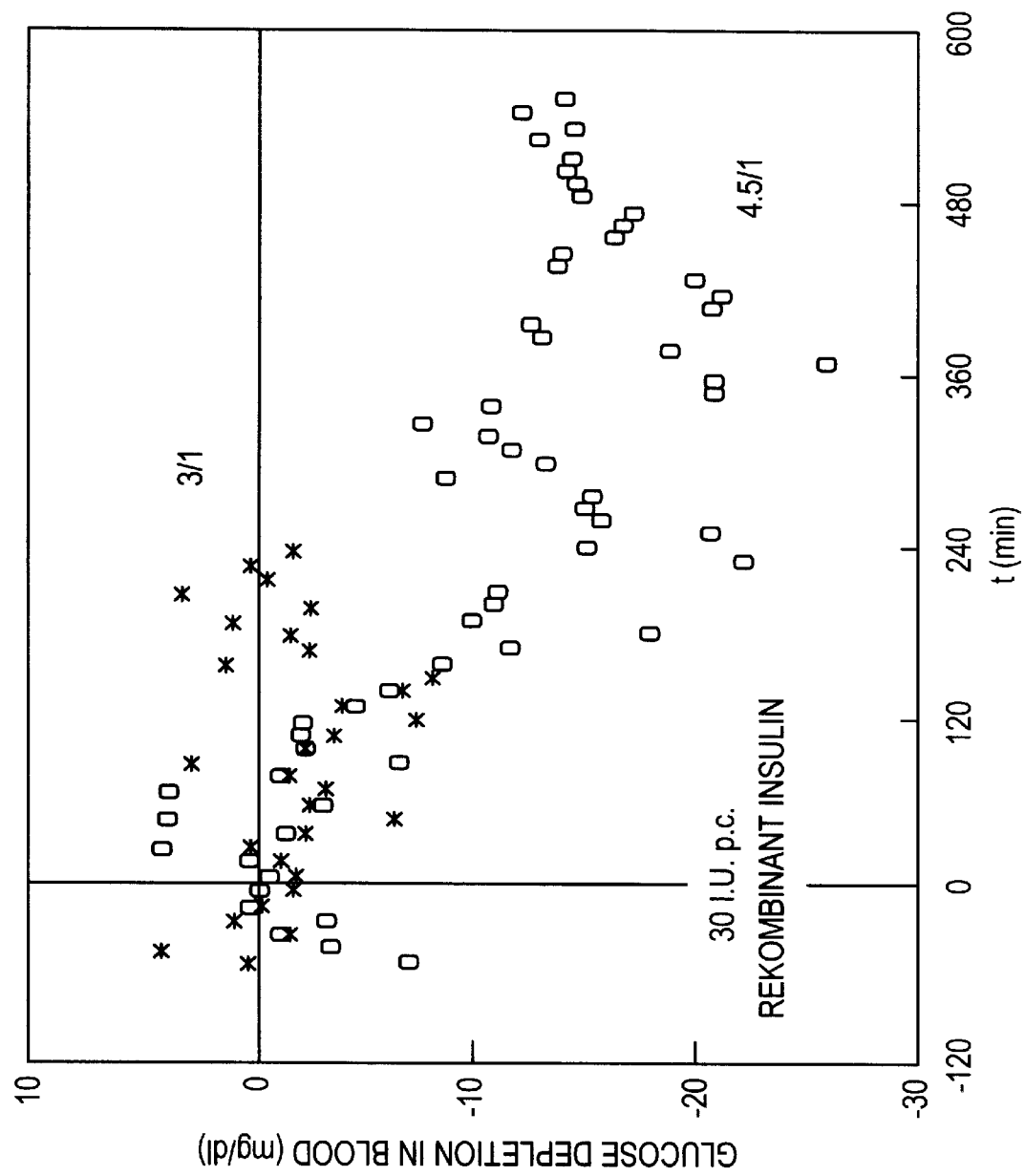

The results of these two experiments are given in FIG. 21. They show that preparations with a relatively high surfactant concentration (Sample 1, L/S=3/1) can cause a hardly significant decrease in the blood glucose level; transfersomes close to their optimum, however, with a surfactant concentration lower by approx. 30% (L/S=4.5/1), cause a very pronounced 'hypoglycemia' which lasts for many hours.

This is another proof that the transfersomes tend to transport drugs through intact skin according to a completely new principle of action which is dissimilar to that of classical pharmaceutical formulations.

This example, in addition to example 236, furthermore, suggests the following conclusion: for the systems investigated, also surfactant concentrations can be used which are remote from the transfersomal optimum (without the carrier activity being lost completely); notwithstanding this, particularly advantageous results are obtained when the surfactant concentration has been determined and chosen to be in a range which ensures maximum carrier elasticity and thus permeation capability of the transfersomes in combination with sufficiently high carrier stability to dissolution, bursting, agent loss, etc.

What is claimed is:

1. A method of transporting medical agents through the skin of a mammal, comprising
   (A) preparing transfersomes comprising a pharmaceutically acceptable lipid and a pharmaceutically acceptable surfactant which is compatible with said lipid, said transfersomes being contained in a pharmaceutically acceptable medium for application onto said skin, said transfersomes containing said lipid and said surfactant in a ratio which enables said transfersomes to undergo sufficient deformation to enable said transfersomes to pass through the skin of said mammal as an entity, such that the total concentration of said lipid in said medium is from about 0.1% to about 30% by weight, and the ratio of lipid to surfactant is from about 5.5:1 to about 1:500, and
   (B) applying a suitable amount of said transfersomes in said medium onto the skin of said mammal such that an effective dose of said lipid, said surfactant, or a further medical agent associated with said transfersomes is absorbed into said mammal.

2. The method of claim 1, wherein said transfersome includes one or several layers.

3. The method of claim 1, wherein the edge tension of a transfersome is about 10 Piconewton or less.

4. The method of claim 1, wherein the concentration of said surfactant edge active substance is between 20 and 50 mol-% of the concentration of surfactant that causes the lipid to be solubilized, and the edge tension of a transfersome is about 10 Piconewton or less.

5. The method of claim 1, further comprising associating a medical agent with said transfersomes said medical agent being contained in the interior of said transfersome, in an outer membrane of said transfersome, or both.

6. The method of claim 1, wherein the total concentration of said lipid in said medium is between 0.1 and 15 weight-%.

7. The method of claim 1, wherein the total concentration of said lipid in said medium is between 5 and 10 weight-%.

8. The method of claim 5, wherein said medical agent comprises a growth modulating substance for living organisms.

9. The method of claim 5, wherein said medical agent comprises at least one antidiabetic agent.

10. The method of claim 5, wherein said medical agent comprises insulin.

11. The method of claim 1 further comprising preparing said transfersomes as unilamellar structures.

12. The method of claim 1 further comprising preparing said transfersomes double layer structures.

13. The method of claim 1, wherein said lipid is a synthetic lipid.

14. The method of claim 1, wherein said lipid is a phospholipid.

15. The method of claim 1, wherein said lipid comprises a glyceride.

16. The method of claim 1, wherein said lipid is selected from the group consisting of glycerophospholipid, isoprenoidlipid, sphingolipid, steroid, a sulfur-containing lipid and a carbohydrate-containing lipid.

17. The method of claim 1, wherein said lipid comprises a fatty acid.

18. The method of claim 1, wherein said lipid is selected from the group consisting of phosphatidylcholine, phosphatidylethanolamine, phosphatidyglycerol, phosphatidylinositol, phosphatidic acid, phosphatidylserine, sphingomyeline, sphingophospholipid, glycosphingolipid, cerebroside, ceramidepolyhexoside, sulfatide, sphingoplasmalogene, a ganglioside, a glycolipid and a synthetic lipid.

19. The method of claim 1, wherein said lipid is selected from the group consisting of a dioleoyl lipid, a dilinoleyl lipid, a dilinolenyl lipid, a dilinolenoyl lipid, a diarachidoyl lipid, a dimyristoyl lipid, a dipalmitoyl lipid, a distearoyl lipid, a diacyl lipid and a dialkyl lipid.

20. The method of claim 13, containing several surfactants.

21. The method of claim 20, wherein said surfactant is selected from the group consisting of nonionic, zwitterionic, anionic and cationic surfactants.

22. The method of claim 20, wherein said surfactant is selected from the group consisting of a long-chain fatty acid, a long-chain fatty alcohol, an alkyl-trimethyl-ammonium-salt, an alkylsulfate salt, a cholate-, a deoxycholate-, a glycodeoxycholate-, taurodeoxycholate, dodecyl-dimethyl-aminoxide, decanoyl-N-methylglucamide dodecanoyl-N-methylglucamide, N-dodecyl-N, N-dimethylglycine, 3-(hexadecyldimethylammonio)-propane-sulfonate, N-hexadecyl-sulfobetaine, nonaethylene-glycoloctylphenylether, nonaethylene-dodecylether, octaethyleneglycol-isotridecylether, octaethylenedodecylether, polyethlene glycol-20-sorbitanemonolaurate, polyhydroxyethylene-cetylstearyl ether polyhydroxyethylene-4-laurylether, polyhydroxyethylene-23-laurylether, polyhydroxyethylene-8-stearate, polyhydroxyethylene-40-stearate, polyhydroxyethylene-100-stearate, polyethoxylated castor oil 40, polyethoxylated hydrated castor oil, sorbitanemonolaurate, lauryl- salts, oleoylsulfate-salts, sodium deoxycholate, sodium glycodeoxycholate, sodium oleate, sodium elaidate, sodium linoleate, sodium laurage, nonaethylene-dodecylether, polyethylene glycol-20-sorbitane-monooleate, polyhydroxyethylene-23-laurylether, polyhydroxyethylene-40-stearate, a sorbitane phospholipid a monolaurate phospholipid and a lysophospholipid.

23. The method of claim 10, comprising 1 through 500 I.U. insulin/ml as said medical agent.

24. The method of claim 10, comprising between 20 and 100 I.U. insulin/ml as said medical agent.

25. The method of claim 21, wherein the concentration of said lipid in said medium is between 0.1 through 20 weight-%.

26. The method of claim 21, wherein the concentration of said lipid in said medium is between 0.5 and 15 weight-%.

27. The method of claim 21, wherein the concentration of said lipid in said medium is between 2.5 and 10 weight-%.

28. The method of claim 1, comprising a phosphatidylcholine or phosphatidylglycol as said lipid.

29. The method of claim 1, wherein said surfactant is selected from the group consisting of lysophosphatidic acid, lysophosphoglycerol, deoxycholate, glycodeoxycholate, laurate, myristate, oleate, palmitoleate, phosphate salts thereof, sulfate salts thereof, a Tween-surfactant and a Myrj-surfactant.

30. The method of claim 23, wherein the medical agent is recombinant human insulin.

31. The method of claim 1, wherein the radius of said transfersomes is between approximately 50 and approximately 200 nm.

32. The method of claim 1, wherein the radius of said transfersomes is between approximately 100 and approximately 180 mn.

33. The method of claim 1, wherein the radius of said transfersomes is from about 50 to about 340 nm.

34. The method of claim 1, wherein the ratio of lipid to surfactant is from about 5:1 to about 1:5.

35. The method of claim 1, wherein the agent is selected from the group consisting of an adrenocorticosteroid or its analogues, an androgen, an antiandrogen, an anabolic steroid, an anaesthetic, an analgesic, an antiallergic, an antiarrhythmic, an antiarterosclerotic, an antiasthmatic, an antidepressant, an antipsychotic, an antidiabetic, an antidote, an antiemetic, an antifibrinolytic, an anticonvulsant, an anticholinergic, an enzyme, a coenzyme, an enzyme inhibitor, an antihistaminic, an antihypertonic, an anticoagulant, an antimycotic, an anti-parkinson agent, an antiphlogistic, an antipyretic, an antirheumatic, an antiseptic, a respiratory agent, a chemotherapeutic, a coronary dilator, an antineoplastic, a diuretic, a ganglium-blocker, a glucocorticoid, an immunologically active substance, a contraceptive, a morphine-antagonist, a muscle relaxant, a narcotic, a nucleotide, a neurotransmitter, an ophthalmic, a sympaticomimetic, a sympatholytic, a parasympaticomimetic, a parasympatholytic, a protein, a protein derivative, an anti-psoriatic, a psychostimulant, a sleep-inducing agent, a sedating agent, a spasmolytic, atuberculosis preparation, a vasoconstrictor, a vasodilator, a wound-healing substance and a combination thereof.

\* \* \* \* \*